United States Patent
He et al.

(10) Patent No.: US 9,139,840 B2
(45) Date of Patent: Sep. 22, 2015

(54) CROP GRAIN FILLING GENE (GIF1) AND THE APPLICATIONS THEREOF

(71) Applicant: Shanghai Institutes for Biological Sciences, Chinese Academy of Sciences, Shanghai (CN)

(72) Inventors: Zuhua He, Shanghai (CN); Hongxia Zhang, Shanghai (CN); Bei Li, Shanghai (CN); Hua Liu, Shanghai (CN)

(73) Assignee: Shanghai Institutes for Biological Sciences, Chinese Academy of Sciences, Shanghai (CN)

( * ) Notice: Subject to any disclaimer, the term of this patent is extended or adjusted under 35 U.S.C. 154(b) by 209 days.

(21) Appl. No.: 13/711,479

(22) Filed: Dec. 11, 2012

(65) Prior Publication Data

US 2013/0160164 A1 Jun. 20, 2013

Related U.S. Application Data

(63) Continuation-in-part of application No. 12/312,235, filed as application No. PCT/CN2007/070984 on Oct. 30, 2007, now Pat. No. 8,329,990.

(30) Foreign Application Priority Data

Oct. 30, 2006 (CN) .......................... 2006 1 0117721

(51) Int. Cl.
*C12N 15/82* (2006.01)
*A01H 5/10* (2006.01)
*C07K 14/415* (2006.01)

(52) U.S. Cl.
CPC .............. *C12N 15/8262* (2013.01); *A01H 5/10* (2013.01); *C07K 14/415* (2013.01); *C12N 15/8245* (2013.01); *C12N 15/8261* (2013.01); *C12N 15/8279* (2013.01)

(58) Field of Classification Search
None
See application file for complete search history.

(56) References Cited

U.S. PATENT DOCUMENTS

2003/0217387 A1 11/2003 Tomes et al.
2009/0293154 A1* 11/2009 Yelin et al. .................... 800/287

FOREIGN PATENT DOCUMENTS

WO 03/008540 A2 1/2003

OTHER PUBLICATIONS

Sequence Accession AF050128, Jan. 5, 1999. Appended to the office action.*
Cho, Jung-Il, et al., "Molecular cloning and expression analysis of the cell-wall invertase gene family in rice (*Oryza sativa* L.)"; Plant Cell Report (2005) vol. 24, No. 4, Jun. 1, 2005; XP019335476, ISSN: 1432-203X; pp. 225-236.
Ji, Xuemei, et al., Structure, Evolution, and Expression of the Two Invertase Gene Families of Rice; Journal of Molecular Evolution, vol. 60, No. 5, May, 2005; XP019363207, ISSN: 0022-2844; pp. 615-634.
Official Action dated May 8, 2013, from the Canadian Intellectual Property Office, issued in related Canadian Patent Application No. CA 2,668,041 (3 pages).
Substantive Examination Report dated May 28, 2013, from the Intellectual Property Office of the Philippines Bureau of Patents, issued in related Philippine Patent Application No. 1/2009/500833 (2 pages).
Ji, X.M., et al, "Tissue-specific expression and drought responsiveness of cell-wall invertase genes of rice at flowering"; Plant Molecular Biology, 2005, vol. 59; DOI: 10.1007/s11103-005-3415-8; pp. 945-964.
Office Action issued in counterpart Philippine Patent Application No. 1/2009/500833 dated Apr. 4, 2014 (2 pages).
Office Action in counterpart Canadian Patent Application No. 2668041 issued Nov. 29, 2013 (2 pages).

* cited by examiner

*Primary Examiner* — Elizabeth McElwain
(74) *Attorney, Agent, or Firm* — Osha Liang LLP

(57) ABSTRACT

Novel crop grain filling genes (GIF1) and the applications thereof are presented in the invention. The GIF1 genes can be applied to control grain filling, enhance crop yield or quality, or improve disease resistance or storage stability of crop grains. A method for improving crops is also presented in the invention. The GIF1 genes shows valuable potentials in controlling crop yield, quality, storage, and resistance to diseases.

5 Claims, 29 Drawing Sheets a pZmPr-*GUS* b pZmPr-*ZmGIF1* c p2X35S-*GIF1*

FIG. 33 (Continued)

```
                          SEQUENCE LISTING

<160> NUMBER OF SEQ ID NOS: 17

<210> SEQ ID NO 1
<211> LENGTH: 1797
<212> TYPE: DNA
<213> ORGANISM: Oryza sativa L.

<400> SEQUENCE: 1
atgggagttc ttggtagtag ggtcgcttgg gcatggctgg tccagctgct gctgctccag      60
cagctcgccg gagcgtcgca cgtcgtctac gacgacctcg agctgcaggc ggctgctacc     120
acagcggacg gcgtgccgcc gtccatcgtc gactctgagc tccggactgg gtatcacttc     180
cagccaccca agaactggat caatgatccg aacgcgccga tgtactacaa ggggtggtac     240
catctgttct accagtacaa ccccaagggc gccgtgtggg ggaacatcgt gtgggcgcac     300
tcagtgtcac gtgacctcat caactgggtg gcgctcaagc cggccatcga gcccagcatc     360
agggccgaca gtacggctg ctggtcgggg tcggcgacga tgatggccga cgggacgccg     420
gtgatcatgt acaccggcgt caaccgcccc gacgtcaact accaggtgca gaacgtggcg     480
ctgccgagga acgggtcgga cccgctgctg cgcgagtggg tgaagcccgg ccacaacccg     540
gtgatcgtgc ccgagggcgg catcaacgcg acgcagttcc gcgacccgac caccgcgtgg     600
cgcggggccg acggccactg gcggctgctc gtcggcagcc tcgcggggca gtcccgcggc     660
gtggcgtacg tgtaccggag cagggacttc cggcggtgga cgcgcgcggc gcagccgctg     720
cactcggcgc ccacggggat gtgggagtgc ccggacttct acccggtcac cgcggacggc     780
cgccgcgagg gcgtcgacac ctcgtccgcc gtcgtcgacg ccgccgcctc ggcgcgcgtc     840
aagtacgtgc tcaagaacag cctcgacctg cgccggtacg actactacac cgtcggaacg     900
tacgaccgga aggccgagcg gtacgtgccg gacgaccccg ccggcgacga gcaccacatc     960
cgctacgact acggcaactt ctacgcctcc aagacgttct acgacccggc gaagcgccgc    1020
cgcatcctct ggggatgggc caacgagtcc gacaccgccg ccgacgacgt ggccaagggc    1080
tgggccggaa tccaggcgat tccgaggaaa gtgtggctgg acccaagtgg gaagcaactg    1140
ttgcagtggc caatcgagga ggtcgagagg ctgagaggga agtggccggt cattctcaag    1200
gacagggtgg tcaagccagg ggaacacgtc gaggtgaccg gctacaaac tgcacaggct    1260 gacgtggagg tgagcttcga ggtggggagc ctggaggcg cggagcggct ggacccggcg    1320
atggcgtacg acgcgcagcg gctgtgcagc gcgcggggcg ccgacgcgag gggcggcgtg    1380
gggccgttcg gcctgtgggt gctcgcgtcc gcggggctgg aggagaagac cgccgtgttc    1440
ttcagggtgt tcaggccggc ggcgcgcggc ggcggcgccg gcaagcccgt cgtgctcatg    1500
tgcaccgacc ccaccaagtc atcgcgcaac ccgaacatgt accagccgac gtttgcaggg    1560
ttcgttgaca cggacatcac caacgggaag atatctctga ggagcctgat cgacaggtcg    1620
gttgttgaga gcttcgggc tggaggaaag gcgtgcatcc tgtcgagggt gtaccgtcg    1680 ctggccatcg gcaagaacgc gcgcctttac gtttcaata acgggaaggc ggagatcaag    1740
gtgtcgcagc tcaccgcgtg ggagatgaag aagccggtca tgatgaatgg agcctaa     1797

<210> SEQ ID NO 2
```

```
<211> LENGTH: 598
<212> TYPE: PRT
<213> ORGANISM: Oryza sativa L.

<400> SEQUENCE: 2

Met Gly Val Leu Gly Ser Arg Val Ala Trp Ala Trp Leu Val Gln Leu
1               5                   10                  15

Leu Leu Leu Gln Gln Leu Ala Gly Ala Ser His Val Val Tyr Asp Asp
            20                  25                  30

Leu Glu Leu Gln Ala Ala Ala Thr Thr Ala Asp Gly Val Pro Pro Ser
        35                  40                  45

Ile Val Asp Ser Glu Leu Arg Thr Gly Tyr His Phe Gln Pro Pro Lys
50                  55                  60

Asn Trp Ile Asn Asp Pro Asn Ala Pro Met Tyr Tyr Lys Gly Trp Tyr
65                  70                  75                  80

His Leu Phe Tyr Gln Tyr Asn Pro Lys Gly Ala Val Trp Gly Asn Ile
                85                  90                  95

Val Trp Ala His Ser Val Ser Arg Asp Leu Ile Asn Trp Val Ala Leu
            100                 105                 110

Lys Pro Ala Ile Glu Pro Ser Ile Arg Ala Asp Lys Tyr Gly Cys Trp
        115                 120                 125

Ser Gly Ser Ala Thr Met Met Ala Asp Gly Thr Pro Val Ile Met Tyr
    130                 135                 140

Thr Gly Val Asn Arg Pro Asp Val Asn Tyr Gln Val Gln Asn Val Ala
145                 150                 155                 160

Leu Pro Arg Asn Gly Ser Asp Pro Leu Leu Arg Glu Trp Val Lys Pro
                165                 170                 175

Gly His Asn Pro Val Ile Val Pro Glu Gly Gly Ile Asn Ala Thr Gln
            180                 185                 190

Phe Arg Asp Pro Thr Thr Ala Trp Arg Gly Ala Asp Gly His Trp Arg
        195                 200                 205

Leu Leu Val Gly Ser Leu Ala Gly Gln Ser Arg Gly Val Ala Tyr Val
    210                 215                 220

Tyr Arg Ser Arg Asp Phe Arg Arg Trp Thr Arg Ala Ala Gln Pro Leu
225                 230                 235                 240

His Ser Ala Pro Thr Gly Met Trp Glu Cys Pro Asp Phe Tyr Pro Val
                245                 250                 255

Thr Ala Asp Gly Arg Arg Glu Gly Val Asp Thr Ser Ser Ala Val Val
            260                 265                 270

Asp Ala Ala Ala Ser Ala Arg Val Lys Tyr Val Leu Lys Asn Ser Leu
        275                 280                 285

Asp Leu Arg Arg Tyr Asp Tyr Tyr Thr Val Gly Thr Tyr Asp Arg Lys
    290                 295                 300

Ala Glu Arg Tyr Val Pro Asp Asp Pro Ala Gly Asp Glu His His Ile
305                 310                 315                 320

Arg Tyr Asp Tyr Gly Asn Phe Tyr Ala Ser Lys Thr Phe Tyr Asp Pro
                325                 330                 335

Ala Lys Arg Arg Arg Ile Leu Trp Gly Trp Ala Asn Glu Ser Asp Thr
            340                 345                 350

Ala Ala Asp Asp Val Ala Lys Gly Trp Ala Gly Ile Gln Ala Ile Pro
        355                 360                 365

Arg Lys Val Trp Leu Asp Pro Ser Gly Lys Gln Leu Leu Gln Trp Pro
    370                 375                 380

Ile Glu Glu Val Glu Arg Leu Arg Gly Lys Trp Pro Val Ile Leu Lys
```

```
                385           390           395           400
Asp Arg Val Val Lys Pro Gly Glu His Val Glu Val Thr Gly Leu Gln
                    405                   410                   415
Thr Ala Gln Ala Asp Val Glu Val Ser Phe Glu Val Gly Ser Leu Glu
                    420                   425                   430
Ala Ala Glu Arg Leu Asp Pro Ala Met Ala Tyr Asp Ala Gln Arg Leu
                    435                   440                   445
Cys Ser Ala Arg Gly Ala Asp Ala Arg Gly Val Gly Pro Phe Gly
    450                   455                   460
Leu Trp Val Leu Ala Ser Ala Gly Leu Glu Glu Lys Thr Ala Val Phe
465                   470                   475                   480
Phe Arg Val Phe Arg Pro Ala Ala Arg Gly Gly Ala Gly Lys Pro
                    485                   490                   495
Val Val Leu Met Cys Thr Asp Pro Thr Lys Ser Ser Arg Asn Pro Asn
                    500                   505                   510
Met Tyr Gln Pro Thr Phe Ala Gly Phe Val Asp Thr Asp Ile Thr Asn
                    515                   520                   525
Gly Lys Ile Ser Leu Arg Ser Leu Ile Asp Arg Ser Val Val Glu Ser
                    530                   535                   540
Phe Gly Ala Gly Gly Lys Ala Cys Ile Leu Ser Arg Val Tyr Pro Ser
545                   550                   555                   560
Leu Ala Ile Gly Lys Asn Ala Arg Leu Tyr Val Phe Asn Asn Gly Lys
                    565                   570                   575
Ala Glu Ile Lys Val Ser Gln Leu Thr Ala Trp Glu Met Lys Lys Pro
                    580                   585                   590
Val Met Met Asn Gly Ala
        595
```

<210> SEQ ID NO 3
<211> LENGTH: 6840
<212> TYPE: DNA
<213> ORGANISM: Oryza sativa L.

<400> SEQUENCE: 3

```
gcttgatcgg ccatactccg aagcctcctc tgggtgagcc tcctagtgta cgataggaca    60
cgaccacata tatgaacact caaccctga acacacacaa tctttaacat acgcttgtaa   120
gatactctct ccgtctcata aaaacgaat ctataaccgg atatgatata ttctagtacg   180
atgaatcttg aaaatgtat gtccagattc gtagtactag gatgtgtcac atctggtatt   240
atgttggttt tttataggac ggaggtagta tataggtccc ttaatttttt tttaaaaaaa   300
gaggtacact atagacaaat ctatctatta tattattaaa ggaatagaaa aaggagcctc   360
cacgttcgct cttatggtct agaaattctc acattaatca gaaaaaaga aaaaatagag   420
ttcatataga aatacaattt agaaaaagct gaatttcgga attaaaaaaa tgaatattag   480
aagaggagac tagagtccat atagaaatac aatttagaaa tagttgaaat tcggaattaa   540
aaaataagga atattagaag aggagactag agtccatata aaatacaat taggaaataa   600
ctgatattca gaatttaaaa taagaatat tagaagtaga gtatagagtc catatagaaa   660
tacaattagg aaataataga aattcggaat taaaataag gaatattaga aatagagtat   720
agagtctata tagaaataca attaagaaaa aaagaaatt cggaattaaa aaataaggaa   780
tattagaaat agagtataga gtctatatag aaatacaatt aagaaaaaaa aatagaaatt   840
cggaattaaa aaatggaat attagaatta gagtatagag tccatatagg aatttaaaac   900
```

```
taactaaaat ttggaataaa cataataaaa ttaaagtaga gtttagagtc cgtataaaaa    960
tacaatttac aaataactaa aattcgagat taagaaaaat atgggaagaa gagtttaaag   1020
tcaatataga aatgcaattt agaagtaact gaaattcgaa attaaaaatt aaagaatatt   1080
gaaagataag tttagagtcc acatagaaat acaattaaaa ataataaaaa ttcagaaata   1140
aaaataaata atattggaag aagagcatag agtctatata gaaatacaat ttacagaaaa   1200
ttcggaatta aaaaatatat attaaaagac gagtctagag tgcatatagg aatatatata   1260
atttacaaat aattaaaaat tgatattaaa ataattaata actaacacgt atataaaata   1320
caatatgaat attacccatt agtagtttcg taaagttatt gcaaaattta aaattatatt   1380
gtcaatttaa tatatttgaa caatatattg agaaaacata tatgctatta tatgagagaa   1440
aatataatag ttcatagtga attgtgaaca ctgatttaaa aacaaacaga ttaacaacca   1500
catcgtttgg cttattcgtg gaataagcta aacggcatat ttgcaaacga aaagtaattt   1560
gtgaataaaa ttttttatata cgtgttctta gcaatctaaa atcaaagagt gaaaaataaa   1620
cttcgatgaa aaaaacccaa aatcagcttc aaatttaaag ttaaaaattt aagtttagct   1680
gataagtata agtataaacg aaaagatgat gccgtaattt tctagacatg aaagatcaat   1740
agaacggatt gacattttcg taatggcctg tagatagaga tataagccac gagaaggagc   1800
agtgctgctc tcttctttac aagctaactt cagtgttttt atacatgaaa aatcgaattg   1860
atatctttgg gttggttcgg attgataacg atctccattc aacttttgct ttttgtttcc   1920
caatacgtta tagatggctt tgtgctccat gcggtgacca tgttaggaaa aaaaagtata   1980
tggatttagg cttgtttgag ctccagctta taaatcagag ccaatatgaa gacaaatccc   2040
aatatatata tatatatata tatatatata tatatatata tatatatata tatatatatc   2100
aaaaacatga gagaaacatg caggtcacgg acgtcccagg gcacaaataa tgttaggtcg   2160
tccacacagt aatgcggccc gcccgggcct gccattcttc tgccctttttg tccgactcag   2220
caatctttga aatctcaacg cttaggggaa aaaaaacagc gtcttttcca taatgcatct   2280
cttcaccttc gcagtataaa taggacccccc tctcctctgc tcctgctcat cctcctctcc   2340
tcttctcgct ctcacttctt gtgcccaagt gtgagagcaa tgggagttct tggtagtagg   2400
gtcgcttggg catggctggt ccagctgctg ctgctccagc agctcgccgg agcgtcgcac   2460
gtcgtctacg acgacctcga gctgcaggcg gctgctacca cagcggacgg cgtgccgccg   2520
tccatcgtcg actctgagct ccggactggg tatcacttcc agccacccaa gaactggatc   2580
aatggtaatg tgaactaact gaaatgttgc caacttgcca ttgttcatgc cagaacgccg   2640
gtcaggccgt atgatttgca ggtcataggg caccacttgt ggttgtggat actggataga   2700
tgagcaaagg gaacagagtg ctctgttctt gagaattgag acgcagaatc gtgcagagta   2760
actagtacag ttttgacgac gttgttgtgt agaacatcac ctgaactaaa tggctcaact   2820
tgagtaattt atagtcagag ttgaaaatat tgacatcata gtcatatcaa atgtttggca   2880
cacaacataa attacggaca gtacactaag gcatcagttt ttatgtccat tttgtcgggt   2940
cagctagtag agtcaacgtt agcacccacg cggtcacgct gaaagaagta gcttcagaag   3000
catctcacag taaactactg agagtttgcc atctctttttt catgaagctc acacttagtc   3060
ccttcgaact gttaacagat gtactacctt gttctacttt tcttgctaat gattcttgtg   3120
acaaggctta gtcctaaccg gcaatttttct tgtgcaatta tttggtgggg gtgtgctctg   3180
ctctacactg tgattgctgc tgcgtcatca acattggaaa cccgcagatc cgaacggtac   3240
gtcgtttttcc caccctttat aatatatcct gtcacgaatc tctgtctact agtagtagta   3300
```

```
gtagtagtac tagaactttt atgccttgca acttgcaatt tcgttgtacg ggagaggact    3360
gtagttagtg acgcctttca tggtaggatt aaaggttcaa agcacatttt agcacgaaaa    3420
tggtaggcgc actgggactc acatgcagg cttgcttgtc gaccgtgggg tacctagccc    3480
ctaccacggc tgatgaccac aaagttcaga aaatcttaac ttcctctcag aaagggaatt    3540
agccaaaagt tcacctttt ctcgtacgaa atgaagcatc tatagttcta taattaatcg    3600
tgagcagtgt agagaaaaat gcaatgtaca cgcgcgatta aactgaaatg gtaattgatt    3660
tcaatgtact actaagactg aagatcattt cttgatttgg tgaaactgaa cgggtgcatg    3720
cagcgccgat gtactacaag gggtggtacc atctgttcta ccagtacaac cccaagggcg    3780
ccgtgtgggg gaacatcgtg tgggcgcact cagtgtcacg tgacctcatc aactgggtgg    3840
cgctcaagcc ggccatcgag cccagcatca gggccgacaa gtacggctgc tggtcggggt    3900
cggcgacgat gatggccgac gggacgccgg tgatcatgta caccggcgtc aaccgccccg    3960
acgtcaacta ccaggtgcag aacgtggcgc tgccgaggaa cgggtcggac ccgctgctgc    4020
gcgagtgggt gaagcccggc cacaacccgg tgatcgtgcc cgagggcggc atcaacgcga    4080
cgcagttccg cgacccgacc accgcgtggc gcggggccga cggccactgg cggctgctcg    4140
tcggcagcct cgcggggcag tcccgcggcg tggcgtacgt gtaccggagc agggacttcc    4200
ggcggtggac gcgcgcggcg cagccgctgc actcggcgcc cacggggatg tgggagtgcc    4260
cggacttcta cccggtcacc gcggacggcc gccgcgaggg cgtcgacacc tcgtccgccg    4320
tcgtcgacgc cgccgcctcg gcgcgcgtca agtacgtgct caagaacagc ctcgacctgc    4380
gccggtacga ctactacacc gtcggaacgt acgaccggaa ggccgagcgg tacgtgccgg    4440
acgaccccgc cggcgacgag caccacatcc gctacgacta cggcaacttc tacgcctcca    4500
agacgttcta cgacccggcg aagcgccgcc gcatcctctg gggatgggcc aacgagtccg    4560
acaccgccgc cgacgacgtg gccaagggct gggccggaat ccaggtaatt aaccgcacgt    4620
cctgactgca tacgtgcatg ccatttacgt gtccaccatg catgctgcca tcttcagata    4680
gtcaatatca ccatatactc cctccgttct aaaatgttta acaccattga cttttttagca    4740 catgtttgac cgttcgtctt attaaaaaaa tatgaaatat ataaaactat atgtatacat    4800
aaaagtatat ttaacaatga atcaaatgat atgaaaagaa caaataatta cttaaatttt    4860
ttgaataaga cgaatggtgt caagtatttt gaaaaaagag agtatatctt aaaagtcaaa    4920
tggaacaaca ctagcagctc aattttgctg gtaatctttg attgaatcgt gtgtttgtga    4980
tgtgatgttt taggcgattc cgaggaaagt gtggctggac ccaagtggga agcaactgtt    5040
gcagtggcca atcgaggagg tcgagaggct gagagggaag tggccggtca ttctcaagga    5100
cagggtggtc aagccagggg aacacgtcga ggtgaccggg ctacaaactg cacaggtatt    5160
cctttttgca tctgtaattc tgtaaaacta tttttttac cccaaaaggg cattcgaata    5220
aaactgctca cacatccatg gttctgtgca tgacagtagt aattattaat aagttatcct    5280
gtttgttttg ctgtgtcctg gaccgatctt tatcttatct ggcacgcctg aagttgtgtc    5340
cagtgtgcag tgcccactga acaccaccta ctacgtgtgc cgtgtcgctt tcttctcgtc    5400
cccttttacc atctcctgca cactttgctc gtacttaact gatctcactg attctctcgt    5460
catccgcgca tgtcacgtac aacttccagg ttgcagcgtg attagtgcac atatcactaa    5520
gacactaaac aacataatta gagagatagt taaggagctc aattaatgtg ctttgttggt    5580
gacgtacgtg agtaggagct gtgatctctg atagcaagtt taatagtata gctaactact    5640
```

```
ggctctaaat tatctatagt caatctaata ataaattcat ataatagtta cctataaaca      5700
tatactaaat aattaataca tggttccaca tgtcatacac atatgcatct taaagtccgt      5760
actataattt gctgtaaatc tatagcttgt tgttttctc tctcctcttt tatctcctcg      5820
atcgaaatgt gtttatagct ggcttatagt gtgctattgt ccctggtctg atgaagtgat      5880
catgcattct gtttggtggg gtgcaggctg acgtggaggt gagcttcgag gtggggagcc      5940
tggaggcggc ggagcggctg gacccggcga tggcgtacga cgcgcagcgg ctgtgcagcg      6000
cgcggggcgc cgacgcgagg ggcggcgtgg ggccgttcgg cctgtgggtg ctcgcgtccg      6060
cggggctgga ggagaagacc gccgtgttct caggggtgtt caggccggcg gcgcgcggcg      6120
gcggcgccgg caagcccgtc gtgctcatgt gcaccgaccc caccaagtac gtgcggcttt      6180
tgcactttat cggtgattga tcgcactaca caataaacaa atattgcct tgactccgtt       6240 tactgatttt ttggtatggt gcgtatgcgt gcaggtcatc gcgcaacccg aacatgtacc      6300
agccgacgtt tgcagggttc gttgacacgg acatcaccaa cgggaagata tctctgagga      6360
gcctggtacg taataggacc aaattatcgg gaaaaagga aatgttgca tgacggtatc        6420 ccgttcggat aaaattatac ctcttaaata ttgtccgata cctaataaat attaattggc      6480
taataaacta tttgaatggg atgatatctt tgaggtatcg tctgatacct atctgatagg     6540
tacctcatag gtatcacctc gtccgaacgg gttactgttt tataacattc atctggaaaa     6600
ggttcataaa ttgtagaata tgttttgata tcttgtgtct ctcttgtgca gatcgacagg      6660
tcggttgttg agagcttcgg ggctggagga aaggcgtgca tcctgtcgag ggtgtacccg      6720
tcgctggcca tcggcaagaa cgcgcgcctt tacgttttca ataacgggaa ggcggagatc      6780
aaggtgtcgc agctcaccgc gtgggagatg aagaagccgg tcatgatgaa tggagcctaa     6840

<210> SEQ ID NO 4
<211> LENGTH: 24
<212> TYPE: DNA
<213> ORGANISM: Artificial
<220> FEATURE:
<221> NAME/KEY: misc_feature
<223> OTHER INFORMATION: primer

<400> SEQUENCE: 4
tataagcttg atcggccata ctcc                                              24

<210> SEQ ID NO 5
<211> LENGTH: 25
<212> TYPE: DNA
<213> ORGANISM: Artificial
<220> FEATURE:
<221> NAME/KEY: misc_feature
<223> OTHER INFORMATION: primer

<400> SEQUENCE: 5
taggatccct ttgctctcac acttg                                             25

<210> SEQ ID NO 6
<211> LENGTH: 1755
<212> TYPE: DNA
<213> ORGANISM: Arabidopsis thaliana

<400> SEQUENCE: 6
atgaccaaag aagtttgctc caacattgga ctttggttat tgctcacgtt acttattggt       60
aactatgtcg tcaatcttga agcctcgcac catgtctaca agagcttac ccaaagcact       120 aacaccaaat ctccttccgt aaaccagccc taccggaccg gtttccattt ccaaccccc        180
```

```
aaaaattgga tgaacgatcc taatgggcct atgatataca aaggaatata tcatcttttc    240
taccaatgga acccgaaagg agccgtgtgg ggtaacatcg tgtgggctca ttccacgtca    300
acagacttaa tcaattggga tccacatcct ccagctatct tcccatctgc acccttcgat    360
atcaacggat gctggtccgg ttcagctact attctcccta atggaaaacc ggttatcctc    420
tataccggaa tcgaccctaa gaaccaacag gtccaaaaca tagccgagcc taagaatctc    480
tccgatcctt atctccgaga atggaaaaag tcgccgttaa atcctctcat ggctcctgac    540
gccgttaacg gaatcaacgc cagctcgttc cgtgacccaa ccaccgcgtg gctaggccaa    600
gacaagaaat ggagagtgat catcggaagc aagattcacc gtcgtggact agccattact    660
tacacgagta aagactttct aaaatgggaa aaatctccag agccgttgca ttacgacgac    720
ggaagtggaa tgtgggaatg tcctgatttt tccccggtca cgaggtttgg ttctaacggc    780
gtggaaacgt cttcgtttgg tgaacctaat gagattttga agcacgtgtt gaaaataagt    840
ttggacgaca cgaaacatga ttattacacg attggtacgt acgatcgggt taagataaaa    900
ttcgtaccgg acaatggttt caagatggac ggtacggctc cgagatacga ttacggaaag    960
tattacgcgt ctaaaacgtt ttttgactcg gctaagaacc ggagaatctt gtggggttgg   1020
actaacgagt catcgtcggt tgaggatgat gttgagaaag gctggtccgg tattcagacg   1080
attccaagga aaatatggct tgatagatca gggaaacaat taattcagtg gccggttagg   1140
gaagttgaaa gattacgtac aaaacaagtc aaaaacttac gcaacaaagt tctaaagtca   1200
ggatctaggc ttgaagtcta tggtgtgaca gctgcacagg cggatgtaga agtattgttc   1260
aaagtgagag acttggagaa agcggatgtg atagaaccaa gttggactga tccgcagttg   1320
atttgtagca agatgaatgt atcggttaag tctggtttag gtccattcgg tttaatggtt   1380
ttggcatcta agaatttgga agagtacaca tctgtttatt ttagaatctt caaagcccgt   1440
caaaacagca ataagtacgt tgtgctcatg tgcagtgacc aaagcagatc ttcgctgaag   1500
gaagataatg acaaaacgac atacggagct tttgtggata ttaatcctca ccaaccacta   1560
tccctcagag ccttgattga tcattcagta gtggagagtt tcggtggaaa gggaagagca   1620
tgcattacct caagagtgta tccaaaattg gcaataggaa aaagttcaca tctctttgct   1680
tttaattatg gatatcaaag tgttgatgtc ttaaacttaa atgcttggag catgaactct   1740
gcccaaatca gttga                                                    1755
```

<210> SEQ ID NO 7
<211> LENGTH: 584
<212> TYPE: PRT
<213> ORGANISM: Arabidopsis thaliana

<400> SEQUENCE: 7

Met Thr Lys Glu Val Cys Ser Asn Ile Gly Leu Trp Leu Leu Leu Thr
1               5                   10                  15

Leu Leu Ile Gly Asn Tyr Val Val Asn Leu Glu Ala Ser His His Val
            20                  25                  30

Tyr Lys Arg Leu Thr Gln Ser Thr Asn Thr Lys Ser Pro Ser Val Asn
        35                  40                  45

Gln Pro Tyr Arg Thr Gly Phe His Phe Gln Pro Lys Asn Trp Met
    50                  55                  60

Asn Asp Pro Asn Gly Pro Met Ile Tyr Lys Gly Ile Tyr His Leu Phe
65                  70                  75                  80

Tyr Gln Trp Asn Pro Lys Gly Ala Val Trp Gly Asn Ile Val Trp Ala

```
                85                  90                  95
His Ser Thr Ser Thr Asp Leu Ile Asn Trp Asp Pro His Pro Ala
                100                 105                 110

Ile Phe Pro Ser Ala Pro Phe Asp Ile Asn Gly Cys Trp Gly Ser
            115                 120                 125

Ala Thr Ile Leu Pro Asn Gly Lys Pro Val Ile Leu Tyr Thr Gly Ile
130                 135                 140

Asp Pro Lys Asn Gln Gln Val Gln Asn Ile Ala Glu Pro Lys Asn Leu
145                 150                 155                 160

Ser Asp Pro Tyr Leu Arg Glu Trp Lys Lys Ser Pro Leu Asn Pro Leu
                165                 170                 175

Met Ala Pro Asp Ala Val Asn Gly Ile Asn Ala Ser Ser Phe Arg Asp
                180                 185                 190

Pro Thr Thr Ala Trp Leu Gly Gln Asp Lys Lys Trp Arg Val Ile Ile
                195                 200                 205

Gly Ser Lys Ile His Arg Arg Gly Leu Ala Ile Thr Tyr Thr Ser Lys
210                 215                 220

Asp Phe Leu Lys Trp Glu Lys Ser Pro Glu Pro Leu His Tyr Asp Asp
225                 230                 235                 240

Gly Ser Gly Met Trp Glu Cys Pro Asp Phe Phe Pro Val Thr Arg Phe
                245                 250                 255

Gly Ser Asn Gly Val Glu Thr Ser Ser Phe Gly Glu Pro Asn Glu Ile
                260                 265                 270

Leu Lys His Val Leu Lys Ile Ser Leu Asp Asp Thr Lys His Asp Tyr
                275                 280                 285

Tyr Thr Ile Gly Thr Tyr Asp Arg Val Lys Asp Lys Phe Val Pro Asp
                290                 295                 300

Asn Gly Phe Lys Met Asp Gly Thr Ala Pro Arg Tyr Asp Tyr Gly Lys
305                 310                 315                 320

Tyr Tyr Ala Ser Lys Thr Phe Phe Asp Ser Ala Lys Asn Arg Arg Ile
                325                 330                 335

Leu Trp Gly Trp Thr Asn Glu Ser Ser Ser Val Glu Asp Asp Val Glu
                340                 345                 350

Lys Gly Trp Ser Gly Ile Gln Thr Ile Pro Arg Lys Ile Trp Leu Asp
                355                 360                 365

Arg Ser Gly Lys Gln Leu Ile Gln Trp Pro Val Arg Glu Val Glu Arg
                370                 375                 380

Leu Arg Thr Lys Gln Val Lys Asn Leu Arg Asn Lys Val Leu Lys Ser
385                 390                 395                 400

Gly Ser Arg Leu Glu Val Tyr Gly Val Thr Ala Ala Gln Ala Asp Val
                405                 410                 415

Glu Val Leu Phe Lys Val Arg Asp Leu Glu Lys Ala Asp Val Ile Glu
                420                 425                 430

Pro Ser Trp Thr Asp Pro Gln Leu Ile Cys Ser Lys Met Asn Val Ser
                435                 440                 445

Val Lys Ser Gly Leu Gly Pro Phe Gly Leu Met Val Leu Ala Ser Lys
450                 455                 460

Asn Leu Glu Glu Tyr Thr Ser Val Tyr Phe Arg Ile Phe Lys Ala Arg
465                 470                 475                 480

Gln Asn Ser Asn Lys Tyr Val Val Leu Met Cys Ser Asp Gln Ser Arg
                485                 490                 495

Ser Ser Leu Lys Glu Asp Asn Asp Lys Thr Thr Tyr Gly Ala Phe Val
                500                 505                 510
```

```
Asp Ile Asn Pro His Gln Pro Leu Ser Leu Arg Ala Leu Ile Asp His
        515                 520                 525

Ser Val Val Glu Ser Phe Gly Gly Lys Gly Arg Ala Cys Ile Thr Ser
    530                 535                 540

Arg Val Tyr Pro Lys Leu Ala Ile Gly Lys Ser Ser His Leu Phe Ala
545                 550                 555                 560

Phe Asn Tyr Gly Tyr Gln Ser Val Asp Val Leu Asn Leu Asn Ala Trp
                565                 570                 575

Ser Met Asn Ser Ala Gln Ile Ser
            580

<210> SEQ ID NO 8
<211> LENGTH: 2957
<212> TYPE: DNA
<213> ORGANISM: Arabidopsis thaliana

<400> SEQUENCE: 8
```

| | | | | | |
|---|---|---|---|---|---|
| acaaaaacca | agccacaaag | aaattaaata | cacacaatga | ccaaagaagt | ttgctccaac | 60 |
| attggacttt | ggttattgct | cacgttactt | attggtaact | atgtcgtcaa | tcttgaagcc | 120 |
| tcgcaccatg | tctacaagag | acttacccaa | agcactaaca | ccaaatctcc | ttccgtaaac | 180 |
| cagccctacc | ggaccggttt | ccatttccaa | ccccccaaaa | attggatgaa | cggtatgacc | 240 |
| aaaatgccat | atctcaacctca | atctcaatgt | ttgttatttt | cattactctc | ttacctttgc | 300 |
| ttttatttcg | ttgtggttcg | tgcttggaca | aaatggattg | atcattggtc | atgagcagat | 360 |
| cctaatggtt | agttttttctc | tcttttatct | cctatctttt | taattttttt | ctcttagtca | 420 |
| actcttcaaa | tccaatagac | agatcatttt | ccctgaaaac | tcgtgttttt | tattatttta | 480 |
| taaaacattg | attacaccaa | tatatgtcag | catacaactg | tacatttgat | tatttgtattg | 540 |
| tattggtcga | ccttgtgtta | cgctgcagga | tccttttaca | ctatccatat | acttaactaa | 600 |
| taaaaataca | catatttaaa | attttaatac | agggcctatg | atatacaaag | gaatatatca | 660 |
| tcttttctac | caatggaacc | cgaaaggagc | cgtgtggggt | aacatcgtgt | gggctcattc | 720 |
| cacgtcaaca | gacttaatca | attgggatcc | acatcctcca | gctatcttcc | catctgcacc | 780 |
| cttcgatatc | aacggatgct | ggtccggttc | agctactatt | ctccctaatg | aaaaaccggt | 840 |
| tatcctctat | accggaatcg | accctaagaa | ccaacaggtc | caaaacatag | ccgagcctaa | 900 |
| gaatctctcc | gatccttatc | tccgagaatg | gaaaaagtcg | ccgttaaatc | tctctcatggc | 960 |
| tcctgacgcc | gttaacggaa | tcaacgccag | ctcgttccgt | gacccaacca | ccgcgtggct | 1020 |
| aggccaagac | aagaaatgga | gagtgatcat | cggaagcaag | attcaccgtc | gtggactagc | 1080 |
| cattacttac | acgagtaaag | actttctaaa | atgggaaaaa | tctccagagc | cgttgcatta | 1140 |
| cgacgacgga | agtggaatgt | gggaatgtcc | tgatttttc | ccggtcacga | ggtttggttc | 1200 |
| taacggcgtg | gaaacgtctt | cgtttggtga | acctaatgag | attttgaagc | acgtgttgaa | 1260 |
| aataagtttg | gacgacacga | acatgattat | ttacacgatt | ggtacgtacg | atcgggttaa | 1320 |
| agataaattc | gtaccggaca | atggtttcaa | gatggacggt | acggctccga | gatacgatta | 1380 |
| cggaaagtat | tacgcgtcta | aaacgttttt | tgactcggct | aagaaccgga | gaatcttgtg | 1440 |
| gggttggact | aacgagtcat | cgtcggttga | ggatgatgtt | gagaaaggct | ggtccggtat | 1500 |
| tcaggtaatt | agttacgctt | aactgaaact | aataatgtga | atataattgt | tagagattga | 1560 |
| atcaattttt | tgtttctttc | ttgattagac | gattccaagg | aaaatatggc | ttgatagatc | 1620 |
| agggaaacaa | ttaattcagt | ggccggttag | ggaagttgaa | agattacgta | caaaacaagt | 1680 |

```
caaaaactta cgcaacaaag ttctaaagtc aggatctagg cttgaagtct atggtgtgac    1740
agctgcacag gtttgattat tatcattttt ttttgaaaaa tcagtaggta tgagaaaatt    1800
agggttttaa aagtcttgtg atttgtacag gcggatgtag aagtattgtt caaagtgaga    1860
gacttggaga aagcggatgt gatagaacca agttggactg atccgcagtt gatttgtagc    1920
aagatgaatg tatcggttaa gtctggttta ggtccattcg gtttaatggt tttggcatct    1980
aagaatttgg aagagtacac atctgtttat tttagaatct tcaaagcccg tcaaaacagc    2040
aataagtacg ttgtgctcat gtgcagtgac caaagcaggt acgtttcttt gattaagatc    2100
gggattaagt atattaattt ttataatctt ttgtcacaat tcacaaatat ttatgtttgt    2160
tttaaacagt cggtcacaaa agatagatct aaaattgggt tccctagaaa tatccaaaac    2220
ttgacttata atttgagga ctttttggtg atgtggattt gggacagatc ttcgctgaag    2280
gaagataatg acaaaacgac atacggagct tttgtggata ttaatcctca ccaaccacta    2340
tccctcagag ccttggtaat taagtctccc attttgtatt ttacgtatat agttttatat    2400
attaatttat gttcatatgt aaaaacgctt gcaaatatag ggaagaaaaa cctccttttt    2460
aaaacccatg agagtaatta tttaacagct tagcctcttg atcaagacta tataatcttc    2520
aactatcttg ttcaagtatt aaggcgaata tttaattgtg gatttgttaa taaaagtttc    2580
tgttatttgt tgttgttggt gtagattgat cattcagtag tggagagttt cggtggaaag    2640
ggaagagcat gcattacctc aagagtgtat ccaaaattgg caataggaaa aagttcacat    2700
ctctttgctt ttaattatgg atatcaaagt gttgatgtct taaacttaaa tgcttggagc    2760
atgaactctg cccaaatcag ttgatcacgt aaagatacac acatgtaaac acattacatc    2820
tccattgatt tagcatttat atgagttgat tttggagaga tcttatatgg tccacttttgt    2880 ttggttgtca ataaaattgt ccaatttgtt tgtttgaaat aattctaaaa ggctaatata    2940
tatgacattt tatttga                                                  2957

<210> SEQ ID NO 9
<211> LENGTH: 1782
<212> TYPE: DNA
<213> ORGANISM: Zea mays

<400> SEQUENCE: 9
atgagagccc tcgtagtcgt aagtttcgct tcggcgtgct tgctgctgct gttgcagctc     60
gcaggagcgt cgcatgtcgt ctacaactac aaggacctcg aagccgaggc tgctgcggcg    120
acggaccagg tgccgccgtc catcgtcaac cccctgctca ggacggggta ccacttccag    180 cccccccaaga actggatcaa tgatcccaac gcgcccatgt actacaaggg gtggtaccat    240
ttcttctacc aatacaatcc caagggcgcc gtatggggca acatcgtgtg ggcgcactcg    300
gtgtcgcgag acctcatcaa ctgggtggcg ctagagccgg cgctcagacc aagcatcccg    360
ggcgacaggc acggctgctg gtccgggtcg gcgacggtgc tgcccgacgg cggcggcccg    420
gtgatcatgt acacgggcgt ggaccacccg gacatcaact accaggtcca gaacgtggcg    480
tacccgaaga acgtgtcgga cccgctgctc cgggagtggg tgaagccctc gcacaacccc    540
gtcatcgtcc ccgagggcgg catcaacgcg acgcagttcc gcgacccgac cacggcctgg    600
cgcggccccg gccccgagca gtggcggctg ctcgtcggca gcggcggcgg gtcgtcgccg    660
ccccgcggcg tggcgtacgt gtaccgtagc cgcgacttcc ggcggtggag gcgggtgcgg    720
cggccgctgc actcggcgcc cacggggatg tgggagtgcc ctgacttcta cccggtgagc    780
```

-continued

```
aagggcggcg cgccgcgcgc ggggctcgag acgtccgtgc cgcccggccc aagggtcaag      840
cacgtgctca agaacagcct cgacctccgg cggtacgact actacaccgt gggcacgtac      900
cacccgaggg ccgagcggta cgtgccggac gaccccgccg gcgacgagca ccgcctgcgc      960
tacgactacg gcaacttcta cgcgtccaag acgttctacg acccggccaa gcggcgccgc     1020
atcctgtggg gctgggctaa cgagtccgac accgccgccg acgatgtggc taaaggctgg     1080
gctggaatcc aggcgattcc aaggacggtg tggctggacc ccagtgggaa gcagctgctg     1140
cagtggccta tcgaggaggt ggaggcgctg agagcaaagt cggtcactct caggaacagg     1200
gtaatcaagg caggacatca cgtcgaggtg accgggatac aaacggcaca ggctgacgtg     1260
gaggtgagct tcgaagtgtc gccggcggcc ctggccggtg ccgagacgct ggacccggcg     1320
ctggcctacg acgcggagag ctgtgcggc gtgaagcgcg cggacgtgag gggcggcgtg     1380
gggccgttcg ggctgtgggt gctggcctcc gccaaccgca aggagagaac cgcggtgttc     1440
ttcagggtgt tcaagcccgc cgccggcgac aagcccgtgg tgctcatgtg caccgacccc     1500
accaagtcgt ccctgaaccc gaacctgtac cgcccgacat ttgcaggatt tgtcgacacg     1560
gacatctcga acggcaagat atccctgaga agcctgatcg accggtcggt cgttgagagc     1620
ttcggagccg ggggcaagac ctgcatcctc tccagggtct accgtcgct ggccatcggc     1680 aaggacgctc gcctctacgt gttcaacaac gggagggcgc acgtcaaggt gtcccgtctc     1740
accgcgtggg agatgaagaa gccggtcatg aacggggcct ga                         1782
```

<210> SEQ ID NO 10
<211> LENGTH: 593
<212> TYPE: PRT
<213> ORGANISM: Zea mays

<400> SEQUENCE: 10

```
Met Arg Ala Leu Val Val Ser Phe Ala Ser Ala Cys Leu Leu Leu
1               5                   10                  15

Leu Leu Gln Leu Ala Gly Ala Ser His Val Val Tyr Asn Tyr Lys Asp
            20                  25                  30

Leu Glu Ala Glu Ala Ala Ala Thr Asp Gln Val Pro Pro Ser Ile
        35                  40                  45

Val Asn Pro Leu Leu Arg Thr Gly Tyr His Phe Gln Pro Pro Lys Asn
    50                  55                  60

Trp Ile Asn Asp Pro Asn Ala Pro Met Tyr Tyr Lys Gly Trp Tyr His
65                  70                  75                  80

Phe Phe Tyr Gln Tyr Asn Pro Lys Gly Ala Val Trp Gly Asn Ile Val
                85                  90                  95

Trp Ala His Ser Val Ser Arg Asp Leu Ile Asn Trp Val Ala Leu Glu
            100                 105                 110

Pro Ala Leu Arg Pro Ser Ile Pro Gly Asp Arg Tyr Gly Cys Trp Ser
        115                 120                 125

Gly Ser Ala Thr Val Leu Pro Asp Gly Gly Pro Val Ile Met Tyr
    130                 135                 140

Thr Gly Val Asp His Pro Asp Ile Asn Tyr Gln Val Gln Asn Val Ala
145                 150                 155                 160

Tyr Pro Lys Asn Val Ser Asp Pro Leu Leu Arg Glu Trp Val Lys Pro
                165                 170                 175

Ser His Asn Pro Val Ile Val Pro Glu Gly Gly Ile Asn Ala Thr Gln
            180                 185                 190

Phe Arg Asp Pro Thr Thr Ala Trp Arg Gly Pro Gly Pro Glu Gln Trp
```

```
            195                 200                 205
Arg Leu Leu Val Gly Ser Ala Ala Gly Ser Ser Pro Pro Arg Gly Val
210                 215                 220

Ala Tyr Val Tyr Arg Ser Arg Asp Phe Arg Arg Trp Arg Arg Val Arg
225                 230                 235                 240

Arg Pro Leu His Ser Ala Pro Thr Gly Met Trp Glu Cys Pro Asp Phe
                245                 250                 255

Tyr Pro Val Ser Lys Gly Gly Ala Pro Arg Ala Gly Leu Glu Thr Ser
                260                 265                 270

Val Pro Pro Gly Pro Arg Val Lys His Val Leu Lys Asn Ser Leu Asp
            275                 280                 285

Leu Arg Arg Tyr Asp Tyr Tyr Thr Val Gly Thr Tyr His Pro Arg Ala
290                 295                 300

Glu Arg Tyr Val Pro Asp Asp Pro Ala Gly Asp Glu His Arg Leu Arg
305                 310                 315                 320

Tyr Asp Tyr Gly Asn Phe Tyr Ala Ser Lys Thr Phe Tyr Asp Pro Ala
                325                 330                 335

Lys Arg Arg Arg Ile Leu Trp Gly Trp Ala Asn Glu Ser Asp Thr Ala
                340                 345                 350

Ala Asp Asp Val Ala Lys Gly Trp Ala Gly Ile Gln Ala Ile Pro Arg
            355                 360                 365

Thr Val Trp Leu Asp Pro Ser Gly Lys Gln Leu Leu Gln Trp Pro Ile
370                 375                 380

Glu Glu Val Glu Ala Leu Arg Ala Lys Ser Val Thr Leu Arg Asn Arg
385                 390                 395                 400

Val Ile Lys Ala Gly His His Val Glu Val Thr Gly Ile Gln Thr Ala
                405                 410                 415

Gln Ala Asp Val Glu Val Ser Phe Glu Val Ser Pro Ala Ala Leu Ala
            420                 425                 430

Gly Ala Glu Thr Leu Asp Pro Ala Leu Ala Tyr Asp Ala Glu Arg Leu
435                 440                 445

Cys Gly Val Lys Arg Ala Asp Val Arg Gly Gly Val Gly Pro Phe Gly
450                 455                 460

Leu Trp Val Leu Ala Ser Ala Asn Arg Lys Glu Arg Thr Ala Val Phe
465                 470                 475                 480

Phe Arg Val Phe Lys Pro Ala Ala Gly Asp Lys Pro Val Leu Met
                485                 490                 495

Cys Thr Asp Pro Thr Lys Ser Ser Leu Asn Pro Asn Leu Tyr Arg Pro
                500                 505                 510

Thr Phe Ala Gly Phe Val Asp Thr Asp Ile Ser Asn Gly Lys Ile Ser
                515                 520                 525

Leu Arg Ser Leu Ile Asp Arg Ser Val Val Glu Ser Phe Gly Ala Gly
530                 535                 540

Gly Lys Thr Cys Ile Leu Ser Arg Val Tyr Pro Ser Leu Ala Ile Gly
545                 550                 555                 560

Lys Asp Ala Arg Leu Tyr Val Phe Asn Asn Gly Arg Ala His Val Lys
                565                 570                 575

Val Ser Arg Leu Thr Ala Trp Glu Met Lys Lys Pro Val Met Asn Gly
            580                 585                 590

Ala

<210> SEQ ID NO 11
<211> LENGTH: 4412
```

<212> TYPE: DNA
<213> ORGANISM: Zea mays

<400> SEQUENCE: 11

| | | | | | |
|---|---|---|---|---|---|
| atgtgagtga | ggccaatgag | agccctcgta | gtcgtaagtt | tcgcttcggc | gtgcttgctg | 60 |
| ctgctgttgc | agctcgcagg | agcgtcgcat | gtcgtctaca | actacaagga | cctcgaagcc | 120 |
| gaggctgctg | cggcgacgga | ccaggtgccg | ccgtccatcg | tcaaccccct | gctcaggacg | 180 |
| gggtaccact | tccagccccc | caagaactgg | atcaatggta | atgtaaagct | actaactaat | 240 |
| ccaccaccca | acgtcgtttg | aaggtgatgt | gtgtgttaag | catctcctga | aatatataag | 300 |
| agagcgaggc | tagtaatcgg | cttgttgttc | agggttttgg | tttaccactt | gtagcctcaa | 360 |
| ctaataaagc | tatatatatg | agagcgacga | gagagaagag | acaaaacatt | catgagtatg | 420 |
| gtcagacaga | ctagctagct | agacacggca | gagaaattac | gagagttaaa | aaaaatgcgc | 480 |
| ttgaagggtg | aaccaaaaca | aaacaacttt | agtactatgc | gtcaacaaag | ctgtgttcat | 540 |
| gtgtcagcta | gcactagagt | catagtgcgt | ggccagtgag | ctgttgtcta | gcaaccaacg | 600 |
| cgaactgaag | tttgagagcg | tactcgtgtt | ctcgatctct | gcagcgcaa | aggtcttcgt | 660 |
| acgtgatcag | gaatattgca | ccatttactg | cttaattaat | taagtacgta | cgtactgtac | 720 |
| gtttggctct | acctcatctt | ctaatctttt | cggtgctgtc | ttgtgctctc | tcggctctga | 780 |
| ttgcatcgat | cggcggcggc | gtgaactttg | caacggcggc | agatcccaac | ggtaataagt | 840 |
| cgttttcccc | accctttta | tttcctctaa | taatgcatca | atattccaac | tgggtgcata | 900 |
| tgcatgcgcg | cagcgcccat | gtactacaag | gggtggtacc | atttcttcta | ccaatacaat | 960 |
| cccaagggcg | ccgtatgggg | caacatcgtg | tgggcgcact | cggtgtcgcg | agacctcatc | 1020 |
| aactgggtgg | cgctagagcc | ggcgctcaga | ccaagcatcc | cggcgacag | gtacggctgc | 1080 |
| tggtccgggt | cggcgacggt | gctgcccgac | ggcggcggcc | cggtgatcat | gtacacgggc | 1140 |
| gtggaccacc | cggacatcaa | ctaccaggtc | cagaacgtgg | cgtacccgaa | gaacgtgtcg | 1200 |
| gacccgctgc | tccgggagtg | ggtgaagccc | tcgcacaacc | ccgtcatcgt | ccccgagggc | 1260 |
| ggcatcaacg | cgacgcagtt | ccgcgacccg | accacggcct | ggcgcggccc | cggccccgag | 1320 |
| cagtggcggc | tgctcgtcgg | cagcgcgcg | gggtcgatgc | cgccccgcgg | cgtggcgtac | 1380 |
| gtgtaccgta | gccgcgactt | ccggcggtgg | aggcgggtgc | ggcggccgct | gcactcggcg | 1440 |
| cccacgggga | tgtgggagtg | ccctgacttc | tacccggtga | gcaagggcgg | cgcgccgcgc | 1500 |
| gcggggctcg | agacgtccgt | gccgcccggc | ccaagggtca | agcacgtgct | caagaacagc | 1560 |
| ctcgacctcc | ggcggtacga | ctactacacc | gtgggcacgt | accacccgag | ggccgagcgg | 1620 |
| tacgtgccgg | acgacccgc | cggcgacgag | caccgcctgc | gctacgacta | cggcaacttc | 1680 |
| tacgcgtcca | agacgttcta | cgacccgcc | aagcggcgcc | gcatcctgtg | gggctgggct | 1740 |
| aacgagtccg | acaccgccgc | cgacgatgtg | gctaaaggct | gggctggaat | ccaggtgcgt | 1800 |
| gcgtgcatgc | ctgcgctagc | tcggctgttc | atccatacgt | atgtatgagt | atgatgactg | 1860 |
| cactgcacgg | ttgtcacgtt | gactcctttc | aacgacgatg | atatgacagg | cgattccaag | 1920 |
| gacggtgtgg | ctggacccca | gtgggaagca | gctgctgcag | tggcctatcg | aggaggtgga | 1980 |
| ggcgctgaga | gcaaagtcgg | tcactctcag | gaacagggta | atcaaggcag | acatcacgt | 2040 |
| cgaggtgacc | gggatacaaa | cggcacaggt | acgtacgtac | ggtacgcgtc | tacttttttt | 2100 |
| ttgttccttt | gcgtggccac | agaactacac | cgagcttcct | gttcgtctgc | atgcaggctg | 2160 |
| acgtggaggt | gagcttcgaa | gtgtcgccgg | cggccctggc | cggtgccgag | acgctggacc | 2220 |

-continued

| | |
|---|---|
| cggcgctggc ctacgacgcg gagaggctgt gcggcgtgaa gcgcgcggac gtgaggggcg | 2280 |
| gcgtggggcc gttcgggctg tgggtgctgg cctccgccaa ccgcaaggag agaaccgcgg | 2340 |
| tgttcttcag ggtgttcaag cccgccgccg gcgacaagcc cgtggtgctc atgtgcaccg | 2400 |
| accctaccaa gtaagtgcta gctgtagctg agcgcaaacc agcagcaaaa gcccgtggtc | 2460 |
| gtccgtccgc tccatgcatg caaagtgctg tggttacatt acacgtacgt atgtactcga | 2520 |
| tcgactgcag tgcatgcaca gttgcacact gacttgtgct ttctgttgct cgcacaactg | 2580 |
| caggtcgtcc ctgaacccga acctgtaccg cccgacattt gcaggatttg tcgacacgga | 2640 |
| catctcgaac ggcaagatat ccctaagaag cctggtacgc gtagagttac acaacaagtt | 2700 |
| ttttttttcgt gcaacaactc cgccgcgttt acgacgtttt cattctcaga catgtgggtt | 2760 |
| cgttattgct tcttcctgct gcagatcgac cgatcggtcg ttgagagctt cggagccggg | 2820 |
| ggcaagacct gcatcctctc cagggtctac ccgtcgctgg ccatcggcaa ggacgctcgc | 2880 |
| ctctacgtgt tcaacaacgg gagggcgcac gtaaaggtgt cccgtctcac cgcgtgggag | 2940 |
| atgaagaagc cggtcatgaa cggggcctga agatcttgaa taaaaaatat atcacccatg | 3000 |
| catgacatag tggcgcctga ggaatctttc cttttttga aaacatattt tagatgtctt | 3060 |
| ttattaagag ttgattgtcc atactaaagg gcgccccgtt ttatgttaca atggtaccag | 3120 |
| ctgcacttct agtaacaaag acaaattgat gactatttgt tgttcacttg caccgttgca | 3180 |
| caatatttaa aagtactttt caatttcaga tgcctactaa aaaaacacaa agtttcaaat | 3240 |
| ttatgaattt aattgtattt tgatgatttt ctgtagaaag aaactaataa tacaataata | 3300 |
| gcctcagaaa tccatgaatt ttatataggc acaaaatatg cccacatata gttctaaaaa | 3360 |
| atgtttggac tcaagcagtg actaaatgat tgcaacaacc gtgatatatg tggaatgatg | 3420 |
| tcttatatgg tatccgacaa aaaaatcgtt atcgatgata tccgtgtttg actagttctg | 3480 |
| tattcgatac acgattatcc gtatttacat atgaaaacac ctgttgtatt tatattcgta | 3540 |
| ttcgtattcg aattcgaatt tgaataaaag tataaaaaca aatatggttt cgatgatatt | 3600 |
| agatccgatt acacccctgc ttgccaccta cgagctcata cgttggattg cttttgatag | 3660 |
| gtcaccaaat gaccaaaaca tgttcggttt ggcaacgtac attccgtgtt ttccttctc | 3720 |
| ttttgtcgac gagctcatac agtcatactg tccctgaaag tttgaaactc cttctgttgg | 3780 |
| tcaacaacga gaaagatggc aggagcgtat cccatgatgg aaatggaagg ggctgagcaa | 3840 |
| gcagcgccgt gcccagtttc tggtaccgtt tggttttact ctccgcacta cgcttagatt | 3900 |
| ttggaaaatt taaagattct cgcttattag ttcgttgaca ccttttcgg gcgccaaaca | 3960 |
| ctcaacaaga accggcggcg gtgctctctg atcaggcgca gacggtccgt ggcacagggc | 4020 |
| cggacggtcc gcgacctggc gcaaggctag agttcccctc ctgacggccg gacagtctgc | 4080 |
| gccctgggac cggacggtcc gcgcgtgcgc aggggcggcg aaggtcaccg gcggcgcctg | 4140 |
| gatctcgctc ccgggaggga cctcgtcgga gaggagagat cctaggagtt gtctaggctc | 4200 |
| ggcaggccga cctagactcc tctaatcgac gtagagtcga agagaagcgg agaatttggg | 4260 |
| gattggaata ctaaactagg gctaaactag aactagacta gaactacttc taatgcataa | 4320 |
| ggtaaaaacg agtaatagac tggatttgat tgattgttgg ggggttcaat cggccgtagc | 4380 |
| ccttcatcta tataaagggg aggtctggat cc | 4412 |

<210> SEQ ID NO 12
<211> LENGTH: 584
<212> TYPE: PRT
<213> ORGANISM: Passiflora quadrangularis

<400> SEQUENCE: 12

Met Asp Lys Leu Leu Gly Thr Ala Leu Leu Lys Phe Leu Pro Val Leu
1               5                   10                  15

Pro Leu Phe Ala Leu Leu Phe Val Leu Ser Asn Asn Gly Val Glu Ala
            20                  25                  30

Ser His Lys Ile Tyr Leu Arg Tyr Gln Ser Leu Ser Val Asp Lys Val
        35                  40                  45

Lys Gln Ile His Arg Thr Gly Tyr His Phe Gln Pro Pro Lys Asn Trp
    50                  55                  60

Ile Asn Asp Pro Asn Gly Pro Leu Tyr Tyr Lys Gly Leu Tyr His Leu
65                  70                  75                  80

Phe Tyr Gln Tyr Asn Pro Lys Gly Ala Val Trp Gly Asn Ile Val Trp
                85                  90                  95

Ala His Ser Val Ser Lys Asp Leu Ile Asn Trp Glu Ser Leu Glu Pro
            100                 105                 110

Ala Ile Tyr Pro Ser Lys Trp Phe Asp Asn Tyr Gly Cys Trp Ser Gly
        115                 120                 125

Ser Ala Thr Ile Leu Pro Asn Gly Glu Pro Val Ile Phe Tyr Thr Gly
    130                 135                 140

Ile Val Asp Gly Asn Asn Arg Gln Ile Gln Asn Tyr Ala Val Pro Ala
145                 150                 155                 160

Asn Ser Ser Asp Pro Tyr Leu Arg Glu Trp Val Lys Pro Asp Asp Asn
                165                 170                 175

Pro Ile Val Tyr Pro Asp Pro Ser Val Asn Ala Ser Ala Phe Arg Asp
            180                 185                 190

Pro Thr Thr Ala Trp Arg Val Gly Gly His Trp Arg Ile Leu Ile Gly
        195                 200                 205

Ser Lys Lys Arg Asp Arg Gly Ile Ala Tyr Leu Tyr Arg Ser Leu Asp
    210                 215                 220

Phe Lys Lys Trp Phe Lys Ala Lys His Pro Leu His Ser Val Gln Gly
225                 230                 235                 240

Thr Gly Met Trp Glu Cys Pro Asp Phe Phe Pro Val Ser Leu Ser Gly
                245                 250                 255

Glu Glu Gly Leu Asp Thr Ser Val Gly Gly Ser Asn Val Arg His Val
            260                 265                 270

Leu Lys Val Ser Leu Asp Leu Thr Arg Tyr Glu Tyr Tyr Thr Ile Gly
        275                 280                 285

Thr Tyr Asp Glu Lys Lys Asp Arg Tyr Tyr Pro Asp Glu Ala Leu Val
    290                 295                 300

Asp Gly Trp Ala Gly Leu Arg Tyr Asp Tyr Gly Asn Phe Tyr Ala Ser
305                 310                 315                 320

Lys Thr Phe Phe Asp Pro Ser Lys Asn Arg Arg Ile Leu Trp Gly Trp
                325                 330                 335

Ala Asn Glu Ser Asp Ser Val Gln Gln Asp Met Asn Lys Gly Trp Ala
            340                 345                 350

Gly Ile Gln Leu Ile Pro Arg Arg Val Trp Leu Asp Pro Ser Gly Lys
        355                 360                 365

Gln Leu Leu Gln Trp Pro Val Ala Glu Leu Glu Lys Leu Arg Ser His
    370                 375                 380

Asn Val Gln Leu Arg Asn Gln Lys Leu Tyr Gln Gly Tyr His Val Glu
385                 390                 395                 400

Val Lys Gly Ile Thr Ala Ala Gln Ala Asp Val Asp Val Thr Phe Ser

```
                    405                 410                 415
Phe Pro Ser Leu Asp Lys Ala Glu Pro Phe Asp Pro Lys Trp Ala Lys
            420                 425                 430

Leu Asp Ala Leu Asp Val Cys Ala Gln Lys Gly Ser Lys Ala Gln Gly
        435                 440                 445

Gly Leu Gly Pro Phe Gly Leu Leu Thr Leu Ala Ser Glu Lys Leu Glu
    450                 455                 460

Glu Phe Thr Pro Val Phe Phe Arg Val Phe Lys Ala Ala Asp Lys His
465                 470                 475                 480

Lys Val Leu Leu Cys Ser Asp Ala Arg Ser Ser Leu Gly Glu Gly
            485                 490                 495

Leu Tyr Lys Pro Pro Phe Ala Gly Phe Val Asp Val Asp Leu Thr Asp
        500                 505                 510

Lys Lys Leu Thr Leu Arg Ser Leu Ile Asp His Ser Val Val Glu Ser
            515                 520                 525

Phe Gly Ala Gly Gly Arg Thr Val Ile Thr Ser Arg Val Tyr Pro Ile
        530                 535                 540

Ile Ala Val Phe Glu Lys Ala His Leu Phe Val Phe Asn Asn Gly Ser
545                 550                 555                 560

Glu Thr Val Thr Val Glu Ser Leu Asp Ala Trp Ser Met Lys Met Pro
            565                 570                 575

Val Met Asn Val Pro Val Lys Ser
            580

<210> SEQ ID NO 13
<211> LENGTH: 580
<212> TYPE: PRT
<213> ORGANISM: Passiflora quadrangularis

<400> SEQUENCE: 13

Met Met Val Met Pro His Thr Leu Pro Val Leu Ala Leu Phe Ala Leu
1               5                   10                  15

Leu Phe Val Leu Ser Asn Asn Gly Ala Glu Ala Ser His Lys Ile Tyr
            20                  25                  30

Ser Arg Tyr Gln Asn Leu Ser Val Glu Asn Val Asn Gln Val His Arg
        35                  40                  45

Thr Gly Tyr His Phe Gln Pro Pro Arg His Trp Ile Asn Asp Pro Asn
    50                  55                  60

Ala Pro Met Tyr Tyr Lys Gly Leu Tyr His Leu Phe Tyr Gln Tyr Asn
65                  70                  75                  80

Pro Lys Gly Ala Val Trp Gly Asn Ile Val Trp Ala His Ser Val Ser
            85                  90                  95

Lys Asp Leu Ile Asn Trp Glu Ser Leu Glu Pro Ala Ile Tyr Pro Ser
        100                 105                 110

Lys Trp Phe Asp Tyr Tyr Gly Cys Trp Ser Gly Ser Ala Thr Val Leu
    115                 120                 125

Pro Asn Gly Glu Pro Val Ile Leu Tyr Thr Gly Ile Val Asp Lys Asn
        130                 135                 140

Asn Ser Gln Ile Gln Asn Tyr Ala Val Pro Ala Asn Leu Ser Asp Pro
145                 150                 155                 160

Tyr Leu Arg Glu Trp Val Lys Pro Asp Asn Pro Ile Val Asn Pro
            165                 170                 175

Asp Ala Asn Val Asn Gly Ser Ala Phe Arg Asp Pro Thr Thr Ala Trp
        180                 185                 190
```

-continued

```
Trp Ala Asp Gly His Trp Arg Ile Leu Ile Gly Ser Arg Lys Gln
            195                 200                 205
Arg Gly Val Ala Tyr Leu Tyr Arg Ser Lys Asp Phe Lys Lys Trp Val
210                 215                 220
Lys Ala Lys His Pro Leu His Ser Val Gln Gly Thr Gly Met Trp Glu
225                 230                 235                 240
Cys Pro Asp Phe Phe Pro Val Ser Leu Ser Gly Lys Asn Gly Leu Asp
                245                 250                 255
Pro Ser Val Met Gly Gln Asn Val His Val Leu Lys Val Ser Leu
                260                 265                 270
Asp Met Thr Arg Tyr Glu Tyr Tyr Thr Met Gly Thr Tyr Asn Lys Lys
            275                 280                 285
Lys Asp Lys Tyr Phe Pro Asp Glu Gly Leu Val Asp Gly Trp Ala Gly
290                 295                 300
Leu Arg Leu Asp Tyr Gly Asn Phe Tyr Ala Ser Lys Thr Phe Phe Asp
305                 310                 315                 320
Pro Ser Thr Asn Arg Arg Val Leu Trp Gly Trp Ala Asn Glu Ser Asp
                325                 330                 335
Asp Pro Gln Lys Asp Lys Asp Lys Gly Trp Ala Gly Ile Gln Leu Ile
            340                 345                 350
Pro Arg Lys Val Trp Leu Asp Pro Ser Gly Lys Gln Leu Leu Gln Trp
            355                 360                 365
Pro Val Ala Glu Leu Glu Lys Leu Arg Gly His Asn Val Gln Leu Arg
370                 375                 380
Asn Gln Lys Leu Asn Gln Gly Asn His Val Glu Val Lys Val Ile Thr
385                 390                 395                 400
Ala Ala Gln Ala Asp Val Asp Val Thr Phe Ser Phe Pro Ser Leu Asp
                405                 410                 415
Lys Ala Glu Pro Phe Asp Pro Lys Trp Ala Lys Leu Asp Ala Leu Asp
            420                 425                 430
Val Cys Asp Gln Lys Gly Ser Lys Asp Pro Gly Gly Leu Gly Pro Phe
            435                 440                 445
Gly Leu Leu Thr Leu Ala Ser Lys Asn Leu Glu Glu Phe Thr Pro Val
450                 455                 460
Phe Phe Arg Val Phe Lys Ala Ala Asp Lys His Lys Val Leu Leu
465                 470                 475                 480
Cys Ser Asp Ala Arg Ser Ser Ser Leu Gly Lys Gly Leu Tyr Lys Pro
                485                 490                 495
Ser Phe Ala Gly Phe Val Asp Val Asp Leu Thr Gly Lys Lys Leu Ser
                500                 505                 510
Leu Arg Ser Leu Ile Asp His Ser Val Val Glu Ser Phe Gly Val Gly
            515                 520                 525
Gly Arg Ile Ala Ile Ser Ser Arg Val Tyr Pro Thr Ile Ala Val Ser
530                 535                 540
Glu Lys Ala His Leu Tyr Val Phe Asn Asn Gly Ser Glu Thr Ile Thr
545                 550                 555                 560
Val Glu Asn Leu Asn Ala Trp Ser Met Asn Thr Pro Val Met Asn Val
                565                 570                 575
Pro Ile Lys Ser
            580

<210> SEQ ID NO 14
<211> LENGTH: 590
<212> TYPE: PRT
```

<213> ORGANISM: Arabidopsis thaliana

<400> SEQUENCE: 14

```
Met Ser Ala Pro Lys Phe Gly Tyr Val Leu Leu Ile Val Leu Ile
1               5                   10                  15

Asn Ile Ser Asn Asn Gly Val Asp Ala Phe His Lys Val Phe Lys Lys
            20                  25                  30

Leu Gln Ser Lys Ser Thr Ser Leu Glu Ser Val Ser Pro Leu His Arg
        35                  40                  45

Thr Ala Tyr His Phe Gln Pro Pro Arg His Trp Ile Asn Asp Pro Asn
    50                  55                  60

Ala Pro Met Leu Tyr Lys Gly Val Tyr His Leu Phe Tyr Gln Tyr Asn
65                  70                  75                  80

Pro Lys Gly Ala Val Trp Gly Asn Ile Val Trp Ala His Ser Val Ser
                85                  90                  95

Lys Asp Leu Ile Asn Trp Glu Ala Leu Glu Pro Ala Ile Tyr Pro Ser
            100                 105                 110

Lys Trp Phe Asp Ile Asn Gly Thr Trp Ser Gly Ser Ala Thr His Val
        115                 120                 125

Pro Gly Lys Gly Pro Val Ile Leu Tyr Thr Gly Ile Thr Glu Asn Gln
    130                 135                 140

Thr Gln Ile Gln Asn Tyr Ala Ile Pro Gln Asp Leu Ser Asp Pro Tyr
145                 150                 155                 160

Leu Lys Thr Trp Ile Lys Pro Asp Asp Asn Pro Ile Val Lys Pro Asp
                165                 170                 175

Asn Gly Glu Asn Gly Ser Ala Phe Arg Asp Pro Thr Thr Ala Trp Phe
            180                 185                 190

Asn Lys Lys Asp Gly Tyr Trp Arg Met Leu Val Gly Ser Lys Arg Lys
        195                 200                 205

Asn Arg Gly Ile Ala Tyr Met Tyr Lys Ser Arg Asp Phe Lys Lys Trp
    210                 215                 220

Val Lys Ser Lys Arg Pro Ile His Ser Arg Lys Thr Gly Met Trp
225                 230                 235                 240

Glu Cys Pro Asp Phe Phe Pro Val Ser Val Thr Asp Lys Lys Asn Gly
                245                 250                 255

Leu Asp Phe Ser Tyr Asp Gly Pro Asn Ala Lys His Val Leu Lys Val
            260                 265                 270

Ser Leu Asp Leu Thr Arg Tyr Glu Tyr Tyr Thr Leu Gly Thr Tyr Asp
        275                 280                 285

Thr Lys Lys Asp Arg Tyr Arg Pro Asp Gly Tyr Thr Pro Asp Gly Trp
    290                 295                 300

Asp Gly Leu Arg Phe Asp Tyr Gly Asn Tyr Tyr Ala Ser Lys Thr Phe
305                 310                 315                 320

Phe Asp Asp Lys Thr Asn Arg Arg Ile Leu Trp Gly Trp Ala Asn Glu
                325                 330                 335

Ser Asp Thr Val Gln Asp Asp Thr Val Lys Gly Trp Ala Gly Ile Gln
            340                 345                 350

Leu Ile Pro Arg Thr Ile Leu Leu Asp Ser Ser Gly Lys Gln Leu Val
        355                 360                 365

Phe Trp Pro Ile Glu Glu Ile Glu Ser Leu Arg Gly Lys Asn Val Gln
    370                 375                 380

Met Thr Asn Gln Lys Met Glu Met Gly Gln Arg Phe Glu Val Gln Gly
385                 390                 395                 400
```

```
Ile Thr Pro Ala Gln Val Asp Val Asp Val Thr Phe Asn Val Gly Asn
                405                 410                 415

Leu Glu Lys Ala Glu Lys Phe Asp Glu Ser Phe Ala Thr Lys Pro Leu
            420                 425                 430

Glu Leu Cys Asn Leu Lys Gly Ser Asn Val Asn Gly Val Gly Pro
            435                 440                 445

Phe Gly Leu Ile Thr Leu Ala Thr Ser Asp Leu Glu Glu Tyr Thr Pro
450                 455                 460

Val Phe Phe Arg Val Phe Lys Asp Ala Ala Ser Asn Lys Pro Lys Val
465                 470                 475                 480

Leu Met Cys Ser Asp Ala Lys Pro Ser Ser Leu Lys Lys Asp Thr Gly
                485                 490                 495

Thr Asp Ala Lys Glu Arg Met Tyr Lys Pro Ser Phe Ala Gly Phe Val
                500                 505                 510

Asp Val Gly Leu Leu Asp Gly Lys Ile Ser Leu Arg Ser Leu Ile Asp
                515                 520                 525

His Ser Val Val Glu Ser Phe Gly Ala Lys Gly Lys Thr Val Ile Thr
            530                 535                 540

Ser Arg Val Tyr Pro Thr Lys Ala Val Gly Glu Lys Ala His Leu Phe
545                 550                 555                 560

Val Phe Asn Asn Gly Ser Gln Pro Val Thr Val Glu Ser Leu Asn Ala
                565                 570                 575

Trp Asn Met Gln Lys Pro Leu Lys Met Asn Gln Gly Ala Lys
                580                 585                 590

<210> SEQ ID NO 15
<211> LENGTH: 577
<212> TYPE: PRT
<213> ORGANISM: Oryza sativa

<400> SEQUENCE: 15

Met Gly Thr Arg Leu Leu Ala Leu Ala Pro Trp Leu Leu Leu Leu
1               5                   10                  15

Leu Gln Leu Ala Gly Ala Ser His Val Val His Arg Ser Leu Glu Ala
            20                  25                  30

Glu Gln Ala Pro Ser Ser Val Pro Ala Ser Ile Val Ser Pro Leu Leu
        35                  40                  45

Arg Thr Gly Tyr His Phe Gln Pro Pro Met Asn Trp Ile Asn Asp Pro
    50                  55                  60

Asn Gly Pro Leu Tyr Tyr Lys Gly Trp Tyr His Leu Phe Tyr Gln Tyr
65                  70                  75                  80

Asn Pro Lys Gly Ala Val Trp Gly Asn Ile Val Trp Ala His Ser Val
                85                  90                  95

Ser Gln Asp Leu Ile Asn Trp Ile Ala Leu Glu Pro Ala Ile Lys Pro
            100                 105                 110

Asp Ile Pro Ser Asp Gln Tyr Gly Cys Trp Ser Gly Ser Ala Thr Ile
        115                 120                 125

Leu Pro Asp Gly Thr Pro Ala Ile Leu Tyr Thr Gly Ile Asp Arg Pro
    130                 135                 140

Asn Ile Asn Tyr Gln Val Gln Asn Ile Ala Phe Pro Lys Asn Ala Ser
145                 150                 155                 160

Asp Pro Leu Leu Arg Glu Trp Val Lys Pro Ala Tyr Asn Pro Val Ala
                165                 170                 175

Thr Pro Glu Pro Gly Met Asn Ala Thr Gln Phe Arg Asp Pro Thr Thr
            180                 185                 190
```

Ala Trp Tyr Ala Asp Gly His Trp Arg Met Leu Val Gly Gly Leu Lys
            195                 200                 205

Gly Ala Arg Leu Gly Leu Ala Tyr Leu Tyr Arg Ser Arg Asp Phe Lys
    210                 215                 220

Thr Trp Val Arg Ala Lys His Pro Leu His Ser Ala Leu Thr Gly Met
225                 230                 235                 240

Trp Glu Cys Pro Asp Phe Phe Pro Leu Gln Ala Pro Gly Leu Gln Ala
                245                 250                 255

Gly Leu Asp Thr Ser Val Pro Ser Ser Lys Tyr Val Leu Lys Asn Ser
            260                 265                 270

Leu Asp Leu Thr Arg Tyr Asp Tyr Tyr Thr Val Gly Ile Tyr Asn Lys
        275                 280                 285

Val Thr Glu Arg Tyr Val Pro Asp Asn Pro Ala Gly Asp Tyr His Arg
    290                 295                 300

Leu Arg Tyr Asp Tyr Gly Asn Phe Tyr Ala Ser Lys Thr Phe Phe Asp
305                 310                 315                 320

Pro Val Lys His Arg Arg Ile Leu Leu Gly Trp Ala Asn Glu Ser Asp
                325                 330                 335

Ser Val Thr Tyr Asp Lys Ala Lys Gly Trp Ala Gly Ile His Ala Ile
            340                 345                 350

Pro Arg Lys Val Trp Leu Asp Pro Ser Gly Lys Gln Leu Leu Gln Trp
        355                 360                 365

Pro Ile Glu Glu Leu Glu Thr Leu Arg Gly Lys Ser Val Ser Val Phe
    370                 375                 380

Asp Lys Val Val Lys Pro Gly Glu His Phe Gln Val Thr Gly Leu Gly
385                 390                 395                 400

Thr Tyr Gln Ala Asp Val Glu Val Ser Leu Glu Val Ser Gly Leu Glu
                405                 410                 415

Lys Ala Glu Ala Leu Asp Pro Ala Phe Gly Asp Asp Ala Glu Arg Leu
            420                 425                 430

Cys Gly Ala Lys Gly Ala Asp Val Arg Gly Val Val Phe Gly Leu
        435                 440                 445

Trp Val Leu Ala Ser Ala Gly Leu Glu Glu Lys Thr Ala Val Phe Phe
    450                 455                 460

Arg Val Phe Lys Pro Ala Gly His Gly Ala Lys Pro Val Val Leu Met
465                 470                 475                 480

Cys Thr Asp Pro Thr Lys Ser Ser Leu Ser Pro Asp Leu Tyr Lys Pro
                485                 490                 495

Thr Phe Ala Gly Phe Val Asp Thr Asp Ile Ser Ser Gly Lys Ile Ser
            500                 505                 510

Leu Arg Ser Leu Ile Asp Arg Ser Val Val Glu Ser Phe Gly Ala Gly
        515                 520                 525

Gly Lys Thr Cys Ile Leu Ser Arg Val Tyr Pro Ser Met Ala Ile Gly
    530                 535                 540

Asp Lys Ala His Leu Tyr Val Phe Asn Asn Gly Glu Ala Asp Ile Lys
545                 550                 555                 560

Ile Ser His Leu Lys Ala Trp Glu Met Lys Lys Pro Leu Met Asn Gly
                565                 570                 575

Ala

<210> SEQ ID NO 16
<211> LENGTH: 590
<212> TYPE: PRT

-continued

<213> ORGANISM: Zea mays

<400> SEQUENCE: 16

Met Gly Thr Arg Pro Arg Gly Val Val Leu Ala Pro Trp Ala Val Val
1               5                   10                  15

Leu Val Leu Val Leu Ala Leu Arg Leu Ala Gly Ala Ser His Val Ile
            20                  25                  30

His Arg Ser Leu Glu Ala Glu Ala Ala Pro Ser Val Pro Ala Ser Ile
        35                  40                  45

Val Ser Pro Leu Leu Arg Thr Gly Tyr His Phe Gln Pro Pro Met Asn
    50                  55                  60

Trp Ile Asn Asp Pro Asn Ala Pro Leu Tyr Tyr Lys Gly Trp Tyr His
65                  70                  75                  80

Leu Phe Tyr Gln Tyr Asn Pro Lys Gly Ala Val Trp Gly Asn Ile Val
                85                  90                  95

Trp Ala His Ser Val Ser Arg Asp Leu Ile Asn Trp Val Ala Leu Glu
            100                 105                 110

Pro Ala Ile Tyr Pro Ser Ile Pro Ser Asp Lys Tyr Gly Cys Trp Ser
        115                 120                 125

Gly Ser Ala Thr Ile Leu Glu Asp Gly Thr Pro Ala Ile Leu Tyr Thr
    130                 135                 140

Gly Ile Asp Arg Ala Asp Ile Asn Tyr Gln Val Gln Val Leu Ala Leu
145                 150                 155                 160

Pro Lys Asp Ala Ser Asp Pro Leu Leu Arg Glu Trp Glu Lys Pro Glu
                165                 170                 175

Glu Tyr Asn Pro Val Ala Thr Pro Ala Ala Gly Ile Asn Ala Thr
            180                 185                 190

Gln Phe Arg Asp Pro Thr Thr Ala Trp Arg His Ala Gly His Trp Arg
        195                 200                 205

Met Leu Val Gly Ser Val Arg Gly Ala Arg Gly Met Ala Leu Val Tyr
    210                 215                 220

Arg Ser Arg Asp Phe Arg Lys Trp Thr Lys Ala Lys His Pro Leu His
225                 230                 235                 240

Ser Ala Ala Leu Thr Gly Met Trp Glu Cys Pro Asp Phe Phe Pro Val
                245                 250                 255

Ser Gly Pro Gly Leu Gln Ala Gly Leu Asp Thr Ser Ala Pro Gly Thr
            260                 265                 270

Lys Tyr Val Leu Lys Ser Ser Leu Asp Leu Thr Arg Tyr Asp Tyr Tyr
        275                 280                 285

Thr Ile Gly Ser Tyr Asp Gly Lys Asp Arg Tyr Tyr Pro Asp Asp
    290                 295                 300

Pro Ala Gly Asp Tyr His His Arg Arg Arg Tyr Asp Tyr Gly Asn Tyr
305                 310                 315                 320

Tyr Ala Ser Lys Thr Phe Tyr Asp Pro Val Glu Arg Arg Val Leu
                325                 330                 335

Leu Gly Trp Ala Asn Glu Ser Asp Ser Val Pro Asp Lys Ala Lys
            340                 345                 350

Gly Trp Ala Gly Ile His Ala Ile Pro Arg Lys Ile Trp Leu Asp Pro
        355                 360                 365

Thr Gly Lys Gln Leu Leu Gln Trp Pro Ile His Glu Val Glu Lys Leu
    370                 375                 380

Arg Gly Lys Ala Val Ser Val Asp Ala Lys Leu Val Lys Pro Gly Asp
385                 390                 395                 400

-continued

```
His Phe Glu Val Thr Gly Ile Ala Thr Tyr Gln Ala Asp Val Glu Val
                405                 410                 415

Ser Phe Glu Leu Glu Leu Glu Ala Gly Thr Ser Leu Leu Glu Lys Ala
            420                 425                 430

Glu Ala Phe Asp Pro Ala Tyr Asp Asp Ala Gln Lys Leu Cys Gly
        435                 440                 445

Val Lys Gly Ala Asp Ala Arg Gly Val Gly Pro Phe Gly Leu Trp
    450                 455                 460

Val Leu Ala Ser Ala Asp Leu Gln Glu Arg Thr Ala Val Phe Phe Arg
465                 470                 475                 480

Val Phe Arg Asp Gly His Gly Lys Pro Lys Val Leu Met Cys Thr Asp
                485                 490                 495

Pro Thr Lys Ser Ser Leu Ser Pro Asp Leu Tyr Lys Pro Thr Phe Ala
            500                 505                 510

Gly Phe Val Asp Ala Asp Ile Ser Ser Gly Lys Ile Thr Leu Arg Ser
        515                 520                 525

Leu Ile Asp Arg Ser Val Val Glu Ser Phe Gly Ala Gly Gly Lys Thr
    530                 535                 540

Cys Ile Leu Ser Arg Val Tyr Pro Ser Ile Ala Val Gly Lys Asp Ala
545                 550                 555                 560

His Leu Tyr Val Phe Asn Asn Gly Glu Val Asp Val Thr Val Ser Gly
                565                 570                 575

Leu Thr Ala Trp Glu Met Lys Lys Pro Leu Met Asn Gly Ala
            580                 585                 590

<210> SEQ ID NO 17
<211> LENGTH: 598
<212> TYPE: PRT
<213> ORGANISM: Oryza sativa

<400> SEQUENCE: 17

Met Gly Val Leu Gly Ser Arg Val Ala Trp Ala Trp Leu Val Gln Leu
1               5                   10                  15

Leu Leu Leu Gln Gln Leu Ala Gly Ala Ser His Val Val Tyr Asp Asp
            20                  25                  30

Leu Glu Leu Gln Ala Ala Ala Thr Thr Ala Asp Gly Val Pro Pro Ser
        35                  40                  45

Ile Val Asp Ser Glu Leu Arg Thr Gly Tyr His Phe Gln Pro Pro Lys
    50                  55                  60

Asn Trp Ile Asn Asp Pro Asn Ala Pro Met Tyr Tyr Lys Gly Trp Tyr
65                  70                  75                  80

His Leu Phe Tyr Gln Tyr Asn Pro Lys Gly Ala Val Trp Gly Asn Ile
                85                  90                  95

Val Trp Ala His Ser Val Ser Arg Asp Leu Ile Asn Trp Val Ala Leu
            100                 105                 110

Lys Pro Ala Ile Glu Pro Ser Ile Arg Ala Asp Lys Tyr Gly Cys Trp
        115                 120                 125

Ser Gly Ser Ala Thr Met Met Ala Asp Gly Thr Pro Val Ile Met Tyr
    130                 135                 140

Thr Gly Val Asn Arg Pro Asp Val Asn Tyr Gln Val Gln Asn Val Ala
145                 150                 155                 160

Leu Pro Arg Asn Gly Ser Asp Pro Leu Leu Arg Glu Trp Val Lys Pro
                165                 170                 175

Gly His Asn Pro Val Ile Val Pro Glu Gly Gly Ile Asn Ala Thr Gln
            180                 185                 190
```

```
Phe Arg Asp Pro Thr Thr Ala Trp Arg Gly Ala Asp Gly His Trp Arg
    195                 200                 205

Leu Leu Val Gly Ser Leu Ala Gly Gln Ser Arg Gly Val Ala Tyr Val
210                 215                 220

Tyr Arg Ser Arg Asp Phe Arg Arg Trp Thr Arg Ala Ala Gln Pro Leu
225                 230                 235                 240

His Ser Ala Pro Thr Gly Met Trp Glu Cys Pro Asp Phe Tyr Pro Val
                245                 250                 255

Thr Ala Asp Gly Arg Arg Glu Gly Val Asp Thr Ser Ser Ala Val Val
                260                 265                 270

Asp Ala Ala Ser Ala Arg Val Lys Tyr Val Leu Lys Asn Ser Leu
                275                 280                 285

Asp Leu Arg Arg Tyr Asp Tyr Tyr Thr Val Gly Thr Tyr Asp Arg Lys
    290                 295                 300

Ala Glu Arg Tyr Val Pro Asp Pro Ala Gly Asp Glu His His Ile
305                 310                 315                 320

Arg Tyr Asp Tyr Gly Asn Phe Tyr Ala Ser Lys Thr Phe Tyr Asp Pro
                325                 330                 335

Ala Lys Arg Arg Arg Ile Leu Trp Gly Trp Ala Asn Glu Ser Asp Thr
                340                 345                 350

Ala Ala Asp Asp Val Ala Lys Gly Trp Ala Gly Ile Gln Ala Ile Pro
                355                 360                 365

Arg Lys Val Trp Leu Asp Pro Ser Gly Lys Gln Leu Leu Gln Trp Pro
    370                 375                 380

Ile Glu Glu Val Glu Arg Leu Arg Gly Lys Trp Pro Val Ile Leu Lys
385                 390                 395                 400

Asp Arg Val Val Lys Pro Gly Glu His Val Glu Val Thr Gly Leu Gln
                405                 410                 415

Thr Ala Gln Ala Asp Val Glu Val Ser Phe Glu Val Gly Ser Leu Glu
                420                 425                 430

Ala Ala Glu Arg Leu Asp Pro Ala Val Ala Tyr Asp Ala Gln Arg Leu
    435                 440                 445

Cys Ser Ala Arg Gly Ala Asp Ala Arg Gly Gly Val Gly Pro Phe Gly
450                 455                 460

Leu Trp Val Leu Ala Ser Ala Gly Leu Glu Glu Lys Thr Ala Val Phe
465                 470                 475                 480

Phe Arg Val Phe Arg Pro Ala Ala Arg Gly Gly Ala Gly Lys Pro
                485                 490                 495

Val Val Leu Met Arg Thr Asp Pro Thr Lys Ser Ser Arg Asn Pro Asn
                500                 505                 510

Met Tyr Gln Pro Thr Phe Ala Gly Phe Val Asp Thr Asp Ile Thr Asn
                515                 520                 525

Gly Lys Ile Ser Leu Arg Ser Leu Ile Asp Arg Ser Val Val Glu Ser
530                 535                 540

Phe Gly Ala Gly Gly Lys Ala Cys Ile Leu Ser Arg Val Tyr Pro Ser
545                 550                 555                 560

Leu Ala Ile Gly Lys Asn Ala Arg Leu Tyr Val Phe Asn Asn Gly Lys
                565                 570                 575

Ala Glu Ile Lys Val Ser Gln Leu Thr Ala Trp Glu Met Lys Lys Pro
                580                 585                 590

Val Met Met Asn Gly Ala
                595
```

CROP GRAIN FILLING GENE (GIF1) AND THE APPLICATIONS THEREOF

CROSS REFERENCE TO RELATED APPLICATIONS

This is a Continuation in Part application of application Ser. No. 12/312,235, filed on Apr. 30, 2009, which is a national phase application of PCT/CN2007/070984, filed on Oct. 30, 2007, which claims priority of Chinese Application No. 200610117721.6, filed on Oct. 30, 2006. This application claims the benefits and priority of these prior applications and incorporates these prior applications by reference in their entireties.

TECHNICAL FIELD

This invention relates to gene technology and botany field; particularly, relates to a novel crop grain filling gene, GIF1 (Grain Incomplete Filling 1) gene, and its applications.

BACKGROUND ART

Currently, investigations concerning the improvement of crop yield are mainly focused on the following aspects: 1. increasing crop sources, viz. improving crop photosynthesis; 2. elevating the sink volume; and, 3. enhancing the transport ability of photosynthate from source to sink. Among them, elevation in the sink volume and enhancement of transport ability of photosynthate from source to sink are effective breeding approaches.

Several approaches have been adopted to enhance crop yield and modify the crops. However, there still lacks effective means. With respect to rice, the major cereal crops of China, grain incomplete filling is present in many high yield varieties, especially in super hybrid rice and rice varieties with large ear and large grain, and greatly affects the improvement in the rice yield. In addition to rice, wheat and maize (Zea mays) have been grown worldwide as an important grain crops. Together, they constitute the world's major staple food crops. Grain incomplete filling also impacts wheat, maize, and other crops.

Therefore, it is desirable to search for an effective approach in the field to solve the problem of grain incomplete filling, thus further modifying the crops and enhancing the crop yield as well as crop quality.

SUMMARY OF THE INVENTION

The object of the present invention is to provide a novel crop grain filling gene, GIF1 (Grain Incomplete Filling 1) gene, and its applications.

In the first aspect of the invention, an isolated crop grain filling protein is presented, wherein the protein is selected from a group consisting of:

(a) a polypeptide having the amino acid sequence of SEQ ID NO: 2; or (b) a polypeptide derived from the polypeptide of (a) with one or more amino acid residues in SEQ ID NO:2 being substituted, deleted or added, and capable of promoting grain filling.

In the second aspect of the invention, an isolated polynucleotide is presented, wherein the polynucleotide is selected from:

(i) a polynucleotide that encodes the grain filling protein; or (ii) a polynucleotide complementary with the polynucleotide of (i).

In another preferred embodiment, the polynucleotide encodes the polypeptide having SEQ ID NO: 2.

In another preferred embodiment, the sequence of the polynucleotide is selected from:

(1) a nucleotide sequence of SEQ ID NO: 1;

(2) a nucleotide sequence of SEQ ID NO: 3; or (3) a nucleotide sequence complementary to any one of the nucleotide sequence of (1) or (2).

In the third aspect of the invention, a vector is presented, wherein the vector contains said polynucleotide.

In the fourth aspect of the invention, a genetically engineered host cell is presented, wherein the cell contains said vector or the cell genome is integrated with said polynucleotide.

In the fifth aspect of the invention, a use of the grain filling protein or its encoding gene is presented, which comprises:

regulating grain filling (preferably facilitating crop grain filling);

regulating sugar metabolism or accumulation involved in crop grains; or improving the disease tolerance and storage stability of crop grains.

In the sixth aspect of the invention, a method for modifying crops was presented, which comprises: increasing the expression of said grain filling gene in the crop.

In the seventh aspect of the invention, a method for preparing transgenic plants was presented, which comprises the step of: introducing the polynucleotide of the present application into plant cells or tissues, culturing said plant cells or tissues, and regenerating said plant cells or tissues to plants.

In another preferred embodiment of the invention, the method comprises the steps of:

(a) providing *Agrobacterium tumefaciens* carrying the expression vector, wherein the expression vector comprises the encoding gene for the grain filling protein;

(b) contacting crop cells, tissues or organs with the *Agrobacterium tumefaciens* in step (a) so as to introduce the DNA sequence encoding grain filling protein into said crop cells, tissues or organs, and integrate the same into the crop chromosome;

(c) regenerating the crop cells, tissues or organs introduced with the DNA sequence encoding grain filling protein to crop plants.

In the eighth aspect of the invention, an agonist or antagonist for the grain filling protein or its encoding gene is presented.

Other aspects of the invention will be readily apparent to those skilled in the art based on the contents contained in the invention.

BRIEF DESCRIPTION OF THE FIGURES

FIG. 1B refers to brown rice grains of mutant plant; FIG. 1C refers to polished rice grains of wild-type plant; and FIG. 1D refers to polished rice grains of mutant plant.

FIG. 4B and FIG. 4D (magnification of FIG. 4B) refer to the isolated *Alternaria* sp.

1-7, PCR products with transgenic plant genomic DNA as template. (b) RT-PCR analysis. RT-PCR was performed using ZmFIF1-specific primers or Actin1-specific primers. The Actin1 gene was used as an internal control. (c) Kernels of Ye478 (WT) and transgenic maize plants ($T_4$).

Figure 16:
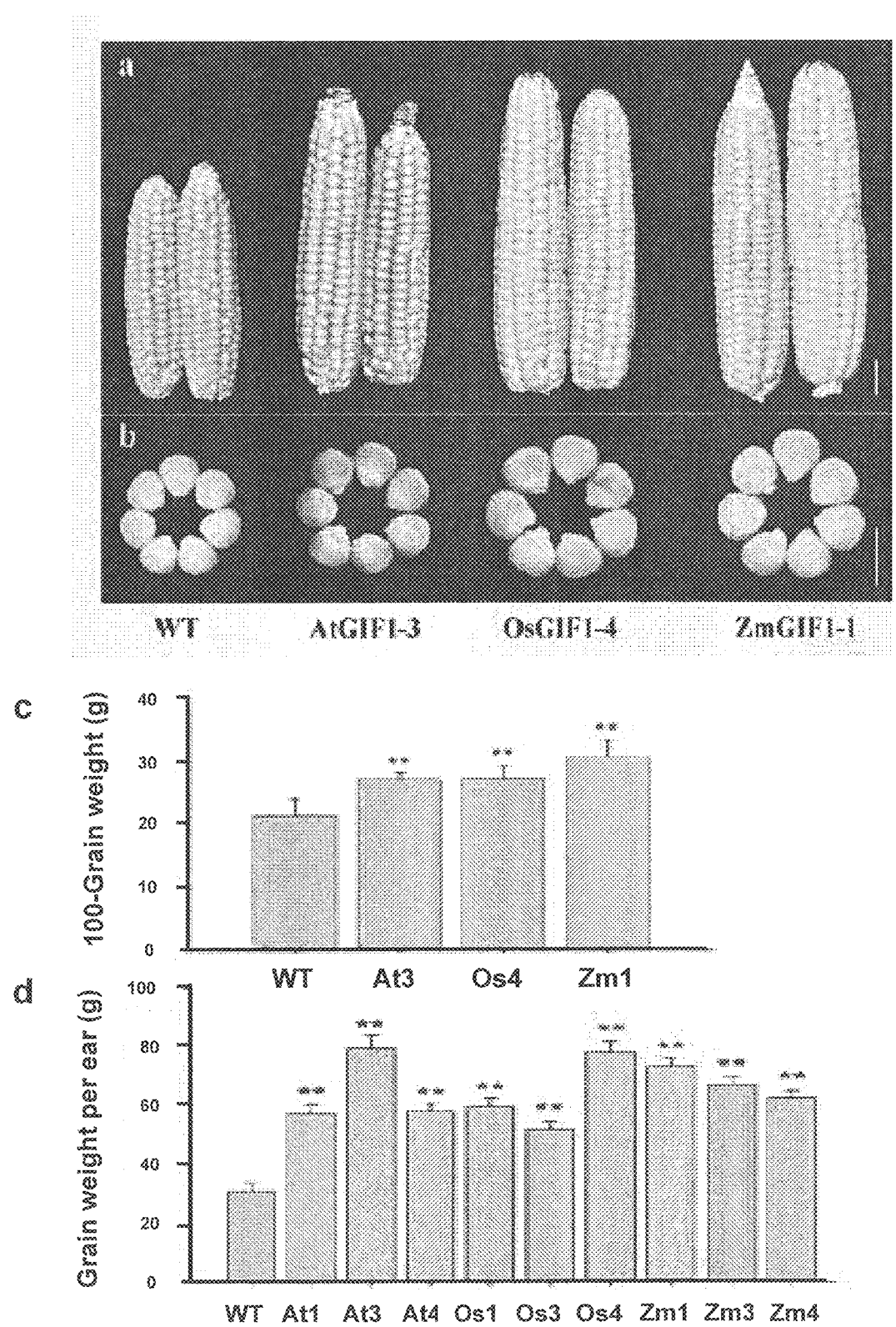

FIG. 16 shows Corn cobs, kernel and Grain weights of wild type Ye478 and transgenic lines ($T_4$) constitutively expressing AtGIF1, OsGIF1 or ZmGIF1. (a) Corn cobs of Ye478 and different transgenic lines. Scale bar=2 cm. (b) Kernels of Ye478 and different transgenic lines. Scale bar=1 cm). (c) One-hundred grain weights of Ye478 and different transgenic lines. (d) Ear grain weights of Ye478 and different transgenic lines. WT, wild type Ye478; At1, At3 and At4, transgenic lines AtGIF1-1, AtGIF1-3 and AtGIF1-4; Os1, Os3 and Os4, transgenic lines OstGIF1-1, OsGIF1-3 and OsGIF1-4; Zm1, Zm3 and Zm4, transgenic lines ZmGIF1-1, ZmGIF1-3 and ZmGIF1-4. Data are shown as means±s.e.m. Asterisks indicate a significant difference between transgenic and WT plants under the same conditions at *$0.01<P<0.05$ and **$P<0.01$ using the Student's t-test (n=3).

Figure 17:
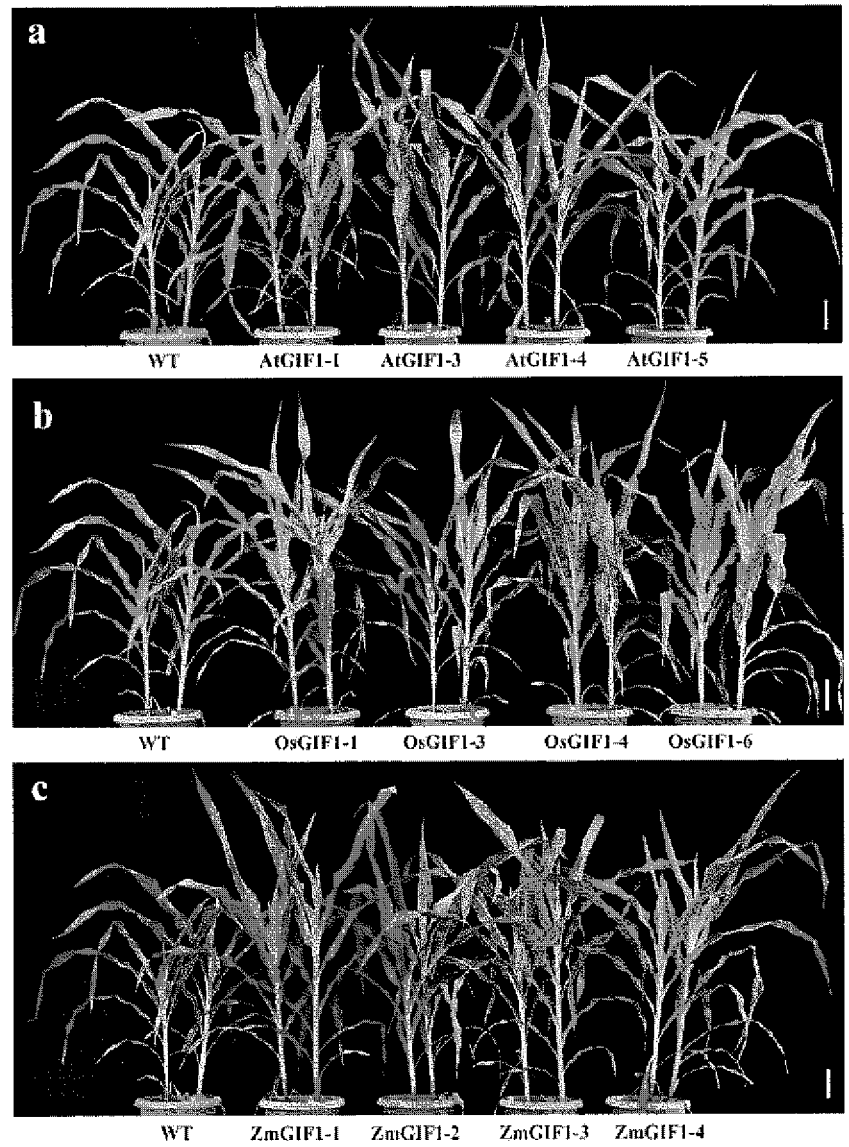

FIG. 17 shows Growth phenotypes of wild type Ye478 (WT) and transgenic lines ($T_4$) constitutively expressing AtGIF1, OsGIF1 and ZmGIF1. Scale bar=10 cm. Three-month-old plants at 13-leaf stage grown in the greenhouse are shown. (a) WT and different transgenic lines constitutively expressing AtGIF1. (b) WT and different transgenic lines constitutively expressing OsGIF1. (c) WT and different transgenic lines constitutively expressing ZmGIF1.

Figure 18:
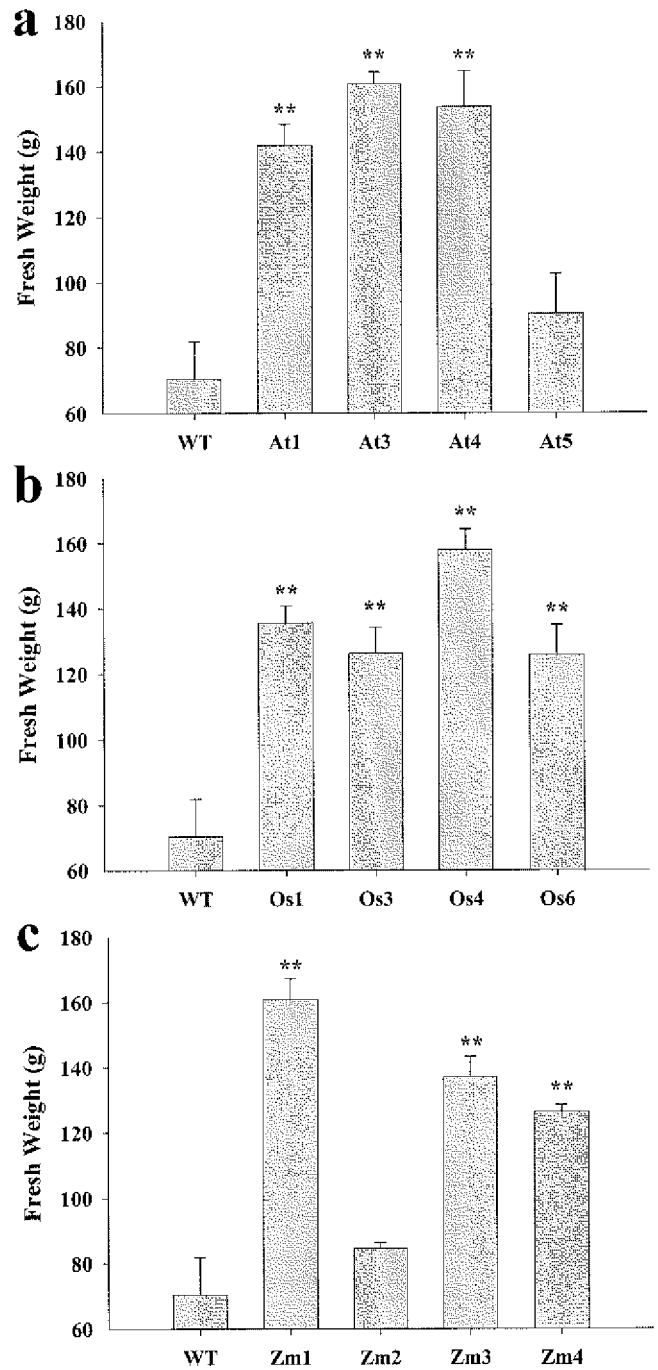

FIG. 18 shows Fresh weights of aerial parts of wild type Ye478 (WT) and transgenic lines ($T_4$) constitutively expressing AtGIF1, OsGIF1 and ZmGIF1. The aerial parts of three-month-old plants at 13-leaf stage grown in the greenhouse are harvested for biomass analyses. (a) WT and different transgenic lines constitutively expressing AtGIF1. (b) WT and different transgenic lines constitutively expressing OsGIF1. (c) WT and different transgenic lines constitutively expressing ZmGIF1. WT, wild type Ye478; At1, At3, At4 and At5, transgenic lines AtGIF1-1, AtGIF1-3, AtGIF1-4 and AtGIF1-5; Os1, Os3, Os4 and Os6, transgenic lines OstGIF1-1, OsGIF1-3, OsGIF1-4 and OsGIF1-6; Zm1, Zm2, Zm3 and Zm4, transgenic lines ZmGIF1-1, ZmGIF1-2, ZmGIF1-3 and ZmGIF1-4. Data are shown as means±s.e.m. Asterisks indicate a significant difference between transgenic and WT plants under the same conditions at **$P<0.01$ using the Student's t-test (n=3).

Figure 19:
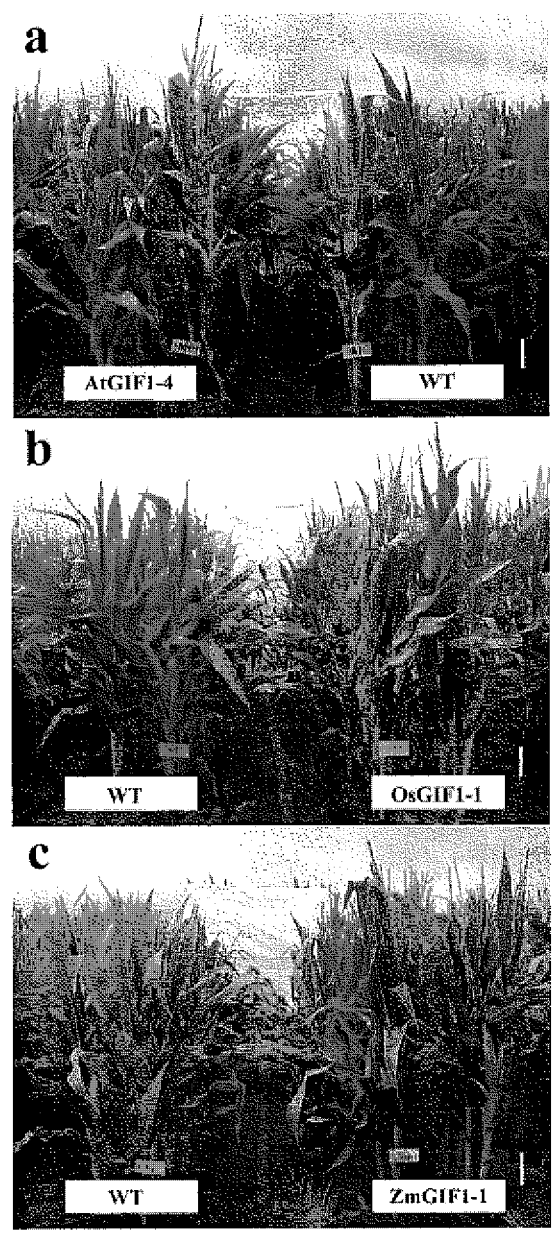

FIG. 19 shows Phenotypes of wild type Ye478 (WT) and transgenic lines ($T_4$) constitutively expressing AtGIF1, OsGIF1 or ZmGIF1 at flower stage grown on Nanbin Farm in Hainan province, China. Seeds were sown on Nov. 25, 2011. Scale bar=10 cm. (a) WT and transgenic line AtGIF1-4. (b) WT and transgenic line OsGIF1-1. (c) WT and transgenic line ZmGIF1-1.

Figure 20:
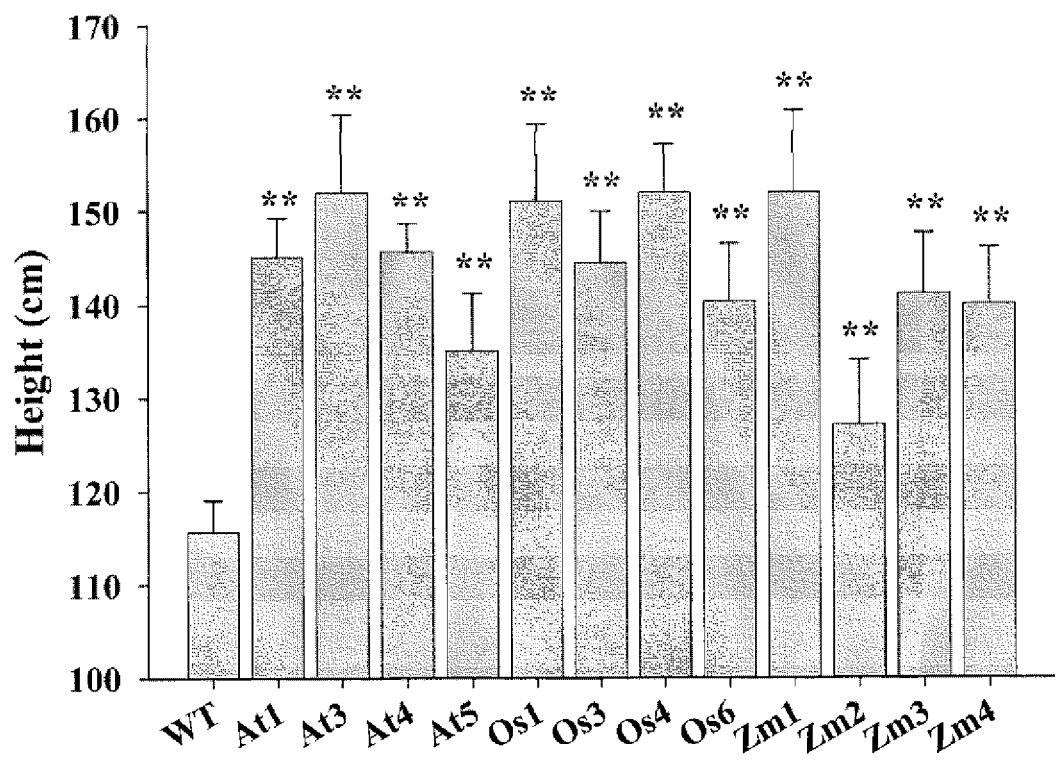

FIG. 20 shows Plant heights of wild type Ye478 (WT) and transgenic lines ($T_4$) constitutively expressing AtGIF1, OsGIF1 or ZmGIF1. Seeds were sown in Hainan province, China on Nov. 25, 2011. The aerial parts of shoots were harvested at maturity. WT, wild type Ye478; At1, At3, At4 and At5, trans genic lines AtGIF1-1, AtGIF1-3, AtGIF1-4 and AtGIF1-5; Os1, Os3, Os4 and Os6, transgenic lines OstGIF1-1, OsGIF1-3, OsGIF1-4 and OsGIF1-6; Zm1, Zm2, Zm3 and Zm4, transgenic lines ZmGIF1-1, ZmGIF1-2, ZmGIF1-3 and ZmGIF1-4. Data are shown as means±s.e.m. Asterisks indicate a significant difference between transgenic and WT plants under the same conditions at **$P<0.01$ using the Student's t-test (n=3).

Figure 21:
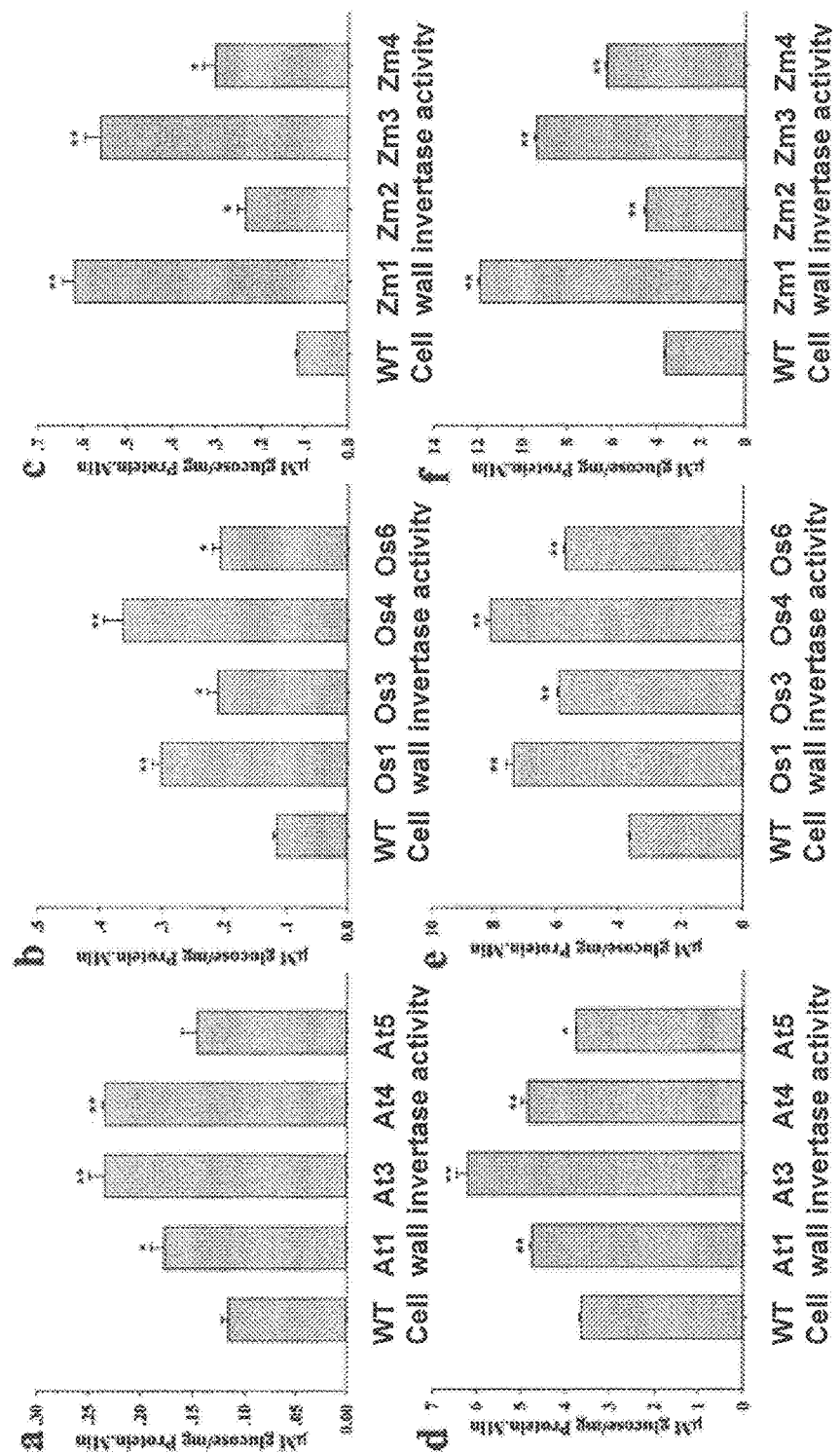

FIG. 21 shows Cell wall invertase activity analyses. Cell wall invertase activities in wild type Ye478 (WT) and different transgenic lines constitutively expressing AtGIF1, OsGIF1 or ZmGIF1 were measured. (a-c) Cell wall invertase activities in leaves of WT and transgenic ($T_3$) lines grown in the greenhouse at 13-leaf stage. (d-f) Cell wall invertase activities in seeds of field grown WT and transgenic ($T_4$) lines at 12 DAP. Data are shown as means±s.e.m. Asterisks indicate a significant difference between transgenic and WT plants under the same conditions at *$0.01<P<0.05$ and **$P<0.01$ using the Student's t-test (n=3). WT, wild type Ye478; At1, At3, At4 and At5, transgenic lines AtGIF1-1, AtGIF1-3, AtGIF1-4 and AtGIF1-5; Os1, Os3, Os4 and Os6, transgenic lines OstGIF1-1, OsGIF1-3, OsGIF1-4 and OsGIF1-6; Zm1, Zm2, Zm3 and Zm4, transgenic lines ZmGIF1-1, ZmGIF1-2, ZmGIF1-3 and ZmGIF1-4.

Figure 22:
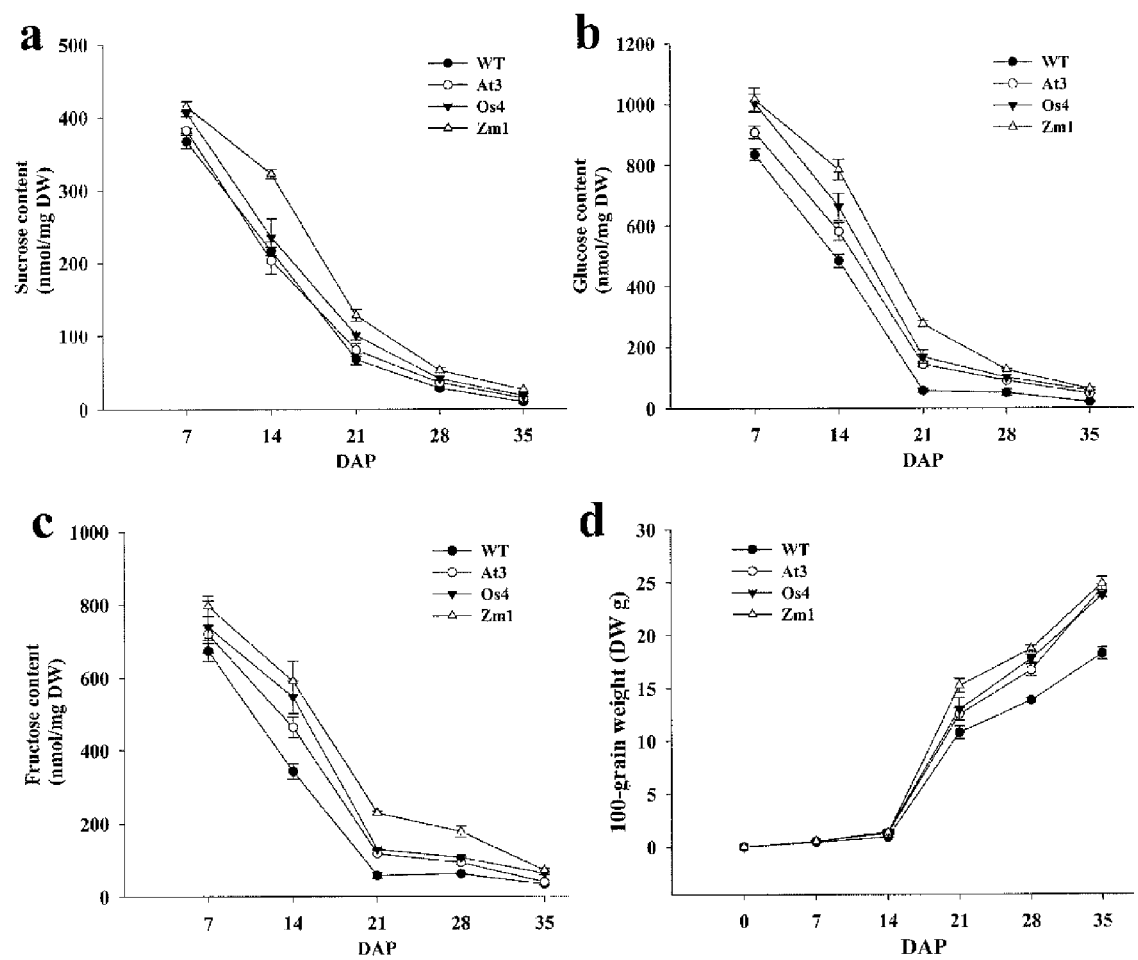

FIG. 22 shows Sugar content and grain-filling of wild type Ye478 (WT) and different transgenic lines constitutively expressing AtGIF1, OsGIF1 or ZmGIF1. Seeds of WT and different transgenic ($T_4$) lines were sown in November, 2011 on Nanbin Farm, Hainan province, China. Bars represent s.d. of three replications. (a-c) Glucose, fructose and sucrose contents of WT and transgenic kernels ($T_5$). (d) Grain-filling process (weight in grams of 100 dry kernels) of WT and transgenic maize ($T_5$). WT, wild type Ye478; At3, transgenic line AtGIF1-3; Os4, transgenic line OsGIF1-4; Zm1, transgenic line ZmGIF1-1.

Figure 23:
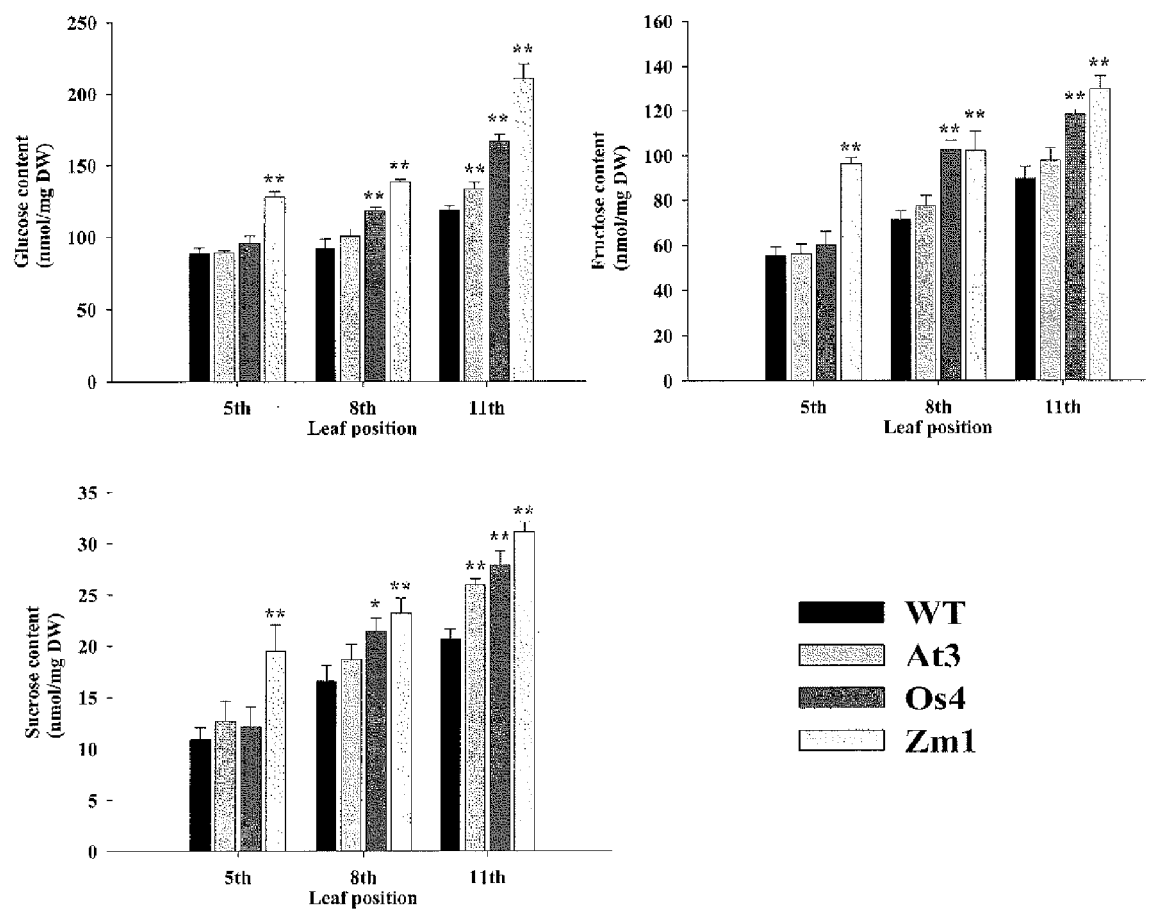

FIG. 23 shows Sugar content in leaves of wild type Ye478 (WT) and different transgenic lines constitutively expressing AtGIF1, OsGIF1 or ZmGIF1. WT and transgenic ($T_4$) lines were grown in the greenhouse and sugar contents in leaves at different positions were measured. WT, wild-type Ye478; At3, transgenic line AtGIF1-3; Os4, transgenic line OsGIF1-4; Zm1, transgenic line ZmGIF1-1. Data are shown as means±s.e.m. Asterisks indicate a significant difference between transgenic and WT plants under the same conditions at *$0.01<P<0.05$ and **$P<0.01$ using the Student's t-test (n=3).

Figure 24:
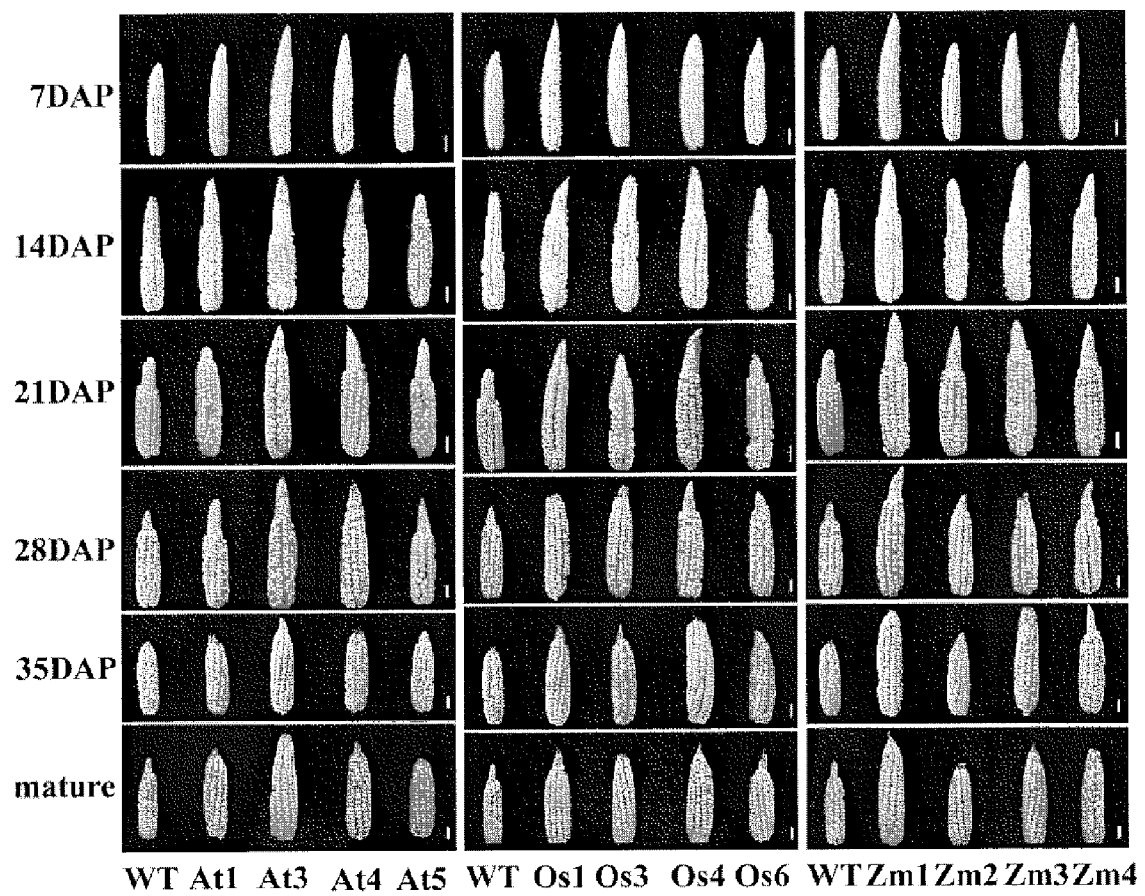

FIG. 24 shows Corn cobs size comparisons of wild type Ye478 (WT) and different transgenic lines ($T_5$) constitutively expressing AtGIF1, OsGIF1 or ZmGIF1. Seeds of WT and different transgenic ($T_4$) lines were sown on Nov. 25, 2011 on Nanbin Farm, Hainan province, China. Cobs at different growth stages were shown. WT, wild type Ye478; At1, At3, At4 and At5, transgenic lines AtGIF1-1, AtGIF1-3, AtGIF1-4 and AtGIF1-5; Os1, Os3, Os4 and Os6, transgenic lines OstGIF1-1, OsGIF1-3, OsGIF1-4 and OsGIF1-6; Zm1, Zm2, Zm3 and Zm4, transgenic lines ZmGIF1-1, ZmGIF1-2, ZmGIF1-3 and ZmGIF1-4. Scale bar=2 cm.

Figure 25:
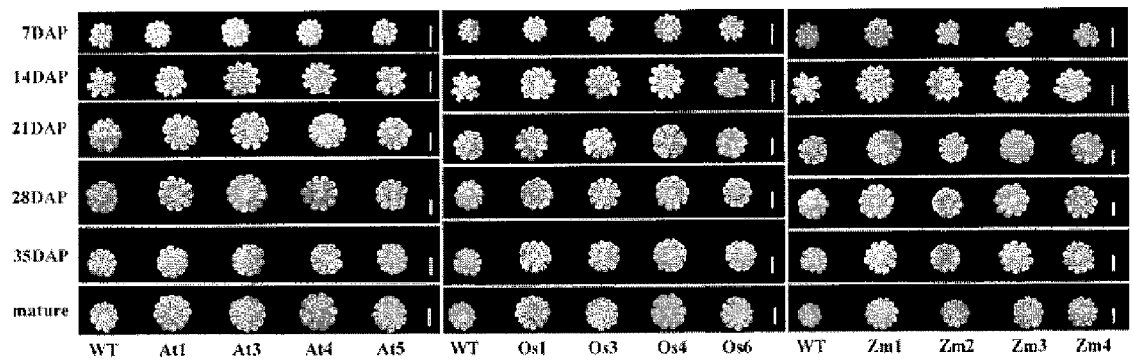

FIG. 25 shows Cross-section views of corn cobs of wild type Ye478 (WT) and different transgenic lines ($T_5$) constitutively expressing AtGIF1, OsGIF1 or ZmGIF1. Seeds of WT and different transgenic ($T_4$) lines were sown on Nov. 25, 2011 on Nanbin Farm, Hainan province, China. Cross-sections of corn cobs at different growth stages were shown. WT, wild type Ye478; At1, At3, At4 and At5, transgenic lines AtGIF1-1, AtGIF1-3, AtGIF1-4 and AtGIF1-5; Os1, Os3, Os4 and Os6, transgenic lines OstGIF1-1, OsGIF1-3, OsGIF1-4 and OsGIF1-6; Zm1, Zm2, Zm3 and Zm4, transgenic lines ZmGIF1-1, ZmGIF1-2, ZmGIF1-3 and ZmGIF1-4. Scale bar=2 cm.

Figure 26:
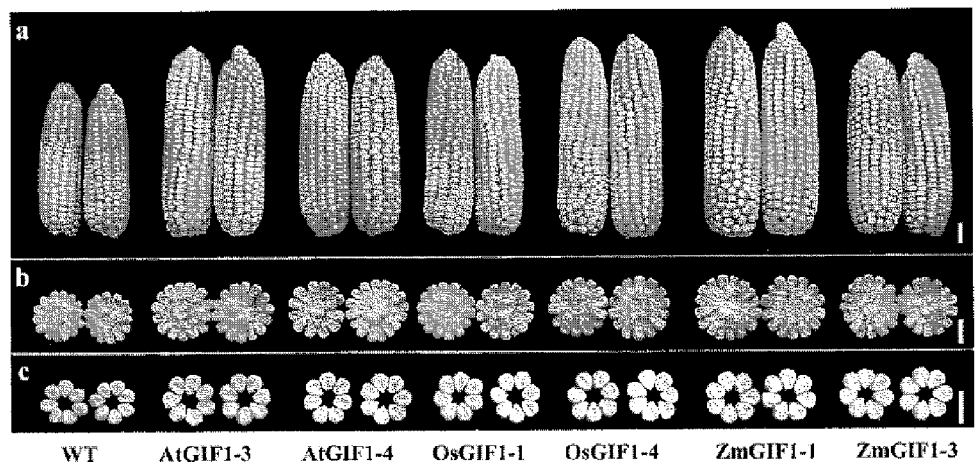

FIG. 26 shows Corn cob and kernel of wild type Ye478 and transgenic lines ($T_6$) constitutively expressing AtGIF1, OsGIF1 or ZmGIF1. (a) Corn cobs of Ye478 and different transgenic lines. (b) Kernels of Ye478 and different transgenic lines. WT, wild type Ye478; At3 and At4, transgenic lines AtGIF1-3 and AtGIF1-4; Os1 and Os4, transgenic lines OstGIF1-1 and OsGIF1-4; Zm1 and Zm3, transgenic lines ZmGIF1-1 and ZmGIF1-3. Scale bar=2 cm.

Figure 27:
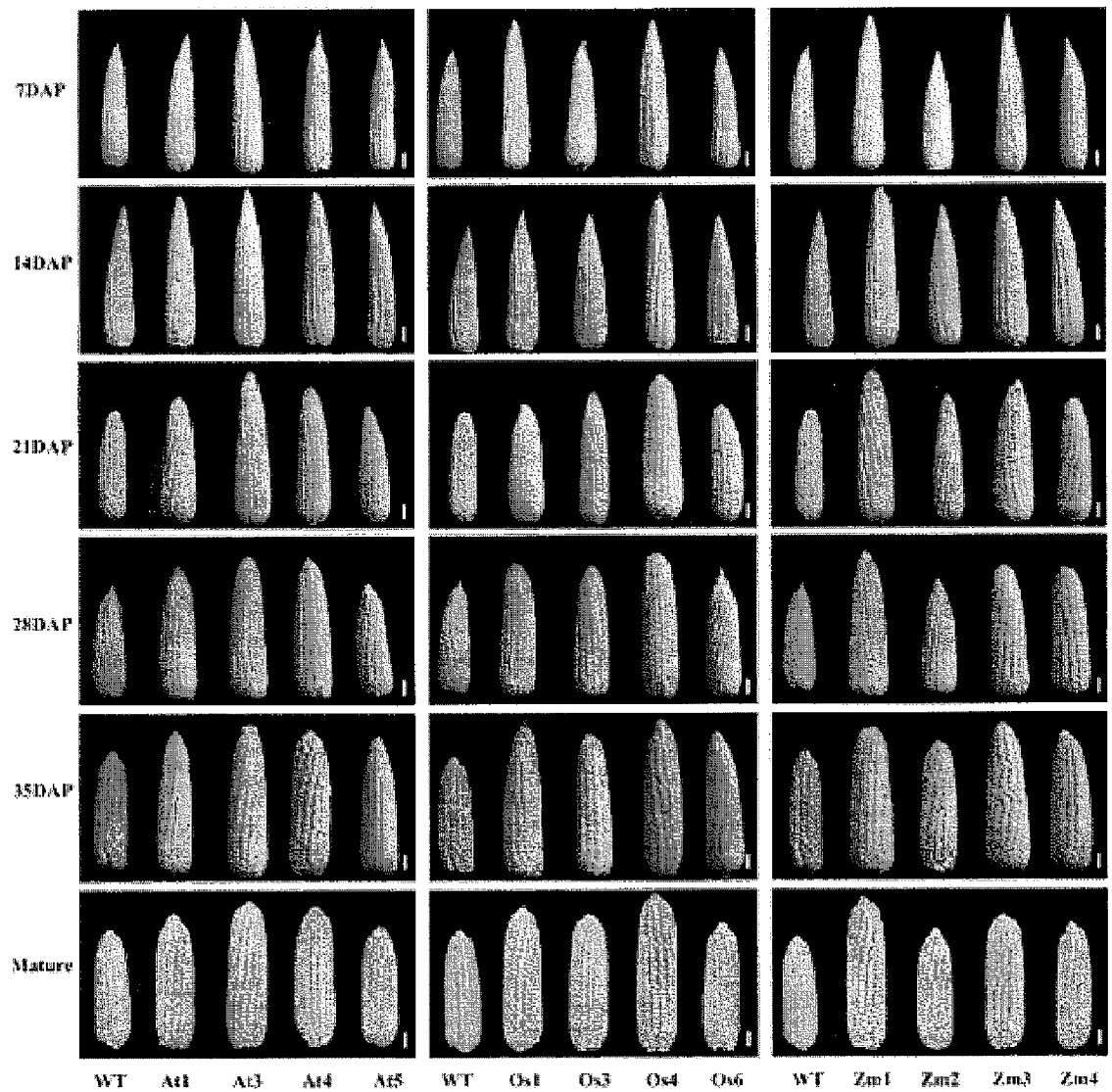

FIG. 27 shows Corn cobs size comparisons of wild type Ye478 (WT) and different transgenic lines ($T_6$) constitutively expressing AtGIF1, OsGIF1 or ZmGIF1. Seeds of WT and different transgenic ($T_4$) lines were sown in June, 2012 in Zhangye, Gansu province, China. Cobs at different growth stages were shown. WT, wild type Ye478; At1, At3, At4 and At5, transgenic lines AtGIF1-1, AtGIF1-3, AtGIF1-4 and AtGIF1-5; Os1, Os3, Os4 and Os6, transgenic lines OstGIF1-1, OsGIF1-3, OsGIF1-4 and OsGIF1-6; Zm1, Zm2, Zm3 and Zm4, transgenic lines ZmGIF1-1, ZmGIF1-2, ZmGIF1-3 and ZmGIF1-4. Scale bar=2 cm.

Figure 28:
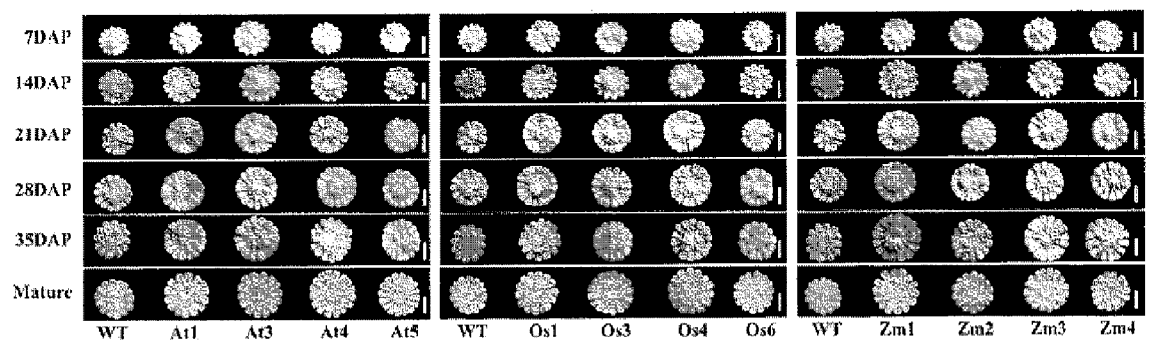

FIG. 28 shows Cross-section views of corn cobs of wild type Ye478 (WT) and different transgenic lines ($T_6$) constitutively expressing AtGIF1, OsGIF1 or ZmGIF1. Seeds of WT and different transgenic ($T_4$) lines were sown in June, 2012 in Zhangye, Gansu province, China. Cross-sections of corn cobs at different growth stages were shown. WT, wild type Ye478; At1, At3, At4 and At5, transgenic lines AtGIF1-1, AtGIF1-3, AtGIF1-4 and AtGIF1-5; Os1, Os3, Os4 and Os6, transgenic lines OstGIF1-1, OsGIF1-3, OsGIF1-4 and OsGIF1-6; Zm1, Zm2, Zm3 and Zm4, transgenic lines ZmGIF1-1, ZmGIF1-2, ZmGIF1-3 and ZmGIF1-4. Scale bar 2 cm.

Figure 29:
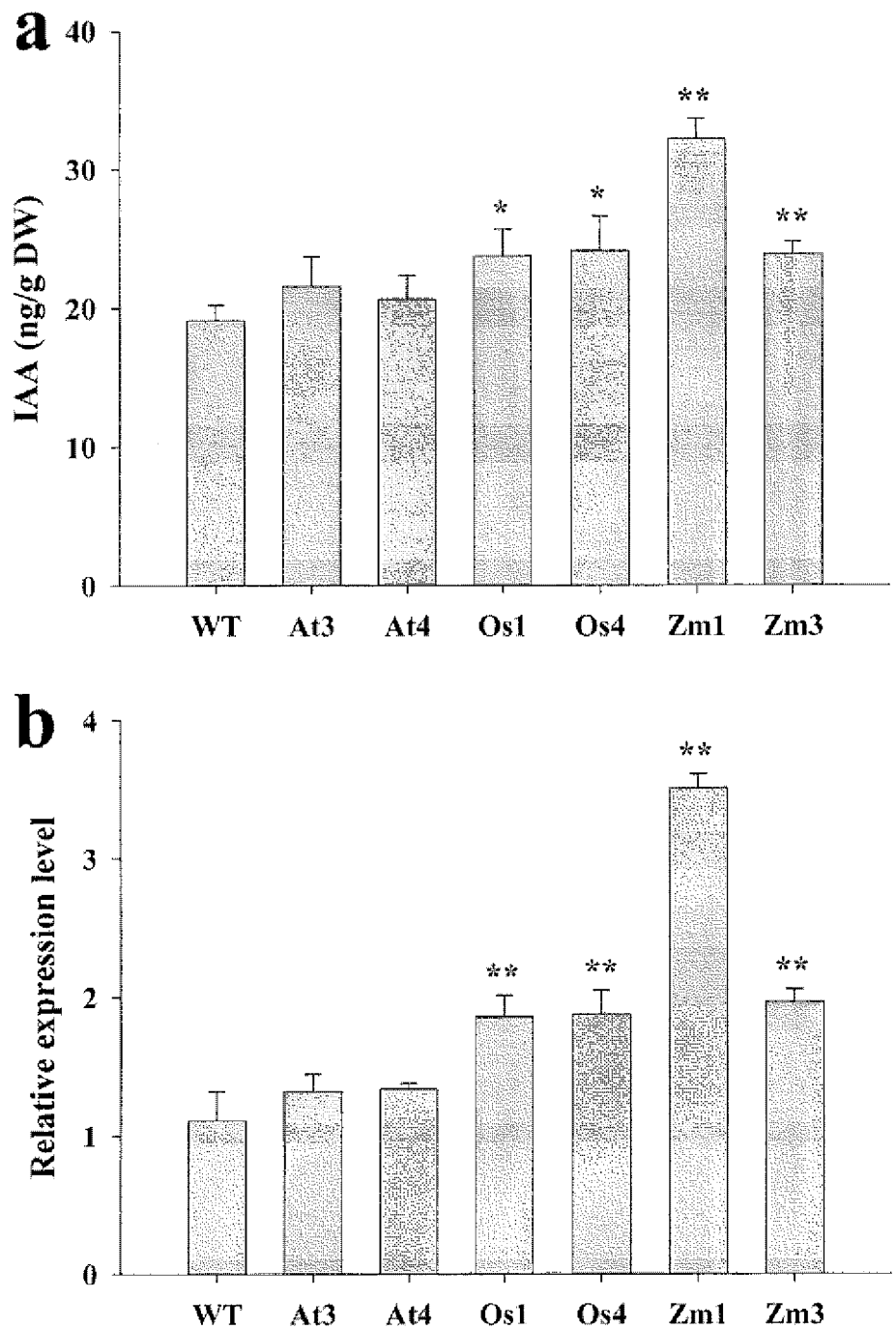

FIG. 29 shows IAA content and real time PCR analyses. Wild type Ye478 (WT) and different transgenic ($T_4$) lines constitutively expressing AtGIF1, OsGIF1 or ZmGIF1 were grown in the greenhouse. The top two leaves from 13-leaf stage plants were used for the analyses. (a) IAA content. (b) Relative expression level ($2^{-\Delta\Delta Ct}$) of putative IAA biosynthetic gene ZmTAR1. Data are shown as means±s.e.m. Asterisks indicate a significant difference between transgenic and WT plants under the same conditions at *0.01<P<0.05 and **P<0.01 using the Student's t-test (n=3).

Figure 30:
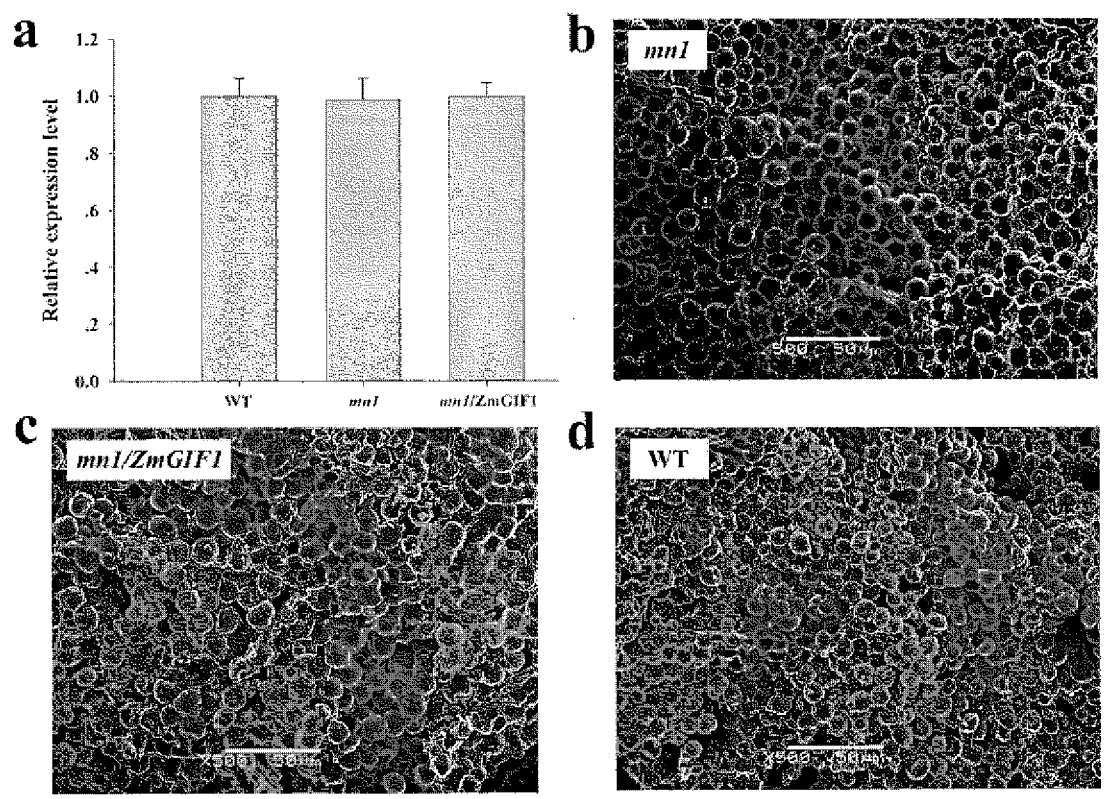

FIG. 30 shows Real time PCR and scanning electron microscope analyses. (a) Quantitative real-time PCR analyses of the putative IAA biosynthetic gene ZmTAR1 transcript levels ($2^{-\Delta\Delta Ct}$). Total RNA was extracted from leaves of W22, mn1 and its complementary line mn1/ZmGIF1 ($T_2$) plants grown in the greenhouse at five-leaf stage. Real-time PCR analyses were performed with ZmTAR1 gene specific primers. The relative expression of ZmTAR1 gene was double-normalized using the housekeeping gene Actin1. Data represents the average of three independent experiments±SD. (b-d) Scanning electron microscope observation. Mature dry seeds were used. Magnification, ×500. Scale bar=50 µm. WT, Wildtype W22; mn1, mn1 mutant; mn1/ZmGIF1, mn1 transgenic line complemented with ZmGIF1 driven by its own promoter ($T_3$).

Figure 31:
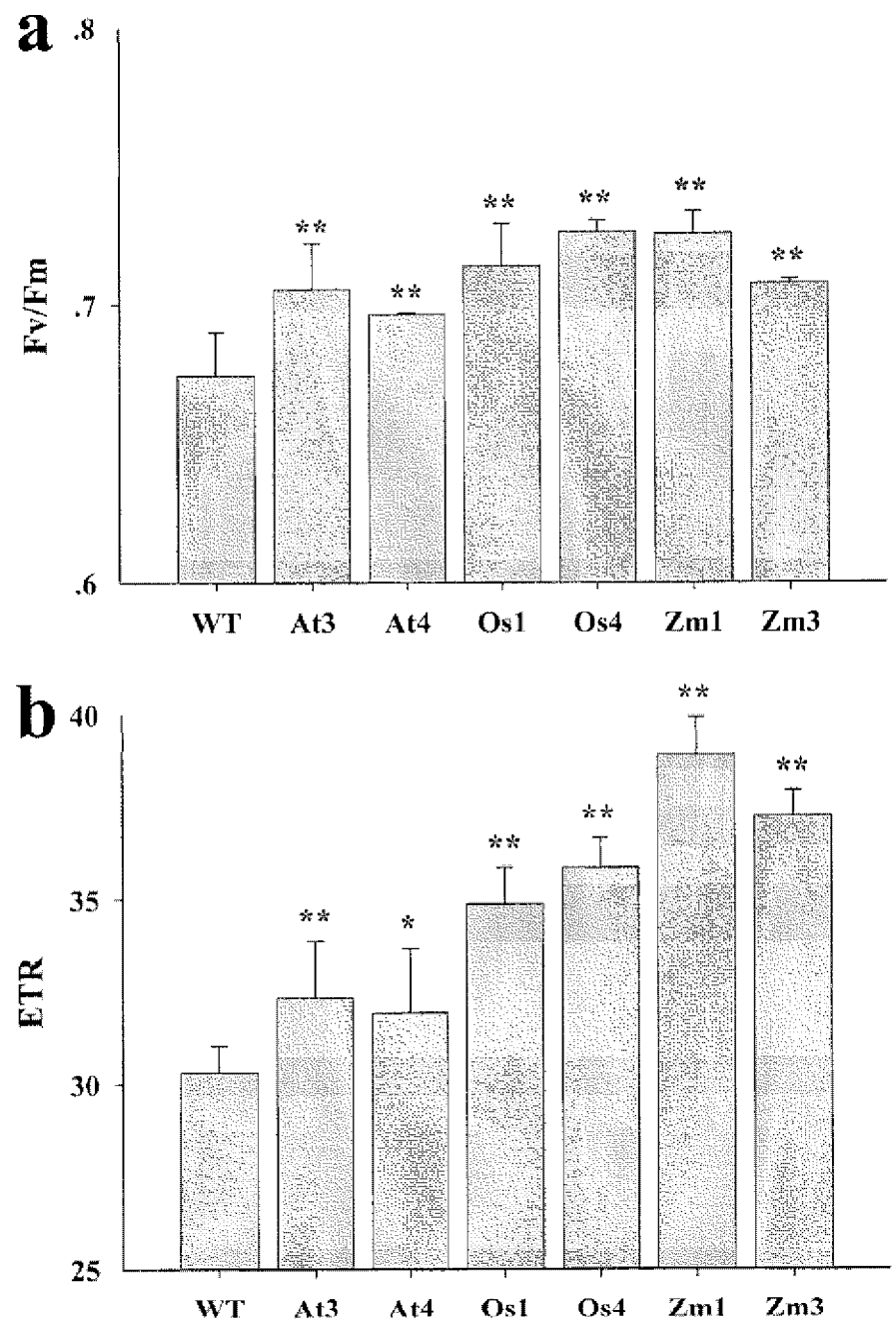

FIG. 31 shows Maximum quantum efficiency (Fv/Fm) and photosynthetic electron transport rate (ETR) analyses. Wild type Ye478 (WT) and different transgenic ($T_4$) lines constitutively expressing AtGIF1, OsGIF1 or ZmGIF1 were grown in the greenhouse to the 13-leaf stage. Photosynthesis activities were measured on the 10th fully-expanded leaves using Junior-PAM after a 5 min dark adaptation. Data are shown as means±s.e.m. Asterisks indicate a significant difference between transgenic and WT plants under the same conditions at *0.01<P<0.05 and **P<0.01 using the Student's t-test (n=3). (a) Fv/Fm. (b) ETR.

Figure 32:
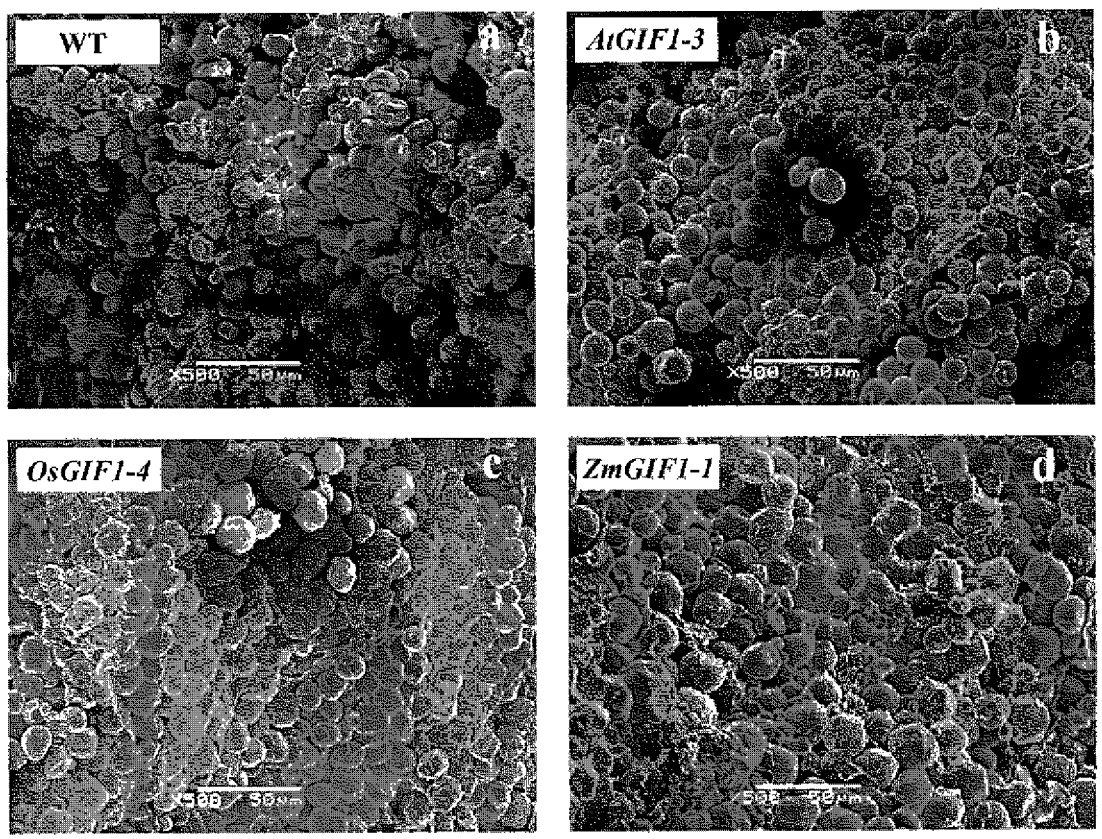

FIG. 32 shows Scanning electron microscope analyses. Mature seeds of wild type Ye478 and transgenic lines ($T_4$) constitutively expressing AtGIF1, OsGIF1 and ZmGIF1 were used for scanning electron microscope observation. Magnification, ×500. Scale bar=50 µm. (a) Wild type Ye478. (b) AtGIF1-3. (c) OsGIF1-4. (d) ZmGIF1-1.

Figure 33:
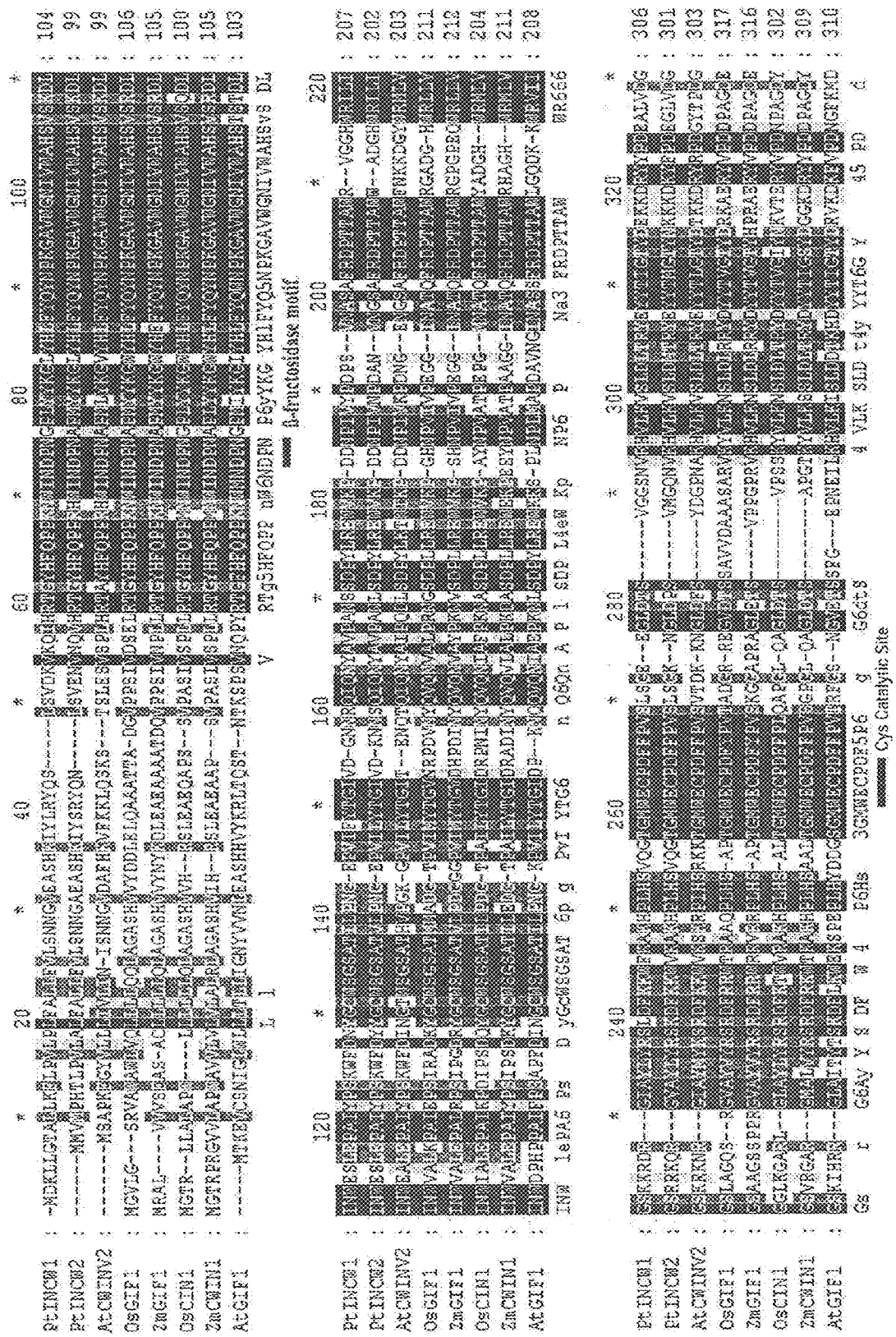

FIG. 33 shows Sequence alignments of GIF1 with homologous proteins from different plants. The BLAST search program (http://www.ncbi.nlm.nih.gov/BLAST/) was used to look for invertase sequences homologous to GIF1. The highest homologous invertase sequences were aligned using a GENEDOC software. The aligned invertases include the functionally known OsGIF1 (rice ADE60571.1), OsCIN1 (rice ADE60654.1), PtINCW1 (PaxgINV1 ABY81288.1), PtINCW2 (PaxgINV2 ABY81289.1) and ZmCWIN1 (maize AAD02511.1), ZmGIF1 (also known as Mn1; NM_001112126), and functionally unknown invertases ATCWINV2 (*Arabidopsis* NP_190828.2) and AtGIF1 (*Arabidopsis* NP_566464.1). The β-fructosidase motif, the Cys catalysis site, and the conserved glycosylation motif are indicated.

DETAILED DESCRIPTION

Embodiments of the invention relate to grain incomplete filling 1 (GIF1) proteins and genes and their uses in improving grain filling, seed sizes, and grain yields in crops. GIF1 genes encode cell wall invertases in various plants. Embodiments of the invention, for example, relate to the use of GIF1 proteins from *Arabidopsis* (AtGIF1, or ATCWINV1), rice (OsGIF1, or OsCIN2) and maize (ZmGIF1, ZmCWINV2; also know as Mn1) in the improvement of grain fillings, seed sizes and grain yields of these plants and similar crops.

In most agriculturally important plants, carbohydrate is distributed through the sieve element system to the sink organs in the form of sucrose, the end product of photosynthesis in source organs. In the sink organs, sucrose is cleaved, by invertase or sucrose synthetase, to monomers that are used to synthesize carbohydrate polymers (e.g., starch), which are the storage forms of photosynthesis products.

The inventors of the present invention discovered that GIF1 genes can control crop grain fillings. Non-expression or lowered expression of these genes would significantly interfere with crop grain fillings, reduce seed weights, and crop yields. Comparatively, enhanced expression of these genes could facilitate crop grain fillings and increase seed weights and crop yields. These genes were cloned and named GIF1 genes (Grain Incomplete Filling 1). Investigations confirmed that normal expression of GIF1 in wild-type plants led to normal growth of crop grains, while mutation of GIF1 causing non-expression of the GIF1 proteins would result in poor crop qualities, low seed vigor, and poor resistance towards storage diseases. Importantly, these features were notably improved in transgenic crops with enhanced expression of GIF1 proteins. Based on the aforementioned findings, the current invention has been completed.

As used herein, "crop" refers to, but not limited to, Graminae, Brassicaceae (*Cruciferae*), Fabaceae (Leguminosae), Malvaceae, Chenopodiacea, Asteraceae, Myyrtaceae, Salicaceae, and xylophyta, and the like. Preferably, crops includes, but not limited to, rice, wheat, barley, maize, broomcorn, soybean, cotton, canola, sugar beet, alfalfa, rye, sorghum, sugarcane, sunflower, oilseed rape (rapeseed), vegetables, Eucalyptus, poplar, etc.

As used herein, the term "isolated" refers to a substance which has been isolated from the original environment. For naturally occurring substance, the original environment is the natural environment. e.g., the polynucleotide and polypeptide in a naturally occurring state in the viable cells are not isolated or purified. However, if the same polynucleotide and polypeptide have been isolated from other components naturally accompanying them, they are isolated or purified.

As used herein, "GIF1" refers to grain incomplete filling 1. Analogs of these genes are found in common crops. "GIF1 gene" and "GIF1 protein" refer to the corresponding gene and protein, respectively. They may be referred to as "GIF1" without regard to the source. Alternatively, they may be referred to as, for example, AtGIF1, OsGIF1, or ZmGIF1, based on their sources from *Arabidopsis thaliana, Oryza sativa* (rice), and *Zea mays* (maize), respectively.

As used herein, "isolated GIF1 protein" or "isolated GIF1 polypeptide" refers to an GIF1 protein that does not exist in the natural environment, which includes a completely purified GIF1 protein. Substantively purified GIF1 protein contains almost no naturally relevant proteins, lipids, saccharides, or other substances. The GIF1 proteins could be purified by those skilled in the art using standard protein purification techniques. A purified polypeptide forms a single main band on a non-reductive PAGE gel.

Polypeptides of the present invention can be recombinant polypeptides, natural polypeptides, or synthetic polypeptides, preferably recombinant polypeptides. Polypeptides of the present invention may be purified natural products or chemically synthetic products. Alternatively, they may be produced from prokaryotic or eukaryotic hosts, such as bacteria, yeast, higher plant, insect, and mammalian cells, using recombinant techniques. According to the hosts used in the recombinant production, the polypeptides may be glycosylated or non-glycosylated. Polypeptides of the present invention could bear or not bear the initial methionine residues.

The invention further comprises fragments, derivatives or analogues of GIF1. As used herein, the term "fragment," "derivative" or "analogue" mean a polypeptide that essentially retains the same biological functions or activity of GIF1 protein. Based on the following descriptions and examples, one having ordinary skill in the art could easily determine whether the polypeptides have the same biological functions or activities as the GIF1 proteins. A polypeptide fragment, derivative or analogue of the present invention could be (i) a polypeptide with one or more amino acid residues deleted or inserted, or one or more conserved or non-conserved amino acid residue (preferably conserved amino acid residue) being substituted, wherein the substituted amino acid residues could be encoded or not encoded by the genetic codes; or (ii) a polypeptide with one or more amino acid residues including substituted groups; or (iii) one in which a mature polypeptide is fused with another compound, such as a compound to increase the half-life of the polypeptide (for example, polyethylene glycol), or (iv) one in which the additional amino acids, such as a leader or secretary sequence or a sequence used for purifying polypeptide or pro-protein, are fused to the polypeptide. Such fragments, derivatives and analogs are known to the artisans based on the teachings herein.

As used herein, the term "OsGIF1 protein" refers to a polypeptide with the amino acid sequence of SEQ ID NO: 2 and OsGIF1 protein activity. The term "AtGIF1 protein" refers to a polypeptide with the amino acid sequence of SEQ ID NO: 7 and AtGIF1 protein activity. the term "ZmGIF1 protein" refers to a polypeptide with the amino acid sequence of SEQ ID NO: 10 and ZmGIF1 protein activity. The terms also comprise the variants which have the same functions of these GIF1 proteins and have the amino acid sequences of SEQ ID NO: 2, SEQ ID NO: 7, or SEQ ID NO: 10. The variants include, but are not limited to, deletions, insertions and/or substitutions of one or more (typically 1-200, preferably 1-180, preferably 1-150, preferably 1-120, preferably 1-100, preferably 1-80, preferably 1-50, preferably 1-30, more preferably 1-20, most preferably 1-10, still more preferably 1-8 or 1-5) amino acids, and addition of one or more (typically less than 50, preferably, less than 20, preferably less than 10, more preferably less than 5) amino acids at the C-terminal and/or N-terminal. For example, protein functions are usually unaltered when substituted with amino acids of similar or analogous characteristics. Furthermore, protein functions are usually unaltered following addition of one or more amino acids at the C-terminal and/or N-terminal. The term "GIF1 protein" also includes an active fragment and active derivative of a GIF1 protein.

The variants of a polypeptide include homologous sequences, conservative mutants, allelic variants, natural mutants, induced mutants, proteins encoded by a polynucleotide that hybridizes to GIF1 DNA under high or low stringency conditions, as well as the polypeptides retrieved by antisera raised against GIF1 polypeptide. The invention also provides other polypeptides, e.g. a fusion protein containing a GIF1 protein or a fragment thereof. Apart from the substantially full-length polypeptide, embodiments of the invention also include soluble fragments of GIF1 proteins. Usually, such fragments comprise at least about 20, typically at lease about 30, preferably at least about 50, more preferably at least about 80, and most preferably about 100 continuous amino acids of a GIF1 sequence.

The invention also provides analogues of GIF1 proteins or polypeptides. Difference between the analogues and natural GIF1 proteins could be in the amino acid sequences, the modification modes which do not affect the sequences, or by both. These polypeptides include natural or induced genetic variants. Induced variants could be prepared by various techniques including random mutagenesis induced by irradiation or exposure to mutagens, site-directed mutagenesis or other known molecular biology techniques. Analogues may also include amino acids different from the natural L-amino acid residues (e.g. D-amino acid), or unnatural or synthetic amino acids (e.g. β-, γ-amino acid). It should be understood that polypeptides in the invention are not limited to the aforementioned typical polypeptides.

Modifications (usually the primary structure being unaltered) may include in vivo or in vitro chemical derivatives of the polypeptides, such as acetylation or carboxylation. Modifications may also include glycosylation. Modification may also include phosphorylated amino acid residues (e.g. phosphotyrosine, phosphoserine, and phosphothreonine). It may also include modified polypeptides with improved resistance to proteolytic hydrolysis and optimized solubility.

In the invention, a "conserved variant of GIF1 protein" refers to a polypeptide with at most 50, preferably at most 20, preferably at most 10, more preferably at most 5, most preferably at most 3 amino acids being substituted with amino acids having substantially the same or similar properties. These conserved variants are preferably obtained according to the amino acid substitutions listed in Table 1.

TABLE 1

| Amino acid residue | Typical substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |

TABLE 1-continued

| Amino acid residue | Typical substitution | Preferred substitution |
|---|---|---|
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The invention also provides polynucleotide sequences that encode the GIF1 proteins of the present invention or the conserved variants thereof.

The polynucleotides may be in the form of DNA or RNA. DNA may include cDNA, genomic DNA or synthetic DNA. DNA may be single-stranded or double-stranded. DNA may be a coding strand or a non-coding strand. Sequence of the coding region that encodes mature polypeptide of OsGIF1 may be the same as in ID NO: 1 or SEQ ID NO: 3, or is a degenerate variant thereof. As used herein, a "degenerate variant" of OsGIF1 refers to a nucleic acid sequence encoding a protein of SEQ ID NO: 2, but contains a coding region that is different from the coding region shown in SEQ ID NO: 1 or SEQ ID NO: 3.

Sequence of the coding region that encodes mature polypeptide of AtGIF1 may be the same as in ID NO: 6 or SEQ ID NO: 8, or is a degenerate variant thereof. As used herein, a "degenerate variant" of AtGIF1 refers to a nucleic acid sequence encoding a protein of SEQ ID NO: 7, contains a coding region that is different from the coding region as shown in SEQ ID NO: 6 or SEQ ID NO: 8.

Sequence of the coding region that encodes mature polypeptide of ZmGIF1 may be the same as in ID NO: 9 or SEQ ID NO: 11, or is a degenerate variant thereof. As used herein, a "degenerate variant" of ZmGIF1 refers to a nucleic acid sequence encoding a protein of SEQ ID NO: 10, contains a coding region that is different from the coding region as shown in SEQ ID NO: 9 or SEQ ID NO: 11.

Polynucleotides encoding the polypeptides of SEQ ID NO:2, SEQ ID NO:7, or SEQ ID NO:10 may include those encoding the mature polypeptides, those encoding mature polypeptides and various additional encoding sequences, those encoding mature polypeptides (and optional additional encoding sequences) and non-encoding sequences.

The term a "polynucleotide encoding a polypeptide" may be a polynucleotide that encodes the polypeptide. It may also include polynucleotide with an additional encoding sequence and/or non-encoding sequence.

The invention also relates to the variants of the aforementioned polynucleotides, encoding the polypeptides having the same amino acid sequences as described herein, or their fragments, analogues, and derivatives. The variants of the polynucleotides may be naturally occurring allelic variants or non-naturally occurring variants. Such nucleotide variants may include substitution variants, deletion variants, and/or insertion variants. As known in the art, an allelic variant is a substituted form of a polynucleotide, within which one or more nucleotides may be substituted, deleted and/or inserted without substantially altering the function of the encoded polypeptide.

The invention also relates to polynucleotides that may hybridize with the aforementioned sequences, wherein the two sequences have a sequence identity of at least 50%, preferably at least 60%, preferably at least 65%, preferably at least 70%, more preferably at least 75%, more preferably at least 80%, and more preferably at least 90%, most preferably at least 95%. The invention specifically relates to polynucleotides that may hybridize with the polynucleotides of the invention under stringent conditions. "Stringent conditions" as used herein refers to (1) hybridization and elution at relatively low ionic strength and high temperature, such as 0.2× SSC, 0.1% SDS, and 60° C.; or (2) hybridization in the presence of denaturant, such as 50% (v/v) formamide, 0.1% calf serum/0.1% Ficoll, 42° C., etc; or (3) hybridization only when sequence identity between the two sequences was at least above 85%, preferably above 90%, preferably above 95%. In addition, the hybridizable polynucleotides encoded polypeptides share the same biological functions and activities as the mature polypeptides.

The invention also relates to nucleic acid fragments that may hybridize with the aforementioned sequences. As used herein, the length of a "nucleic acid fragment" is at least 15 nucleotides, preferably at least 30 nucleotides, more preferably at least 50 nucleotides, most preferably at least 100 nucleotides. The nucleic acid fragments can be used in amplifying techniques of nucleic acids (e.g. PCR) to determine and/or isolate the GIF1 protein-encoding polynucleotides.

It should be understood that although the GIF1 genes in the invention are obtained from rice, maize, Arabidopsis, and the like, genes from other crops having high homology (e.g. above 50%, such as above 60%, 70%, 80%, 85%, 90%, even 95% sequence identity) with these GIF1 genes are also included within the scope of the invention. Methods and tools for identifying the sequence homology are known in the art, such as BLAST. Following the discovery of these GIF1 genes, the inventors also succeeded in discovering highly homologous genes in other crops such as AF030420 gene in wheat, AJ534447 gene in barley, and X69321 gene in carrot, using BLAST. The applications of these highly homologous genes in crop grain filling, sugar metabolic regulation and accumulation, and crop improvement are also included within the protected scope of the invention.

Full-length sequences of the GIF1 nucleotides or their fragments can be prepared by PCR amplifications, recombinations or synthetic methods. For PCR amplification, one can obtain said sequences by designing primers based on the nucleotide sequences disclosed herein, especially the ORF, and using cDNA library commercially available or prepared by routine techniques in the art as templates. When the sequences are long, it is usually necessary to perform two or more PCR amplifications and link the amplified fragments together correctly.

Once the sequences are obtained, one can produce lots of the sequences by recombinant methods. Usually, said sequences may be cloned into vectors which may be then transformed into host cells. The sequences may be isolated from the amplified host cells using conventional techniques.

Further, the sequences can be synthesized, especially when the fragments are short. Typically, several small fragments may be synthesized and linked together to obtain a long sequence.

It is completely feasible to chemically synthesize the DNA sequences encoding the protein of invention, or the fragments or derivatives thereof. The DNA sequence can thereafter be introduced into various available DNA molecules (or vectors) and cells in the art. In addition, mutations can be introduced into the protein sequences by chemical synthesis.

This invention also relates to vectors containing the polynucleotides of the invention, the host cells obtained from the vectors or GIF1 encoding sequences of the invention via genetic engineering, and the methods for obtaining the polypeptides of the invention using recombinant techniques.

Using conventional DNA recombinant techniques (Science, 1984; 224:1431), the polynucleotide sequences of the invention can be used to express or produce recombinant GIF1 proteins. Generally, it comprises the following steps:

(1) transfecting or transforming appropriate host cells with a polynucleotide (or a variant) encoding GIF1 polypeptide or a vector containing the polynucleotide;
(2) culturing the host cells in an appropriate medium;
(3) isolating or purifying the protein from the medium or cells.

The GIF1 polynucleotide sequences in the invention can be inserted into recombinant expression vectors. The term "recombinant expression vector" refers to a bacterium plasmid, phage, yeast plasmid, virus of plant cell, virus of mammalian cell or other vectors known in the art. Any plasmid or vector can be used as long as it is capable of replicating and is stable in the host. As an important characteristic, an expression vector usually contains an origin of replication, promoter, a marker gene and a translation regulation element.

Methods known by those skilled in the art can be used for the construction of expression vectors containing the DNA sequences encoding GIF1 proteins and proper transcription/translation regulation elements. These methods include in vitro recombinant DNA techniques, DNA synthesis techniques, in vivo recombinant techniques, and so on. The DNA sequences may be effectively linked to a proper promoter in the expression vector to direct the synthesis of mRNA. The expression vector may also include a ribosome binding site for initiating translation and a transcription terminator.

Furthermore, the expression vectors preferably include one or more selective marker genes, which provide a phenotype for selecting transformed host cells, such as dihydrofolate reductase, neomycin resistance, and green fluorescence protein (GFP) for eukaryotic cell culture, and kanamycin as well as ampicillin resistance for *E. coli*.

The vectors that contain aforementioned proper DNA sequences, promoter or regulation sequences can be transformed into appropriate host cells to express the proteins.

The hose cells can be prokaryotic cells, such as bacterium cells; or lower eukaryotic cells, such as yeast cells; or higher eukaryotic cells, such as plant cells. Typical examples are *E. coli, Streptomyces, Agrobacterium tumefaciens*; fungus cells such as yeast; plant cells, etc.

When the polynucleotides of the invention are expressed in higher eukaryotic cells, insertion of an enhancer sequence in the vector can enhance transcription. Enhancer is a DNA cis-acting element with about 10-300 bp, which acts on the promoter to enhance gene transcription.

Artisans in the art know how to select proper vectors, promoters, enhancers and host cells.

Transformation of host cells with recombinant DNA may be performed using conventional techniques known to those skilled in the art. When the host is a prokaryote, such as *E. coli*, competent cells capable of DNA uptake, can be prepared from cells harvested after exponential growth phase and subsequently treated by the $CaCl_2$ method using known procedures. Another method includes the use of $MgCl_2$. Transformation can also be performed through electroporation when necessary. When the host is an eukaryote, DNA transfection methods, including calcium phosphate co-precipitation, conventional mechanical methods such as microinjection, electroporation, or liposome encapsulation, may be used. Plant transformation may also use the method of *Agrobacterium tumefaciens* transformation or particle gun transformation, such as the leaf disc method, rice immature embryo transformation method, etc. Transformed plant cells, tissues and organs can be regenerated to plants to obtain a plant with an improved grain filling ability or grain quality.

The obtained transformants may be cultured using conventional methods to express the polypeptides encoded by the genes of the invention. Culture medium may be selected from various conventional culture media based on the host cells used. When the host cells have grown to a proper density, the selected promoter may be induced using appropriate methods (such as temperature transformation or chemical induction), followed by incubation for an additional period of time.

The recombinant polypeptides in the aforementioned methods may be expressed intracellularly or on the cell membranes, or secreted to the outside the cells. If necessary, the recombinant proteins may be isolated and purified using various isolation techniques according to its physical, chemical or other characteristics. These techniques are known to those skilled in the art. Examples of the techniques include, but are not limited to, conventional renaturation treatment, treatment with protein precipitator (saltingout), centrifugation, cell lysis by osmosis, ultra-treatment, ultracentrifugation, size-exclusion chromatography (gel filtration), absorption chromatography, ion-exchange chromatography, high performance liquid chromatography (HPLC), other liquid chromatography techniques or a combination thereof.

The recombinant GIF1 proteins or polypeptides may be subject to various applications, including screening of antibodies, polypeptides or other ligands that enhance or inhibit the GIF1 protein functions. Screening polypeptide banks using expressed recombinant GIF1 proteins can be used to find valuable polypeptide molecules that are capable of inhibiting or stimulating GIF1 protein functions.

Polynucleotides of the invention may be partly or entirely fixed on a microassay or DNA chip (also termed as "gene chip") as a probe for the differential expression analysis of genes in tissues. Transcription product of GIF1 proteins may also be tested by in vitro amplification of RT-PCR with GIF1 specific primers.

The invention also relates to methods for improving crops, wherein the methods may comprise enhancing the expression of GIF1 genes or their homologous genes in the crops.

The methods for enhancing the expression of GIF1 genes or their homologous genes are known to those skilled in the art, such as driving the expression of GIF1 genes using strong promoters. Enhancer (such as the first intron of rice waxy gene, and the first intron of Actin gene) may be alternatively used to enhance the expression of GIF1 genes. Strong promoters suitable for the methods of the invention include, but not limited to, 35S promoter, Ubi promoters of rice and maize, etc.

As a preferred embodiment of the invention, a method for improving crops may comprise the followings steps:

(1) providing *Agrobacterium tumefaciens* harboring an expression vector, wherein the expression vector comprises a DNA sequence encoding a GIF1 protein;
(2) contacting a plant a cell, a tissue or an organ with the *Agrobacterium tumefaciens* of step (1), to allow for transfection of said DNA sequence encoding the GIF1 protein into the plant cell, tissue, or organ, and to allow for integration into the host chromosome;
(3) selecting the plant cell, tissue or organ transfected with the DNA sequence encoding the GIF1 protein;
(4) regenerating the plant cell, tissue or organ of step (3) into a plant.

Any appropriate conventional means, including reagents, temperature, pressure condition, etc, may be used for the application of the methods.

Moreover, the invention also relates to applications of the crop grain filling traits as tracing labels for transgenic plant offspring. Furthermore, the grain filling traits of said genes may also be applied as indication labels for the eu-hybrids during breeding by crossing.

In one example of the invention, an OsGIF1 gene having a genome sequence of 6840 bp (SEQ ID NO: 3) was presented. The ORF was located at 2380-2594, 3723-4605, 4994-5152, 5903-6168, 6276-6364, 6651-6840, and the total cDNA (SEQ ID NO: 1) was 1797 bp, which encoded a protein (SEQ ID NO: 2) comprising 598 amino acids. The OsGIF1 gene can be used to provide novel approaches for improving crop varieties, and therefore exhibits a profound potential for practical application.

In one example of the invention, an AtGIF1 gene having a genome sequence of 2957 bp (SEQ ID NO: 8) was presented. The total cDNA (SEQ ID NO: 6) was 1755 bp, which encoded a protein (SEQ ID NO: 2) comprising 584 amino acids. The AtGIF1 gene can be used to provide novel approaches for improving crop varieties, and therefore exhibits a profound potential for practical application.

In one example of the invention, a ZmGIF1 gene having a genome sequence of 4412 bp (SEQ ID NO: 11) was presented. The total cDNA (SEQ ID NO: 9) was 1782 bp, which encoded a protein (SEQ ID NO: 10) comprising 593 amino acids. The ZmGIF1 gene can be used to provide novel approaches for improving crop varieties, and therefore exhibits a profound potential for practical application.

Advantages of the present invention may include:

(1) it is the first time to isolate and obtain a novel crop grain filling gene GIF1, which is capable of dominating grain filling and controlling crop quality.

(2) crop grain filling gene GIF1 serves as a gene for dominating crop grain filling and enhancing crop yield as well as quality, and is applied to varietal improvement.

Embodiments of the invention may be further illustrated by the following examples. It is appreciated that these examples are only intended to illustrate the invention, but not to limit the scope of the invention. For the experimental methods in the following examples, they may be performed under routine conditions, e.g., those described by Sambrook et. al., in Molecule Cloning: A Laboratory Manual, New York: Cold Spring Harbor Laboratory Press, 1989, methods reported in PCR Primer: A Laboratory Manual by Carl W. Dieffenbach and Gabriela S. Devksler eds. (Cold Spring Harbor Laboratory Press, 1995), or as instructed by the manufacturers, unless otherwise specified.

Materials and Methods

1. Cloning and transformation of pCAMBIA1301-OsGIF1

OsGIF1 was digested by restriction enzymes Mun1 and BamH1, and was thereafter ligated to BamHI and EcoRI digested pBluescript sk+ (Stratagene). The clone produced was further digested by Hind III and Bam HI, and was cloned to equally digested pCAMBIA1301 (cf. http://www.bios.net/daisy/cambia/585.html#dsy585_gus_intron) to obtain pCAMBIA1301-OsGIF1.

Transformation of pCAMBIA1301-OsGIF1 into *Agrobacterium tumefaciens* was carried out using the following protocol:

1. add 1 μg of pCAMBIA1301-OsGIF1 plasmid to competent cells of *Agrobacterium tumefaciens* EHA 105 (Hood, E. E., Gelvin, S. B., Melchers, L. S, and Hoekema, A., Transgenic Res., 1993, 2, 208-218) and incubate on ice for 30 min;
2. freeze the cells by liquid nitrogen for 1 min;
3. thaw frozen cells in 37° C. water;
4. add 1 mL of YEP and incubate at 28° C. for 2-4 h;
5. spread 200 μl of the above suspension on antibiotics-containing YEP plates;
6. incubate the plates for 2 days at 28° C. until positive colonies are observed and select the positive colonies.

2. Induction and Transformation of the Calli of Rice Mature Embryos

Hulls of ZH11 and mutant (Osgif1) seeds were removed. The seeds were immersed in 70% ethanol for 1 min, and then in 20% (v/v) NaClO for 20 min with shaking. They were then washed with sterilized water for 5-6 times to yield ivory white grains without abnormal smell. Excessive water was blotted with aseptic filter paper, and the calli were induced on the NBD/N6 culture medium. After being cultured in dark at 26° C. for 1 week, the calli were peeled off, and the endosperm, embryo and radicel were collected.

The calli were subcultured in dark on the NBD/N6 culture medium (Sigma), and were passaged every 2-3 weeks as receptors.

3. *Agrobacterium*-Mediated Transformation of Rice Calli

In accordance with embodiments of the invention, *Agrobacterium*-mediated transformation may be performed as follows:

1. inoculate the calli on the NBD/N6 medium, and incubate in dark at 25-26° C. for 4 days;
2. prepare YEB CM culture medium;
3. streak *Agrobacterium tumefaciens* EHA105 containing the recombinant plasmid pCAMBIA1301-OsGIF1 on YEB medium (containing 50 ul/ml of Kan and 20 ug/ml of Rif), and culture the same at 28° C., 200 rpm for 36 h;
4. culture the bacteria until $OD_{660}$ reaches 1.0-1.5;
5. transfer the calli into a sterilized triangular flask;
6. pour proper amount of the above cultured *Agrobacterium tumefaciens* EHA105 into the flask and ensure that all the calli are immersed therein;
7. incubate at ambient temperature for 20 min with gentle shaking;
8. remove the bacterium suspension and blot excessive suspension using aseptic filter paper; transfer the calli onto the NBD culture medium (+AS100);
9. co-culture at 20-25° C. for 2-3 days;
10. transfer the co-cultured calli into a sterilized triangularflask, wash the calli with sterilized water containing 500 mg/L carbenicillin for 2-3 time to remove the bacteria;
11. transfer the Galli to the selective medium (containing NBD, 200 mg/L of Timent and 50 mg/L of hygromicin (Hyg)) for screening of transformed cells. Perform two to three screening cycles (3 weeks for each).
12. transfer the pre-differentiated calli to differential medium (containing NB, 2 mg/L of BAP, and 0.5 mg/L of NAA) after 2-3 week, incubate at 26° C. for 16 h with light and 8 h in dark.
13. transfer the resistance regenerated plant to root media (containing 1/2MS and 0.5 mg/L of NAA) after 2-3 weeks for strong seedling and rooting;
14. wash away the agar from the resistance regenerated plant after 3 weeks, transplant it to the greenhouse, and collect the seeds for molecular identification.

4. Quantification of Sugar and Starch

Developing grains were harvested, immediately frozen in liquid nitrogen and stored at −80° C. until use. Sugar content and starch levels in grains without hulls were determined using the method by Hampp et al. (Hampp, R., Egger, B., Effenberger, S. & Einig, W. Carbon Allocation in Developing Spruce Needles—Enzymes and Intermediates of Sucrose Metabolism. Physiologia Plantarum 90, 299-306 (1994)).

Example 1

Population Construction, Gene Cloning and Function Analysis

The inventor discovered a rice mutant from the mutant bank induced from Zhonghua 11 (ZH11), wherein the seed filling of the mutant was seriously compromised. Vegetative growth of the mutant crop showed no significance to wild-type ones, while grain filling was significantly compromised with a decrease in the weight of 1,000 grains of 15-30% and a reduction in rice quality. It was then entitled Osgif1 (grain incomplete filling 1), which confirmed that the OsGIF1 gene was an important gene that controlled the crop yield and rice quality through grain filling.

The inventor obtained a gene mapping population through the hybridization between the Osgif7 mutant and Zhenshan 97. A scan for the LIF1 locus was performed through Bulked Segregant Analysis (BSA) using the 130 pairs of SSR primers uniformly distributed on the 12 rice chromosomes. The Lif1 locus was primarily mapped to be near the SRD5 region on the long arm of chromosome 4, and was ultimately mapped to a 32-kb fragment between caps-4 and caps-8 comprising three putative genes. The inventor discovered a 1-nt deletion in the Osgif1 mutant (nt 4588 on the DNA sequence of OsGIF1 genome) based on the DNA sequencing of the mutant and wild-type crops.

Through fine-mapping of OsGIF1, sequencing and function validation, the inventor obtained the genome sequence of wild-type OsGIF1 (DNA) as shown by SEQ ID NO: 3 (including promoter), the sequence of OsGIF1 coding region (cDNA sequence) as shown by SEQ ID NO: 1, and the protein sequence of OsGIF1 as shown by SEQ ID NO: 2.

In the case of the aforementioned mutation (deletion of the No. 4588 nucleotide in the genome sequence of OsGIF1), the mutant did not express OsGIF1 protein.

Example 2

Effect of GIF1 Gene on Grain Filling and Yield

The inventor compared various phenotypes of rice grains from gif1 mutant with those of OsGIF1 wild-type ZH11 crops. Results were shown in Table 2.

As illustrated in the Table, the gif1 mutation interfered with seed filling and reduced crop yield although ear number or seed number was not affected. The results showed in following Example 3 demonstrated that transgenic complementation could effectively eliminate such effects and control rice grain filling, and thus increasing the crop yield.

Example 3

Effect of OsGIF1 Gene on Rice Quality

The grains of brown rice and polished rice having wild-type OsGIF1 gene were big and full, while those of the mutant rice without the expression of OsGIF1 gene were small and not full. The inventor constructed the recombinant plasmid of pCAMBIA1301-OsGIF1 containing OsGIF1 gene, and transformed the same to the mutant (gif1) calli. The mutant transgetic plant was thus obtained, which could regain the wild-type features.

Figure 1:
FIG. 1 shows the effect of GIF1 gene on rice quality, wherein FIG. 1A refers to brown rice grains of wild-type plant.
Figure 7:
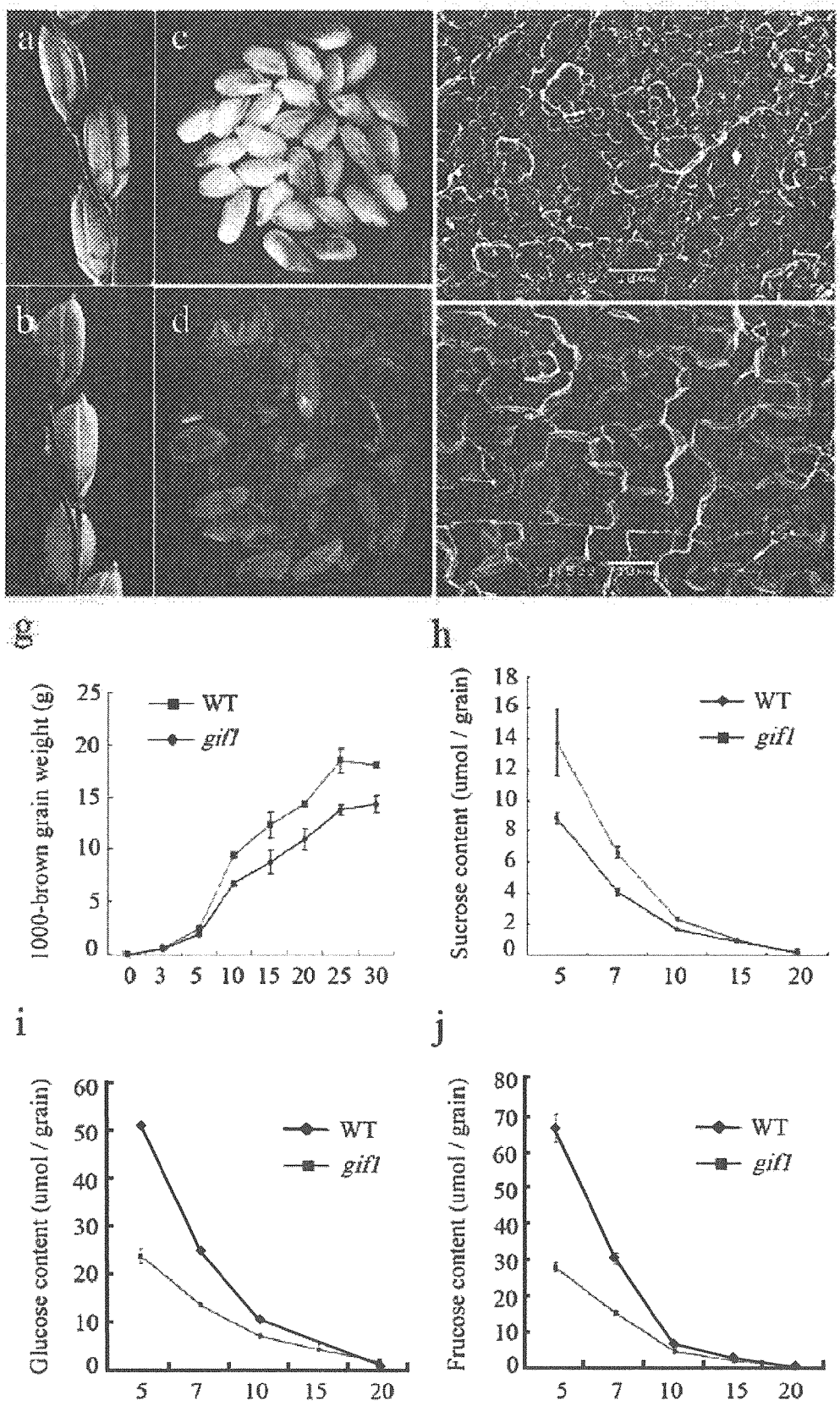
FIG. 7 shows grain-filling and sugar content of wild-type or gif1 mutant grains. (a) and (b) gif1 mutant grains (a) and wild-type grains (b) on 25DAF. (c) and (d) polished rice grains of gif1 mutant rice (c) and wild-type rice (d). (e) and (f) SEM analysis of gif1 mutant grains (e) and wild-type grains (f). Results show abnormal development and loosening of gif1 mutant starch granules. (g) grain filling process (1000-brown rice weight) of wild-type or gif1 mutant rice. (h)-(j) sucrose, sugar, and fructose contents in wild-type or gif1 mutant grains, respectively.

Results were shown in FIG. 1 and FIGS. 7(a-g). The grains of brown rice and polished rice having wild-type OsGIF1 gene were big and full, while those of mutant rice without the expression of OsGIF1 gene were small and not full.

Therefore, the mutant (gif1) had reduced rice quality, whereas transgenic complementation could effectively compensate for the reduction in rice quality as induced by the gif1 mutation and thereby improving the crop quality.

Figure 8:
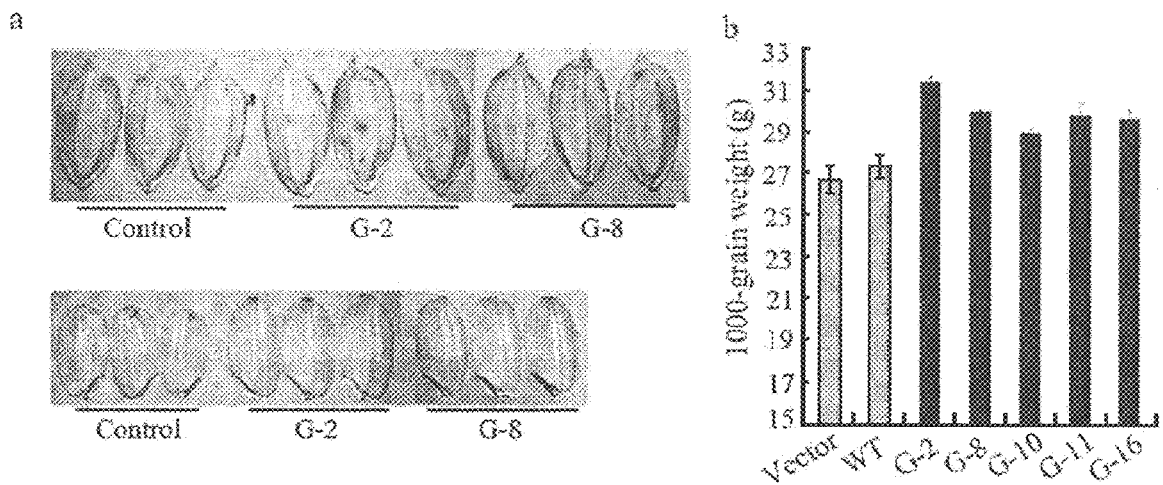
FIG. 8 shows the enlarged size of the grains of transgenic rice overexpressing GIF1. (a) Two transgenic rice lines, G-2 and G-8, overexpressing GIF1, are compared to control wild-type rice in terms of grain size. Results show that the transgenic rice lines possess larger grains. (b) comparison of grain weight among five transgenic rice lines overexpressing GIF1 (G-2, G-8, G-10, G11, and G-16), wild-type rice (WT), empty vector transformed rice (Vector). Statistically difference: *$P<0.05$.
Figure 9:
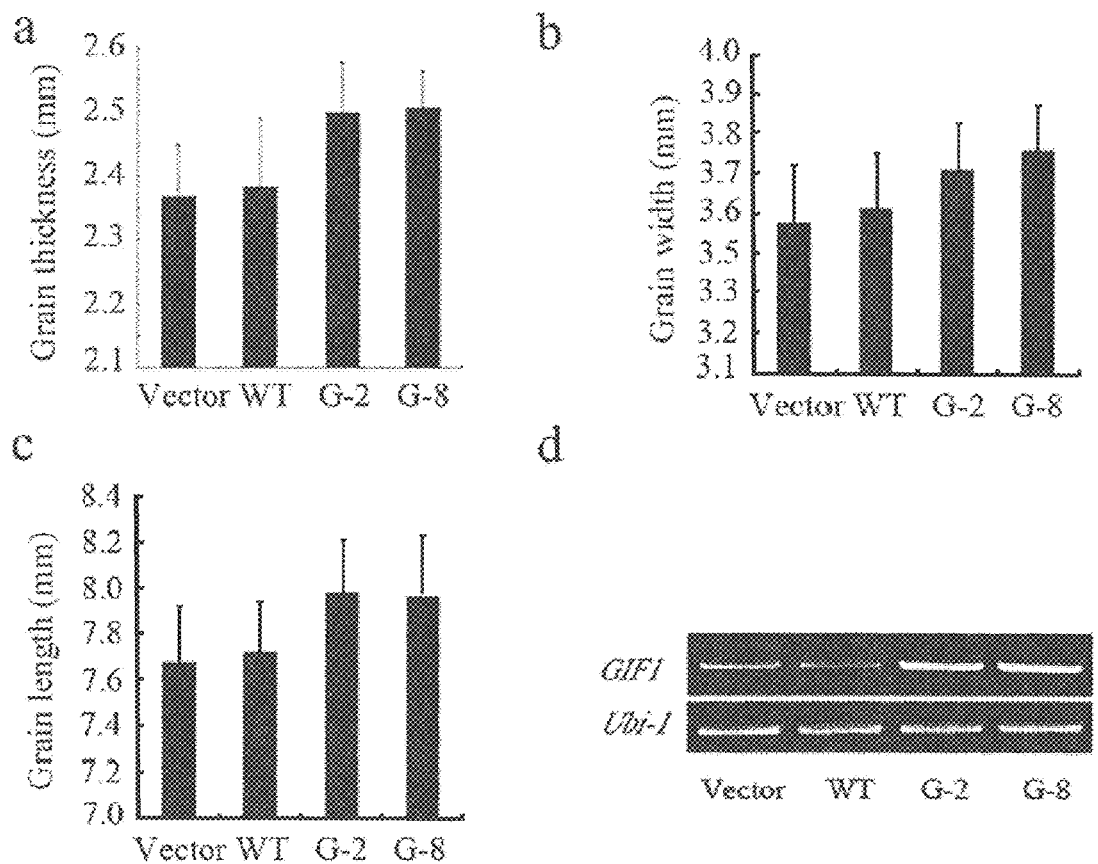
FIG. 9 illustrates that grains of transgenic rice with additional GIF1 show an increase in thickness, width as well as length, and enhanced expression of GIF1. (a-c) two transgenic rice lines of G-2 and G-8 overexpressing GIF1 are compared with wild-type rice (WT) and empty vector transformed rice (Vector) in terms of grain thickness (a), width (b), and length (c). Results confirm that transgenic rice lines of G-2 and G-8 that overexpress GIF1 possess larger grains. (d) two transgenic rice lines of G-2 and G-8 overexpressing GIF1 are compared with wild-type rice (WT) and empty vector transformed rice (Vector) in terms of gene expression level of GIF1 using RT-PCR. Results illustrate that transgenic rice lines of G-2 and G-8 that overexpress GIF1 show higher expression of the GIF1 gene. Ubi-1 refers to the loading control.

Besides, the inventor constructed the recombinant plasmid of pCAMBIA1301-OsGIF1 containing OsGIF1 gene, and transformed the same into the calli of wild-type rice (cultivar TP309). Transgenic crop overexpressing OsGIF1 was obtained, and was compared with the wild-type crop. Results showed that the former possessed bigger and heavier grains as shown by FIGS. 8 and 9 (a-c). mRNAs were extracted from transgenic rice of G-2 and G-8 overexpressing OsGIF1, wild-type rice (WT), and empty vector transformed rice (Vector) to separately amplify OsGIF1 through RT-PCR. The amplified products were detected by agarose electrophoresis, and results showed that the transgenic rice overexpressing GIF1 possessed higher expression level of the OsGIF1 gene (FIG. 9d).

Example 4

Effect of OsGIF1 Gene on Seed Vigor

Plants with wild-type OsGIF1 gene showed strong rooting and rapid leaf growth, while plants with mutant gif1 gene showed significantly weak rooting and slow leaf growth. The inventor constructed the recombinant plasmid of pCAM-

TABLE 2

Effect of gif1 mutant on rice grain phenotype

| | ZH11 | gif1 | gif1/ZH11 | Significance |
|---|---|---|---|---|
| Ear number/crop | 11.00 ± 2.30 | 9.96 ± 2.73 | 0.90 | no |
| Seed number/ear | 122.12 ± 33.71 | 124.82 ± 30.70 | 1.02 | no |
| Seed number/crop | 1343.29 ± 372.12 | 1279.38 ± 239.05 | 0.95 | no |
| Number of incomplete filling seed/ear | 35.56 ± 10.83 | 34.33 ± 15.68 | 0.97 | no |
| Seed weight (g)/ear | 2.90 ± 0.73 | 2.45 ± 0.63 | 0.84 | yes |
| Seed weight (g)/crop | 32.14 ± 8.60 | 25.09 ± 4.44 | 0.78 | yes |
| weight of 1,000 seeds (g) | 24.00 ± 0.01 | 19.71 ± 0.01 | 0.82 | yes |
| weight of 1,000 brown rice grains (g) | 21.33 ± 0.1 | 16.15 ± 0.15 | 0.76 | yes |

BIA1301-OsGIF1 containing OsGIF1 gene, and transformed the same to the calli of the mutant (gif1) to produce the mutant transgenic plant. Rooting and leaf of the transgenic plant could regain the wild-type features.

Figure 2:
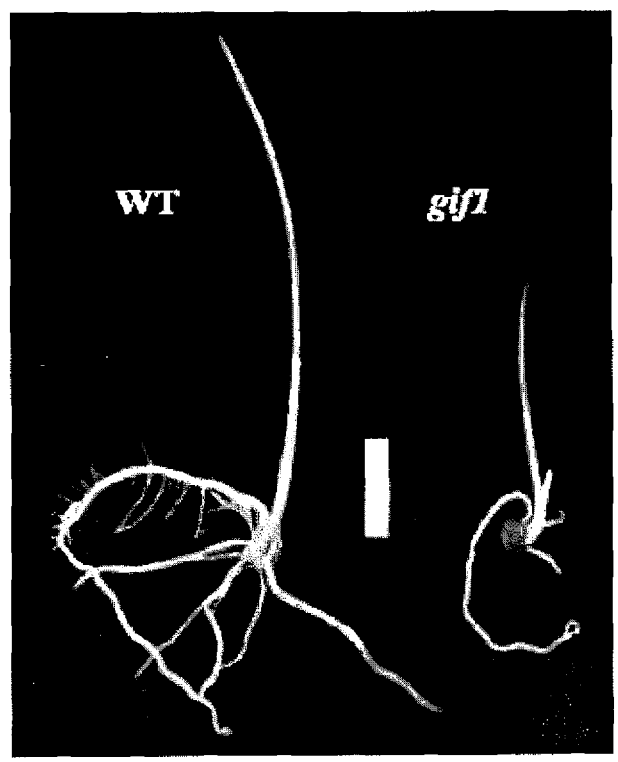
FIG. 2 shows the effect of GIF1 gene on seed vigor, wherein WT (left) refers to ZH11 wild-type plant and gif1 (right) refers to ZH11 mutant plant.

As illustrated in FIG. 2, plants with wild-type OsGIF1 gene showed strong rooting and rapid leaf growth, while plants with mutant gif gene showed significantly weak rooting and slow leaf growth.

Results demonstrated that the gif1 mutant caused a reduced seed vigor, whereas complementation could effectively eliminate the reduction in seed vigor as induced by the gif1 mutant.

Example 5

Effect of OsGIF1 Gene on Seed Ear and Resistance to Storage Diseases

The inventor constructed the recombinant plasmid of pCAMBIA1301-OsGIF1 containing the OsGIF1 gene, and transformed the same to the calli of the mutant (gif1) to produce the mutant transgenic plant. Resistance of the transgenic plant to storage diseases was restored to the wild-type level. Results are shown in FIGS. 3 and 4.

Figure 3:
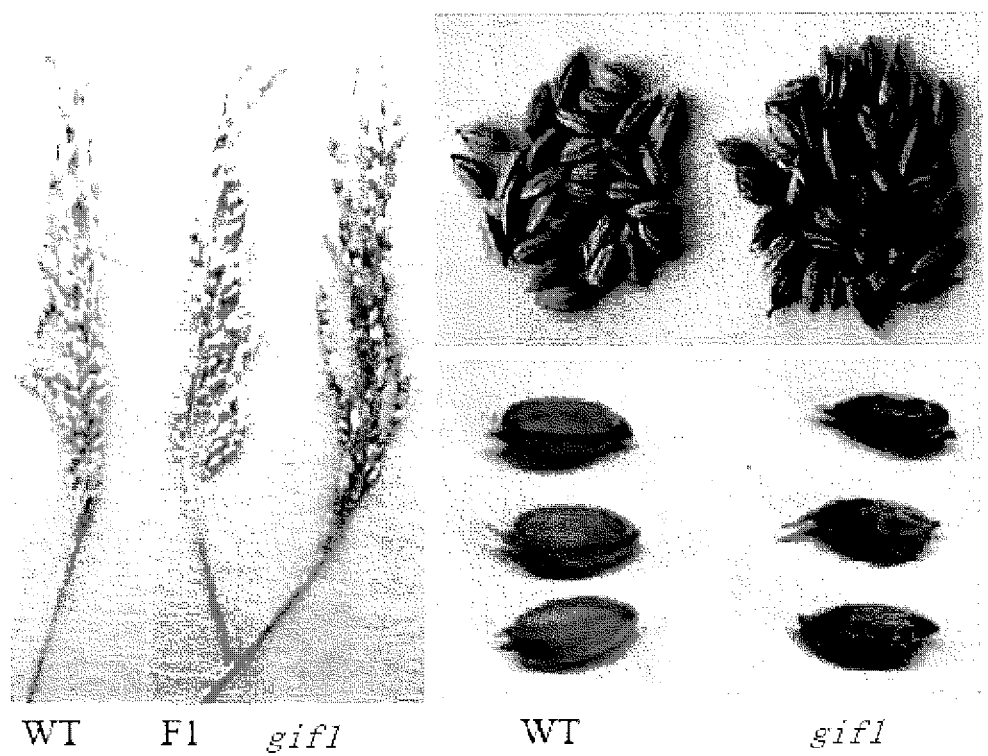
FIG. 3 shows the effect of GIF gene on the crop ear, wherein WT refers to the ear of ZH11 wild-type plant; F1 refers to the ear of the first filial generation of ZH11 wild-type and ZH11 mutant plants; gif1 refers to the ear of ZH11 mutant plant.
Figure 4:
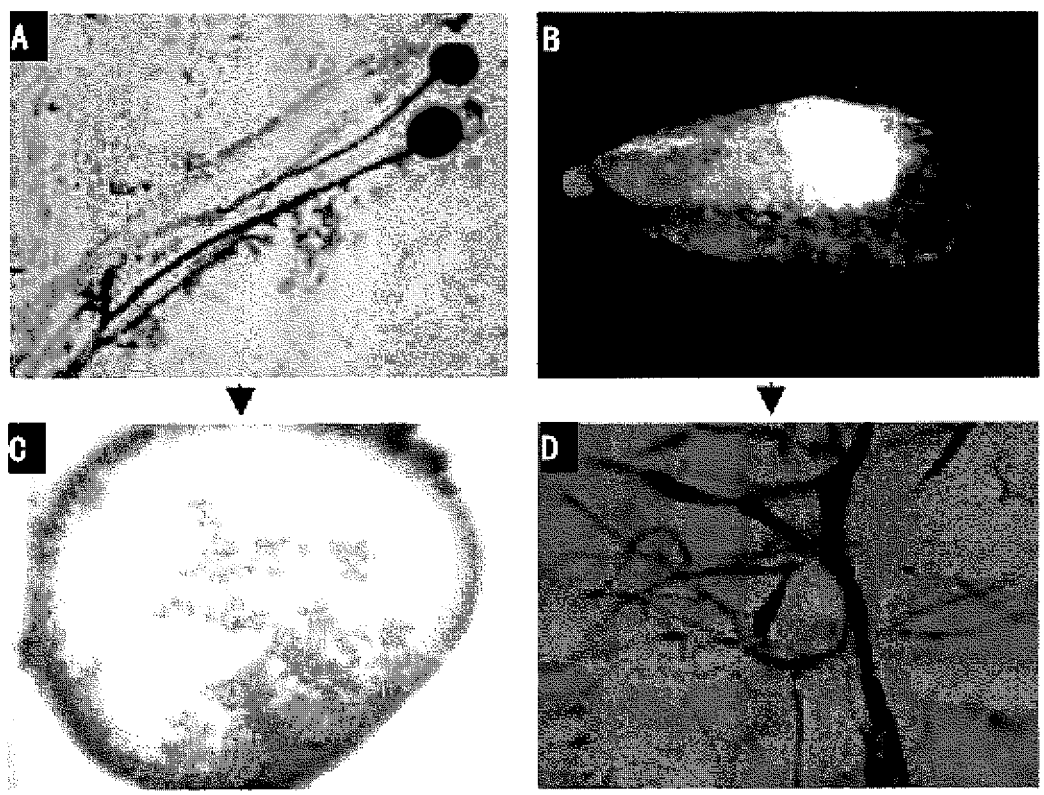
FIG. 4 shows the typical storage disease bacteria isolated from the seeds of gif1 mutant plant, wherein FIG. 4A and FIG. 4C (magnification of FIG. 4A) refer to the isolated *Rhizopus* sp.

As shown in FIG. 3, plants with wild-type OsGIF gene possessed full ears, while plants with mutant gif gene possessed notably shriveled ears which were more susceptible to diseases. FIG. 4 showed the typical storage disease bacteria isolated from the seeds of gif1 mutant plant, wherein FIGS. 4A and 4B refer to the isolated *Rhizopus* sp. and *Alternaria* sp., respectively. In addition, some other storage disease bacteria were also isolated.

Results indicated that gif1 mutant reduced ear quality and crop resistance towards storage diseases, thus shortening the storage time. Comparatively, transgenic complementation could eliminate such interference and improve the crop resistance.

Example 6

Tissue Specificity of OsGIF1 Gene

The inventor constructed a clone comprising OsGIF1 promoter region operably linked to the GUS reporter gene, and transformed the same into ZH11 rice. Tissue specific expression of the GUS reporter gene and OsGIF1 gene as promoted by the OsGIF1 promoter was evaluated. Detailed construction method was as follows:

Promoter of the OsGIF1 gene was obtained by PCR with forward primer (tataagettgateggccatactcc (SEQ ID NO: 4)), reverse primer (taggatccctttgctctcacacttg (SEQ ID NO: 5)), and using the OsGIF1 genome DNA as template. The promoter was cloned into pBI101 (from Clonetech, bearing GUS), which was then digested by EcoR I and Hind III. The fragment obtained was collected and ligated to equally digested pCAMBIA1300 to produce the desired clone containing pCAMBIA1300+promoter+GUS (method for the tissue coloration assay was described in Jeferenson, R A (1987) Plant Mol Biol Rep).

As shown in FIGS. 5A-K, specific expression of the OsGIF1 gene was detected in the root, internode, and vascular trace in the dorsiventral region of the seed.

Figure 5:
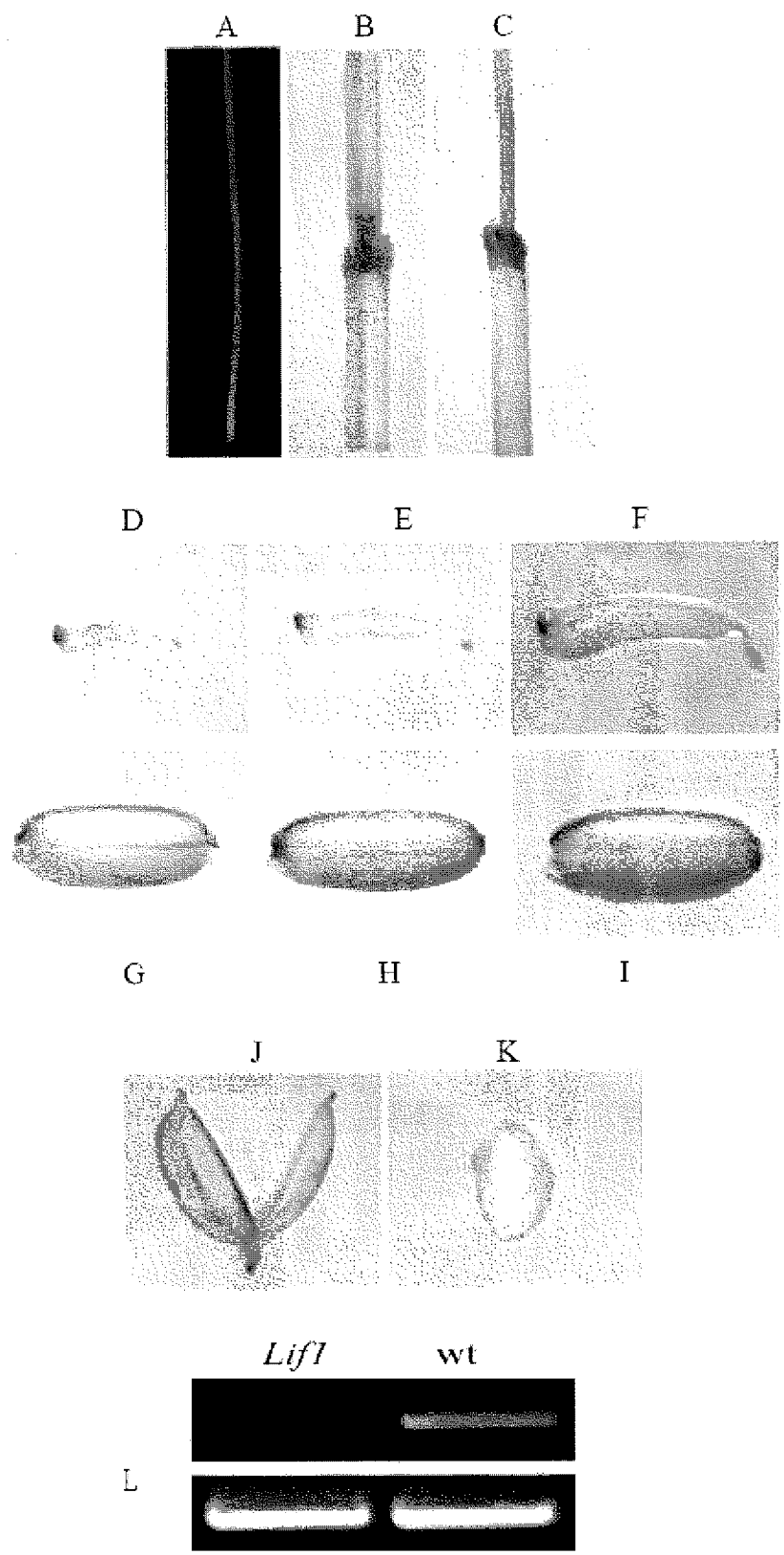
FIG. 5 shows the tissue specificity of GIF1, wherein Fig. A represents root; Fig. B represents internode; Fig. C represents stretched-out (elongated) internode; Fig. D represents the $2^{nd}$ day; Fig. E represents the $4^{th}$ day; Fig. F represents the $6^{th}$ day; Fig. G represents the $10^{th}$ day; Fig. H represents the $15^{th}$ day; Fig. I represents the $25^{th}$ day; Fig. J represents glume; Fig. K represents cross section of seed on the $10^{th}$ day; Fig. L represents the expression of GIF1 gene in mutant and wild-type plants; Fig. M represents the expression of GIF1 gene in seedlings, leaves, roots, internodes, and ears (wherein LS refers to rice seedlings, L to rice leaves, R to rice roots, I to rice internodes, and P to ears); Fig. N represents the expression of GIF1 gene at different time intervals post to flowering; and DAF (Day After Flowering) refers to the number of days post to flowering.
Figure 5:
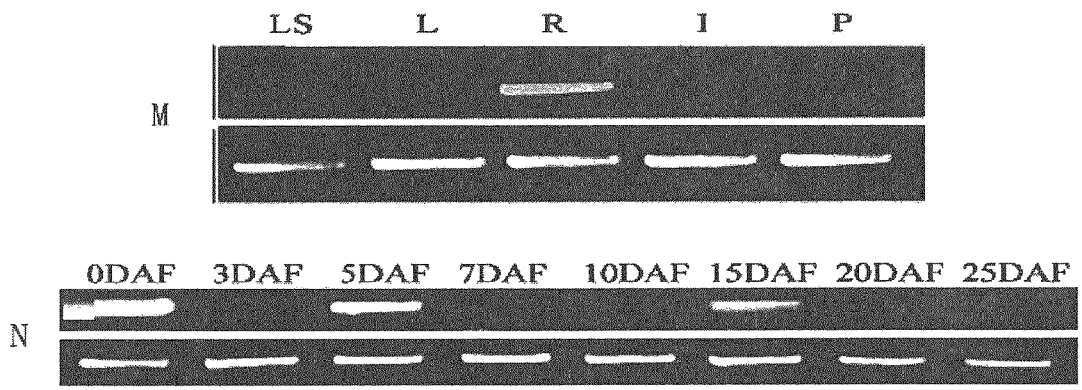

In addition, mRNA was extracted from wild-type or mutant crops, and OsGIF1 was separately amplified through RT-PCR. The amplified products were detected by agarose electrophoresis. The results were shown in FIGS. 5L-N. FIG. 5L showed the RT-PCR result of mRNA from gif1 mutant and wild-type crops; FIG. 5M showed the RT-PCR result of mRNA from different rice tissues; FIG. 5N showed the RT-PCR result of mRNA from rice ear on different days after flowering (DAF).

Example 7

Effect of OsGIF1 Gene on Sugar Metabolism and Accumulation in Grains

The inventor constructed the recombinant plasmid of pCAMBIA1301-OsGIF1 containing OsGIF1 gene, and transformed the same to the calli of the mutant (gif1) to produce the mutant transgenic plants. Sugar metabolism and accumulation of the transgenic plants were monitored and compared with that of the wild-type ZH11 plant.

Figure 6:
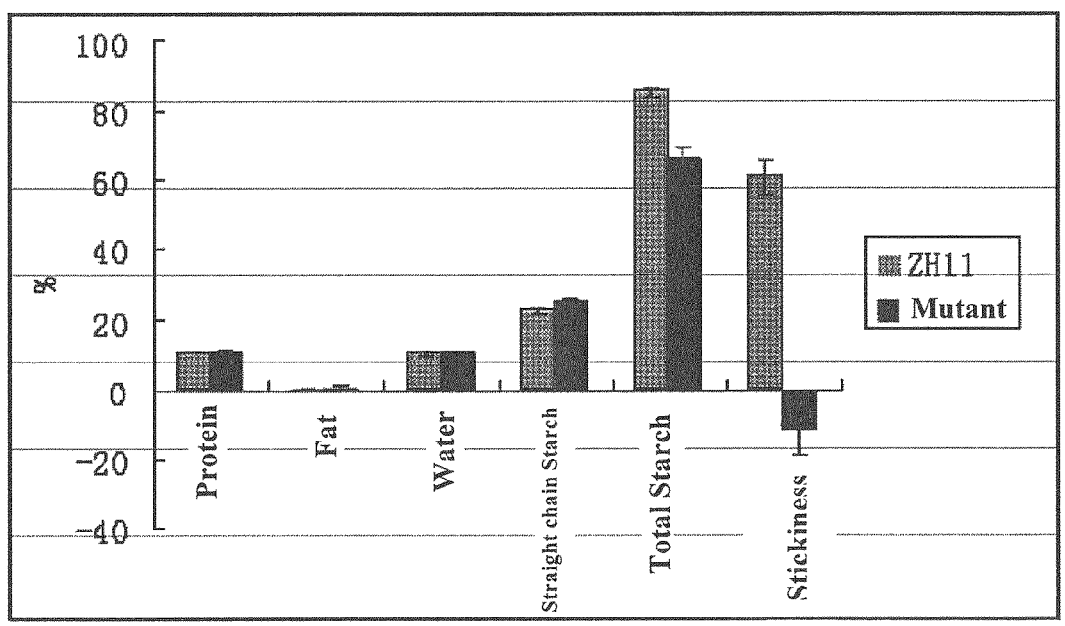
FIG. 6 shows the effect of GIF1 gene on the grain sugar metabolism and accumulation, wherein total starch includes amylose and amylopectin.

As shown in FIGS. 6 and 7 (h-j), OsGIF1 could successfully regulate sugar metabolism and accumulation in grains, thus regulating grain quality.

In addition to the OsGIF1 gene described above, inventors of the present invention also investigated genetic manipulation of GIF1 genes and proteins from *Arabidopsis* (AtGIF1) and maize (ZmGIF1). As with OsGIF1 gene, these GIF1 genes (AtGIF1 and ZmGIF1) were also able to improve growth rate, grain yield and starch contents in maize. These results suggest that other GIF1 genes and proteins would also have the abilities to improve the graining filling and yields of crops. The following examples will use maize (*Zea mays* L.), specifically the elite maize (*Zea mays* L.) inbred line Ye478, to illustrate such uses.

From the inbred line (Ye478), different transgenic plants may be produced by the *Agrobacterium tumefaciens*-mediated transformation, as noted abovew. For analysis of tissue expression of ZmGIF1, total RNA was extracted from various tissues of B73 maize with RNAiso Plus™ and RNAiso-Mate™ for Plant Tissue (TaKaRa, Dalian, China), and treated with RNase-free DNase (Promega, Shanghai, China). First-strand cDNA synthesis was performed with the ReverTra Ace® (TOYOBO, Osaka, Japan).

Gene Clone and Plasmid Construction

The ZmGIF1 gene and 2-kb promoter region were cloned from the B73 maize. The AtGIF1 gene was cloned from *Arabidopsis thaliana* (ecotype Columbia-0). Total RNA was isolated with the TRIZOL reagent (Invitrogen, Shanghai, China) following the manufacturer's instructions. The coding sequences of the various GIF1 genes, respectively, together with double cauliflower mosaic virus (CaMV) 35S promoter, the bar gene, which enables the plant to resist the herbicide glufosinate, were cloned into pCAMBIA3301, after appropriate digestion using standard protocols described by Sambrook et al. (Supplementary FIG. 3). The resultant plasmids were then introduced into *Agrobacterium tumefaciens* strain EHA105 by the freeze-thaw method.

Complementation Test and β-Glucuronidase (GUS) Activity Analyses

The ZrnGIF1 gene with its promoter region was inserted into the binary vector pCAMBIA3301 to generate the plasmid pZmPr-ZnGIF1. The plasmid was introduced into the mn1 mutant (i.e., Zmgf1 mutant). To generate ZmGIF1 promoter-GUS construct, the 2-kb promoter region was inserted into the pCAMBIA3381Z vector and introduced into the inbred line Ye478. GUS activities in the transgenic plants were assessed by histochemical assays.

Molecular Analyses

Genomic DNA was isolated from maize leaves by the cetyltrimethylammonium bromide (CTAB) method. PCR assays were performed with specific primers. Total RNA was prepared from maize tissues using TRIZOL® reagent (Invitrogen, Shanghai, China) according to the manufacturer's protocol. For RT-PCR, 1-5 μg of total RNA was used for cDNA synthesis with the RevertAid First Strand cDNA Synthesis Kit (Fermentas). Real-time PCR was carried out with primers and SYBR Green Realtime PCR Master Mix (TOYOBO, Osaka, Japan).

Chlorophyll Fluorescence Measurements, IAA and Sugar Content Determination of Maize Plants in Flowerpots Seeds of T2 homozygous transgenic and wild type (WT) lines (Ye478) were sown in the flowerpots (diameter, 28 cm; height, 28 cm) with homogeneous loam and were grown in a greenhouse at 32/22° C. (day/night) with a photon flux density of 700 μmol/m$^2$/s, a relative humidity of 50-60% and a photoperiod of 14/10 h (light/dark). The plants were thinned to two plants per pot when they reached the 4-leaf stage, and were watered sufficiently every day till the 13-leaf stage. Then, the photosynthesis activities were measured on the 10th fully-expanded leaves using Junior-PAM (Walz, Germany) after a 5 min dark adaptation according to the manufacturer's protocol. For the IAA content determinations, the 13th leaf was frozen with liquid nitrogen, homogenized and then lyophilized. Samples of 2 g dry weight (DW) were purified and finally analyzed at Hunan Normal University (Changsha, China) using the described methods. For the sugar content, the 5th, 8th and 11th leaves were used. The fresh weight (FW) of aerial parts of WT and transgenic lines were measured.

Scanning Electron Microscope (SEM)

The kernels from mature mutant, complementary, WT and transgenic maize were harvested and dried. Then, these kernels were cast into blocks, and the sections were cemented onto aluminum specimen support stubs, coated with gold by sputter coating, and examined in a scanning electron microscope (JSM-6360LV; JEOL, Tokyo, Japan).

Field Trials

Field experiments were carried out in the Experimental Field of Jiyuan (Henan Province, April 2011), Nanbin Farm (Hainan Province, October 2011) and Zhangye (Gansu Province, June 2012) using transgenic lines (T3, T4 and T5, respectively) and WT. The trial plots were arranged in a random complete block design with three replications. Forty seeds of each homozygous transgenic and WT line were sown in a double row plot. The plot was 2.5 m length, 1.2 m width and with an interval of 0.25 m between plants. Three replicates were planted. The plants were thinned at the five-leaf stage, resulting in 20 plants in each plot (a population density of approximately 66,700 plants/ha). Growth perfounance was observed during the whole life cycle. Plants at the flowering stage were self-pollinated. Cobs and kernels were collected to take pictures, measure the 100-grain weight and detect sugar concentration on days 7, 14, 21, 28 and 35 after pollination. Kernels of 12 DAP were collected for invertase activity assay. After harvest, ears were dried to constant weight, and then the ear length, ear weight, grain rows, grain number, 1000-grain weight, and starch content were measured for ten randomly selected ears for each plot.

Statistical Analysis

All data are presented as the mean±SE. Data were statistically examined using ANOVA methodology, and differences in value means were compared according to Duncan's multiple comparison tests. All analyses were performed with the SPSS 17.0 for windows. A value of $P<0.05$ was considered statistically significant difference.

Example 8

Expression of ZmGIF1 in Maize (Ye478)

Figure 10:
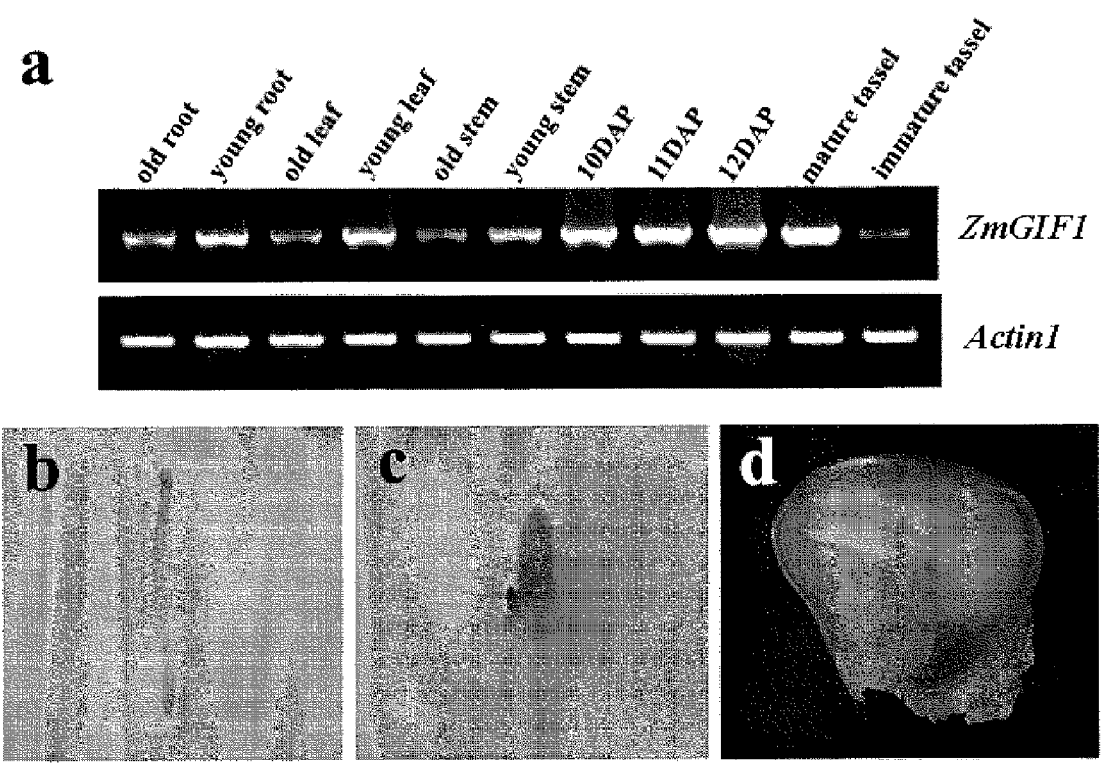
FIG. 10 shows ZmGIF1 gene expression and GUS staining analyses. (a) RT-PCR analyses of ZinGIF1 transcripts in different tissues of wild type maize (Ye478). cDNA derived from the indicated tissues was used as template for PCR with the gene specific primers. The Actin1 gene was employed as an internal control. (b) GUS activity in the growing root ($T_2$). (c) GUS activity in shoot tip ($T_2$). (d) GUS activity in the kernel at 21 DAP ($T_3$). GUS activity was predominantly restricted to the basal endosperm transfer layer (BETL).

RT-PCR analyses demonstrated that ZmGIF1 (ZmCWIN2; also know as Mn1) is ubiquitous expressed in all tested tissues, including root, leaves, stem, and tassels, with the most abundant expression in developing seeds (FIG. 10a). The results shown in FIG. 10a were obtained with cDNA derived from the indicated tissues as templates in PCR with ZmGIF1 gene specific primers. The Actin1 gene was used as an internal control.

Figure 11:
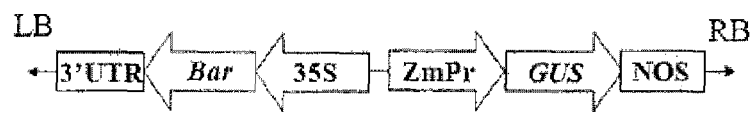
FIG. 11 shows Structure of plant expression vectors used in this study. (a) Schematic structures of the T-DNA region of plant expression vector for GUS activity analysis. The β-glucuronidase (GUS) encoding gene is driven by the ZmGIF1 promoter. (b) Schematic structures of the T-DNA region of plant expression vector for mn1 complementation. ZmGIF1 is driven by its own promoter. (c) Schematic representation of T-DNA regions in the plant expression vectors used for maize transformation. LB, T-DNA left border repeat; 35S, CaMV35S promoter; GUS, β-glucuronidase gene; NOS, nopaline synthase gene terminator; OCS, octopine synthase gene terminator; bar, phosphinothricin N-acetyltransferase gene; RB, T-DNA right border repeat.
Figure 11:
Figure 11:
Figure 11:
Figure 11:

To elucidate the action site of ZmGIF1, the expression of ZmGIF1 was investigated using a pZmGIF1-β-glucuronidase (GUS) reporter transgene (pGIF1-GUS) (FIG. 11a). GUS activity was mainly detected in growing root and shoot tip (FIG. 10b,c), with a strong expression in the basal endosperm transfer layer in the kernel (at 21 DAP (days after pollination)) during early grain-filling (FIG. 10d). This observation is consistent with increased ZmGIF1 transcript accumulations in the filling grains post 10 DAP (FIG. 10a).

Figure 12:
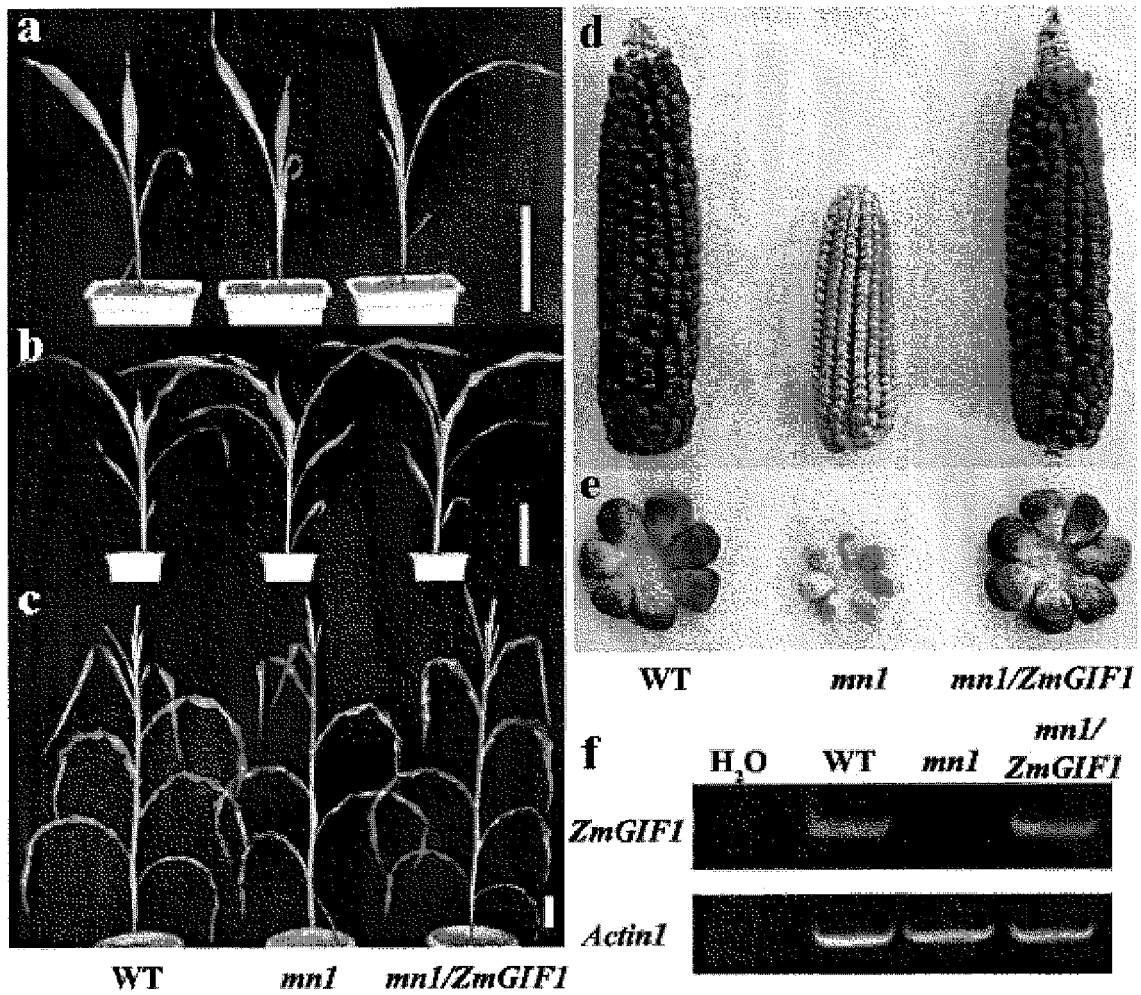
FIG. 12 shows Functional complementation of ZmGIF1 mutant (mn1) by ZmGIF1. (a-c) Phenotypes of wild type (W22), mn1 and its complementary line ($T_2$) mn1/ZmGIF1. Plants were grown in the greenhouse. Photos were taken at four-leaf, seven-leaf and flowering stage, respectively. Scale bar=10 cm. (d, e) Corn cobs and kernels ($T_3$) harvested from wild type (WT), mn1 and mn1/ZinGIF1. (f) RT-PCR analyses. Total RNA was extracted from seeds of W22, mn1 and its complementary line mn1/ZmGIF1 ($T_3$) at 12DAP. RT-PCR analyses were performed with ZmGIF1 gene specific primers. The analysis was repeated twice with similar results. The housekeeping gene Actin1 was used as an internal control.

To confirm the invertase activity, ZmGIF1 was expressed under its native promoter in mn1 mutant (FIG. 11b). As shown in FIG. 12, transformation of ZmGIF1 restored the mn1 seed phenotype to the wild type). These results show that the phenotypic changes manifested by the mn1 mutant indeed result from disruption of the ZmGIF1 gene.

Figure 13:
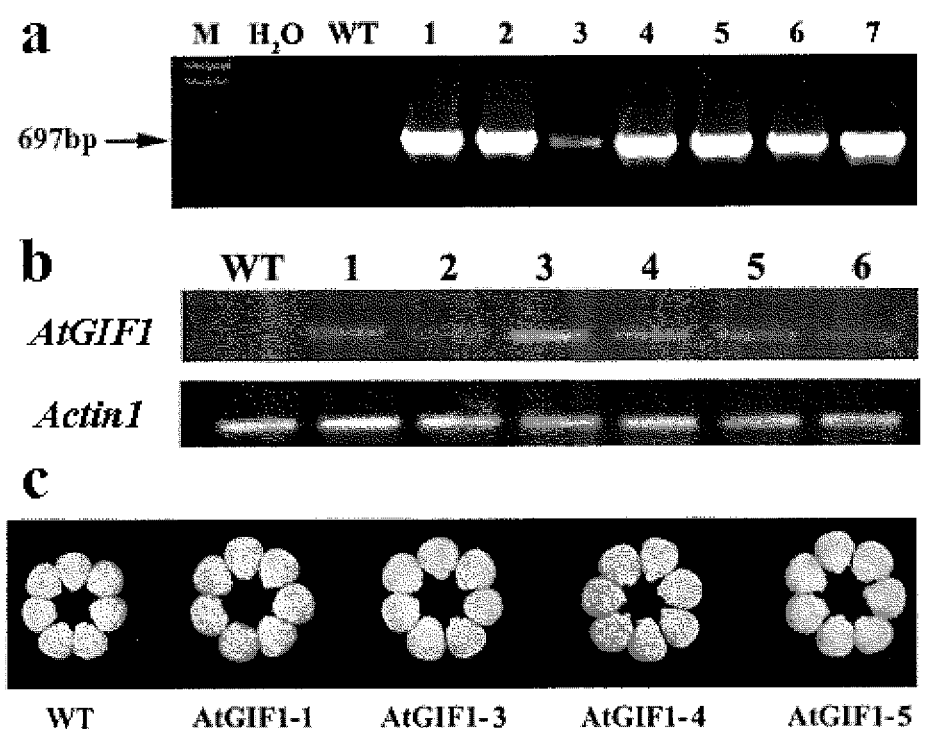
FIG. 13 shows Confirmation of transgene integration and expression by PCR, RT-PCR and comparison of kernel sizes. Genomic DNA or total RNA was isolated from leaves of wild type Ye478 (WT) and transgenic ($T_3$) plants constitutively expressing AtGIF1 (lines 1-7). Plants were grown to the five-leaf stage in the greenhouse. (a) PCR analysis using AtGIF1-specific primers. A 697 bp PCR product was detected in all transgenic lines. M, λ-EcoT14 I digest DNA markers; $H_2O$, PCR product with double distilled water as template; WT, PCR product with wild type plant genomic DNA as template; 1-7, PCR products with transgenic plant genomic DNA as template. (b) RT-PCR analysis. RT-PCR was performed using AtGIF1-specific primers or Actin1-specific primers. The Actin1 gene was used as an internal control. (c) Kernels of Ye478 (WT) and transgenic maize plants ($T_4$).
Figure 14:
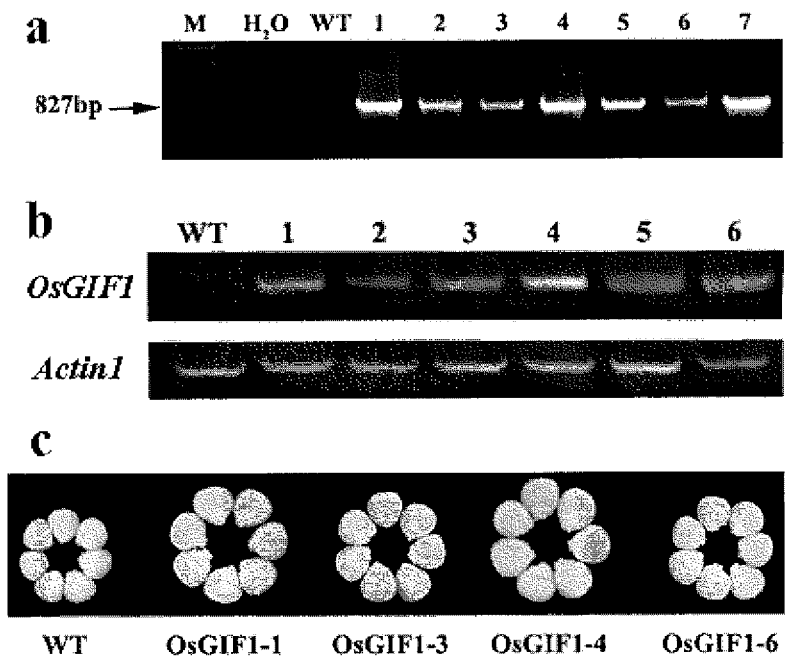
FIG. 14 shows Confirmation of transgene integration and expression by PCR, RT-PCR and comparison of kernel sizes. Genomic DNA or total RNA was isolated from leaves of wild type Ye478 (WT) and transgenic ($T_3$) plants constitutively expressing OsGIF1 (lines 1-7). Plants were grown to the five-leaf stage in the greenhouse. (a) PCR analysis of wild type and different transgenic lines of Ye478 using OsGIF1-specific primers. An 827 bp PCR product was detected in all transgenic lines. M, λ-EcoT14 I digest DNA markers; $H_2O$, PCR product with double distilled water as template; WT, PCR product with wild type plant genomic DNA as template; 1-7, PCR products with transgenic plant genomic DNA as template. (b) RT-PCR analysis. RT-PCR was performed using OsGIF1-specific primers or Actin1-specific primers. The Actin1 gene was used as an internal control. (c) Kernels of Ye478 (WT) and transgenic maize plants ($T_4$).
Figure 15:
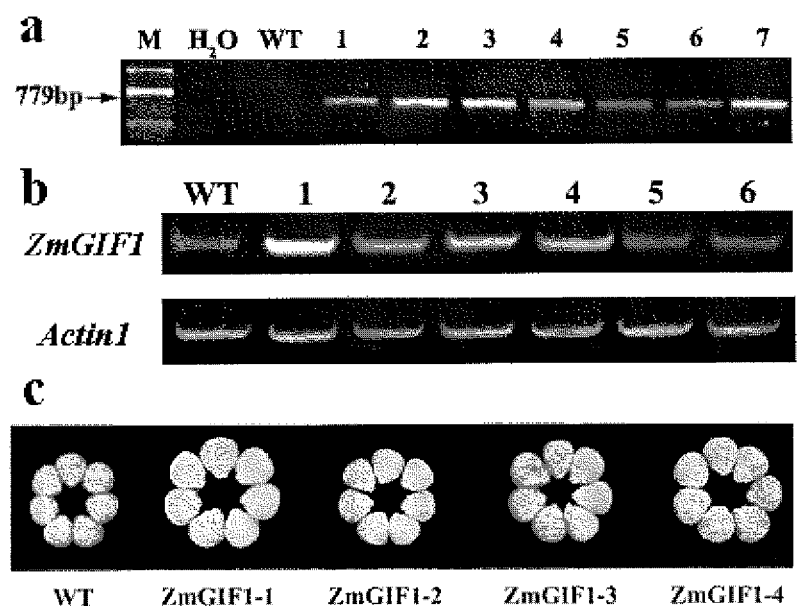
FIG. 15 shows Confirmation of transgene integration and expression by PCR, RT-PCR and comparison of kernel sizes. Genomic DNA or total RNA was isolated from leaves of wild type Ye478 (WT) and transgenic ($T_3$) plants constitutively expressing ZmGIF1 (lines 1-7). Plants were grown to the five-leaf stage in the greenhouse. (a) PCR analysis of wild type and different transgenic lines of Ye478 using ZmGIF1-specific primers. A 779 bp PCR product was detected in all transgenic lines. M, λ-EcoT14 I digest DNA markers; $H_2O$, PCR product with double distilled water as template; WT, PCR product with wild type plant genomic DNA as template.

To investigate the utility of the GIF1 proteins, three constructs containing AtGIF1, OsGIF1 or ZmGIF1 were constructed and introduced into the genome of Ye478, respectively (FIG. 11c). Fifteen AtGIF1, seven OsGIF1 and eleven ZmGIF1 transgenic plants, and six homozygous lines of each construct (gene) from these trangenic plants were identified in the $T_3$ generation. Twelve of these homozygous lines, four lines with different expression levels of each gene, were chosen for further experiments. Homozygous $T_3$ plants were grown in the greenhouse for PCR and RT-PCR confirmation. High levels of GIF1 transcript were detected in all tested transgenic plants. In contrast, no AtGIF1 or OsGIF1 transcript was detected in the wild type plants (FIGS. 13-15).

To assess whether the enhanced expression of invertase would affect the normal growth and development of transgenic plants, PCR and RT-PCR confirmed homozygous $T_3$ plants were grown in the greenhouse. We observed that transgenic plants grew faster and produced larger ears, as compared to the wild type plants. The seeds were larger and heavier as well (data not shown). To assure these phenotype changes, homozygous $T_3$ plants were grown in Jiyuan (Henan Province, China) for field trial (transgenic trial penult number: 2011-T032). These transgenic plants produced greater biomass (FIG. 16), bigger grain cobs (FIG. 17), and seeds (FIG. 13-15), resulting in improved grain yield per plant (Table 3).

TABLE 3

Mean comparisons for starch contents in field grown wild-type Ye478 (WT) and transgenic maize

|  | Amylopectin content (%) | Amylose content (%) | Total starch content (%) | Amylopectin/ Amylose |
|---|---|---|---|---|
| WT | $40.75 \pm 1.75^b$ | $15.90 \pm 1.89^a$ | $56.65 \pm 0.16^b$ | $2.59 \pm 0.42^{bc}$ |
| AtGIF1-1 | $40.35 \pm 0.07^b$ | $15.56 \pm 0.96^a$ | $56.44 \pm 0.50^b$ | $2.51 \pm 0.06^c$ |

TABLE 3-continued

Mean comparisons for starch contents in field
grown wild-type Ye478 (WT) and transgenic maize

| | Amylopectin content (%) | Amylose content (%) | Total starch content (%) | Amylopectin/ Amylose |
|---|---|---|---|---|
| AtGIF1-3 | $45.20 \pm 1.63^a$ | $14.94 \pm 0.12^a$ | $60.14 \pm 1.51^a$ | $3.13 \pm 0.12^b$ |
| AtGIF1-4 | $45.35 \pm 0.94^a$ | $12.02 \pm 0.86^b$ | $57.14 \pm 2.03^b$ | $3.85 \pm 0.02^a$ |
| AtGIF1-5 | $37.85 \pm 1.58^b$ | $15.77 \pm 1.48^a$ | $53.62 \pm 0.30^c$ | $2.42 \pm 0.33^c$ |
| WT | $40.75 \pm 1.75^c$ | $15.90 \pm 1.89^a$ | $56.65 \pm 0.16^c$ | $2.59 \pm 0.42^b$ |
| OsGIF1-1 | $50.88 \pm 0.37^a$ | $12.82 \pm 1.02^{bc}$ | $63.70 \pm 0.65^a$ | $4.16 \pm 0.39^a$ |
| OsGIF1-3 | $45.34 \pm 0.93^b$ | $15.72 \pm 1.48^{ab}$ | $61.32 \pm 1.06^b$ | $2.81 \pm 0.04^b$ |
| OsGIF1-4 | $52.17 \pm 0.93^a$ | $11.85 \pm 0.39^c$ | $64.02 \pm 0.67^a$ | $4.40 \pm 0.21^a$ |
| OsGIF1-6 | $40.82 \pm 1.34^c$ | $15.03 \pm 1.68^{ab}$ | $56.35 \pm 0.69^c$ | $2.66 \pm 0.15^b$ |
| WT | $40.75 \pm 1.75^d$ | $15.90 \pm 1.89^a$ | $56.65 \pm 0.16^d$ | $2.59 \pm 0.42^b$ |
| ZmGIF1-1 | $53.48 \pm 1.71^a$ | $12.58 \pm 0.29^b$ | $67.66 \pm 1.32^a$ | $4.25 \pm 0.04^a$ |
| ZmGIF1-2 | $47.41 \pm 0.87^c$ | $12.80 \pm 0.30^b$ | $61.42 \pm 1.40^c$ | $3.70 \pm 0.11^a$ |
| ZmGIF1-3 | $52.17 \pm 1.15^{ab}$ | $13.44 \pm 0.43^b$ | $66.06 \pm 2.00^{ab}$ | $3.74 \pm 0.05^a$ |
| ZmGIF1-4 | $50.40 \pm 0.44^b$ | $13.87 \pm 0.56^{ab}$ | $64.03 \pm 0.95^{bc}$ | $3.73 \pm 0.18^a$ |

The Data shown in Table 3 are from plants in randomized complete block design with three replications under natural condition in Jiyuan, Henan Province, China. Forty seeds from homozygous $T_3$ transgenic and WT lines were sown in a double-row plot. The plot was 2.5 m in length, with a width of 1.2 m and an interval of 0.25 m between plants. The plants were thinned at the five-leaf stage, resulting in 20 plants in each plot (a population density of approximately 66,700 plants/ha). Four independently selected transgenic lines were used. Seeds were harvested in October for starch content analyses. Values shown are means±s.e.m. Values labeled with different letters are significantly different by Duncan's multiple comparison tests at P<0.05 (n=3).

To test whether expression of introduced genes increased invertase activity in the transgenic plants, homozygous $T_4$ plants were simultaneously grown in greenhouse and Nanbin farm (Sanya, Hainan province, China). Cell wall invertase activity in leaves and developing seeds of wild type and transgenic plants was examined. Under both growth conditions, transgenic plants grew faster and bigger than the nontransgenic wild type plants (FIG. 18-20). The cell wall invertase activity of leaves (FIG. 21a-c) and developing grains at 12 DAP (FIG. 21d-f) of transgenic lines was significantly higher than that of the wild type plants. This was consistent with the higher glucose and fructose content (FIG. 22b,c; 23), and with the faster shoot growth (FIG. 18) and grain filling (FIG. 22d) of transgenic grains compared to the wild type grains at the early filling stage. The extents of all the phenotype changes were correlated with the expression levels of introduced genes in the transgenic lines: lines showing higher expression levels of transgenes exhibited higher levels of cell wall invertase activity, and consequently produced greater shoot biomass and larger ears with bigger seed size and numbers than did those transgenic lines showing relatively lower expression levels of transgene (FIGS. 13-21).

The growths of $T_5$ cobs of the wild-type and different transgenic lines ($T_4$) were found to differ starting at 7 DAP. Transgenic cobs grew faster and bigger than the wild type controls (FIG. 24-25). Consistently, the transgenic cobs ($T_6$) was bigger (FIGS. 26-28), and the grain yield of transgenic lines was higher than the nontransgenic controls. The enhanced grain yield resulted from both increased seed numbers and seed sizes (weights) per ear (Table 3).

The grain yield and yield increase were affected by the weather and location where the plants were grown. The final grain yield in Jiyuan (2011) was lower than that in Zhangye (2012) where the sunlight is stronger (Table 3). However, transgenic lines grown in both locations consistently showed a higher grain yield per plant relative to wild type plants. The grain yield increased 145.3% for AtGIF1-3, 141.2% for OsGIF1-4, 127.0% for ZmGIF1-3 in 2011, and 53.6% for AtGIF1-3, 65.8% for OsGIF1-4, 109.2% for ZmGIF1-1 in 2012.

It has been well documented that invertase-mediated sucrose cleavage directly or indirectly regulates the levels of key plant hormones during seed development. Indole-3-acetic acid (IAA) is the predominant hormone in kernels of maize. Although no significant phenotype changes is caused in the vegetative growth, the deficiency of Mn1 locus in mn1 leads to pleiotropic changes including altered sugar levels and decreased IAA accumulation throughout seed development (FIG. 12a-e). Molecular study revealed that the decreased levels of IAA in mn1 seeds are mainly due to the reduced expression of the endosperm-specific ZmTar1 gene of the IPA branch. We hypothesized that constitutive expression of the introduced invertase gene would increase IAA accumulations in transgenic plants, which subsequently promoted the shoot growth. Indeed, except those lines expressing AtGIF1, all the transgenic lines expressing OsGIF1 or ZmGIF1 accumulated more IAA in the leaves than did the notransgenic controls (FIG. 29a). This is also consistent with the higher transcriptional level of ZmTar1 in the leaves of these transgenic plants (FIG. 29b). The normal vegetative growth and the unchanged ZmTar1 expression in the leaves of mn1 mutant further supported this hypothesis (FIG. 30a). We compared the photosynthesis between wild type and transgenic plants grown in the greenhouse. Both maximal efficiency of PSII photochemistry (Fv/Fm) and photosynthetic electron transport rate (ETR) in transgenic plants were higher (FIG. 31). All these results suggested that photosynthesis was also improved in transgenic plants and such an improvement was associated with an improvement in the actual PSII efficiency.

In addition, we examined the starch content and composition of seeds from wild type and transgenic plants. When checked with scanning electron microscope, no significant difference was seen between wild type and mn1 seed starch (FIG. 30b-d). However, larger starch granules were observed in the seeds of transgenic plants (FIG. 32). Detailed examination demonstrated that the total starch content, the ratios of amylopectin to amylase, and the percentages of large starch granules (>20 µm in diameter) significantly increased in the seeds of all transgenic lines which showed high expression levels of introduced invertase genes (Tables 3-6). The total starch content increased 6.2% in AtGIF1-3, 13% in OsGIF1-4, and 19.4% in ZmGIF1-1 (Tables 3).

used. Seeds were harvested in October for starch granule volume analyses. Values shown are means±s.e.m. Values

TABLE 4

Mean comparisons for size distribution of starch granule (%) in field grown wild-type Ye478 (WT) and transgenic maize kernels

| Granule diameter | <0.8 μm | 0.8~2 μm | 2~10 μm | 10~20 μm |
|---|---|---|---|---|
| WT | 53.56 ± 1.09[b] | 42.23 ± 1.77[a] | 3.87 ± 0.09[c] | 0.30 ± 0.09[a] |
| AtGIF1-1 | 63.79 ± 0.81[a] | 31.18 ± 0.50[b] | 4.68 ± 0.30[bc] | 0.29 ± 0.01[a] |
| AtGIF1-3 | 61.53 ± 0.42[a] | 32.48 ± 0.51[b] | 5.58 ± 0.57[a] | 0.32 ± 0.04[a] |
| AtGIF1-4 | 61.88 ± 0.83[a] | 32.54 ± 0.64[b] | 5.18 ± 0.30[ab] | 0.32 ± 0.03[a] |
| AtGIF1-5 | 63.45 ± 1.54[a] | 31.93 ± 1.00[b] | 4.27 ± 0.49[c] | 0.29 ± 0.03[a] |
| WT | 53.56 ± 1.09[a] | 42.23 ± 1.77[a] | 3.87 ± 0.09[a] | 0.30 ± 0.09[a] |
| OsGIF1-1 | 54.54 ± 1.84[a] | 40.22 ± 1.46[a] | 4.82 ± 0.39[a] | 0.34 ± 0.07[a] |
| OsGIF1-3 | 57.15 ± 1.38[a] | 37.35 ± 1.33[a] | 5.08 ± 0.70[a] | 0.33 ± 0.07[a] |
| OsGIF1-4 | 52.83 ± 1.55[a] | 41.30 ± 1.80[a] | 5.43 ± 0.68[a] | 0.34 ± 0.06[a] |
| OsGIF1-6 | 53.61 ± 1.94[a] | 41.28 ± 1.73[a] | 4.74 ± 0.33[a] | 0.30 ± 0.01[a] |
| WT | 53.56 ± 1.09[a] | 42.23 ± 1.77[a] | 3.87 ± 0.08[b] | 0.30 ± 0.05[a] |
| ZmGIF1-1 | 54.54 ± 1.90[a] | 39.89 ± 1.73[a] | 5.11 ± 0.37[a] | 0.36 ± 0.05[a] |
| ZmGIF1-2 | 58.85 ± 1.41[a] | 37.31 ± 1.48[a] | 3.55 ± 0.07[b] | 0.24 ± 0.01[b] |
| ZmGIF1-3 | 59.45 ± 0.65[a] | 36.64 ± 0.5[a] | 3.63 ± 0.14[b] | 0.24 ± 0.01[b] |
| ZmGIF1-4 | 59.28 ± 0.76[a] | 36.85 ± 0.89[a] | 3.58 ± 0.13[b] | 0.23 ± 0.01[b] |

Data are from plants in randomized complete block design with three replications under natural condition in Jiyuan, Henan Province, China, in June, 2011. Forty seeds from homozygous $T_3$ transgenic and WT lines were sown in a double-row plot. The plot was 2.5 m in length, with a width of 1.2 m and an interval of 0.25 m between plants. The plants were thinned at the five-leaf stage, resulting in 20 plants in each plot (a population density of approximately 66700 plants/ha). Four independently selected transgenic lines were used. Seeds were harvested in October for starch granule size analyses. Values shown are means±s.e.m. Values labeled with different letters are significantly different by LSD multiple comparison tests at P<0.05 (n=3).

labeled with different letters are significantly different by LSD multiple comparison tests at P<0.05 (n=3).

The above results clearly show that GIF1 genes and their homologs would be useful in applications to regulate grain filling and crop yields. Various related sequences having high homologies and/or conserved sequences should also have these activities. FIG. 33 shows Sequence alignments of GIF1 with homologous proteins from different plants. The BLAST search program (http://www.ncbi.nlm.nih.gov/BLAST/) was used to look for invertase sequences homologous to GIF1. The highest homologous invertase sequences were aligned using a GENEDOC software. The aligned invertases include the functionally known OsGIF1 (rice ADE60571.1), OsCIN1

TABLE 5

Mean comparisons for volume distribution of starch granule (%) in field grown wild-type Ye478 (WT) and transgenic maize kernels

| Granule diameter | <0.8 μm | 0.8~2 μm | 2~10 μm | 10~20 μm | >20 μm |
|---|---|---|---|---|---|
| WT | 0.71 ± 0.15[a] | 4.79 ± 0.22[a] | 11.24 ± 0.08[ab] | 56.05 ± 1.80[a] | 27.13 ± 1.23[d] |
| AtGIF1-1 | 0.48 ± 0.12[b] | 3.19 ± 0.05[b] | 11.49 ± 0.22[ab] | 44.67 ± 1.75[b] | 40.17 ± 1.34[c] |
| AtGIF1-3 | 0.37 ± 0.01[b] | 1.71 ± 0.17[c] | 9.52 ± 0.26[c] | 26.75 ± 1.67[d] | 61.65 ± 1.49[a] |
| AtGIF1-4 | 0.42 ± 0.03[b] | 2.06 ± 0.14[b] | 10.39 ± 0.09[bc] | 32.60 ± 0.99[c] | 54.53 ± 1.10[b] |
| AtGIF1-5 | 0.63 ± 0.11[ab] | 2.86 ± 0.09[b] | 11.96 ± 0.07[a] | 42.61 ± 1.87[b] | 41.94 ± 1.94[c] |
| WT | 0.71 ± 0.15[a] | 4.79 ± 0.22[a] | 11.24 ± 0.08[a] | 56.05 ± 1.80[a] | 27.13 ± 1.23[b] |
| OsGIF1-1 | 0.42 ± 0.17[bc] | 2.65 ± 0.10[b] | 10.03 ± 0.29[b] | 36.72 ± 1.34[b] | 50.17 ± 1.82[a] |
| OsGIF1-3 | 0.37 ± 0.07[c] | 2.19 ± 0.28[b] | 9.52 ± 0.49[b] | 31.18 ± 1.34[b] | 56.74 ± 1.77[a] |
| OsGIF1-4 | 0.34 ± 0.09[c] | 2.23 ± 0.37[b] | 9.54 ± 0.27[b] | 30.91 ± 1.69[b] | 56.98 ± 1.90[a] |
| OsGIF1-6 | 0.49 ± 0.02[ab] | 3.10 ± 0.23[b] | 10.06 ± 0.15[b] | 37.98 ± 0.75[b] | 48.37 ± 1.86[a] |
| WT | 0.71 ± 0.15[a] | 4.79 ± 0.22[a] | 11.24 ± 0.08[a] | 56.05 ± 1.80[a] | 27.13 ± 1.23[b] |
| ZmGIF1-1 | 0.38 ± 0.14[b] | 2.38 ± 0.10[b] | 9.28 ± 0.09[c] | 36.42 ± 1.51[b] | 51.54 ± 1.87[a] |
| ZmGIF1-2 | 0.66 ± 0.06[a] | 3.84 ± 0.08[b] | 9.37 ± 0.57[c] | 44.00 ± 1.02[b] | 42.13 ± 1.49[a] |
| ZmGIF1-3 | 0.75 ± 0.01[a] | 4.29 ± 0.01[b] | 10.54 ± 0.29[ab] | 41.23 ± 1.82[b] | 44.29 ± 1.17[a] |
| ZmGIF1-4 | 0.63 ± 0.03[a] | 3.65 ± 0.21[b] | 9.62 ± 0.29[bc] | 40.10 ± 1.89[b] | 45.99 ± 1.61[a] |

Data are from plants in randomized complete block design with three replications under natural condition in Jiyuan, Henan Province, China, in June, 2011. Forty seeds from homozygous $T_3$ transgenic and WT lines were sown in a double-row plot. The plot was 2.5 m in length, with a width of 1.2 m and an interval of 0.25 m between plants. The plants were thinned at the five-leaf stage, resulting in 20 plants in each plot (a population density of approximately 66700 plants/ha). Four independently selected transgenic lines were (rice ADE60654.1), PtINCW1 (PaxgINV1 ABY81288.1), PtINCW2 (PaxgINV2 ABY81289.1) and ZmCWIN1 (maize AAD02511.1), ZmGIF1 (also known as Mn1; NM_001112126), and functionally unknown invertases ATCWINV2 (Arabidopsis NP_190828.2) and AtGIF1 (Arabidopsis NP_566464.1). The β-fructosidase motif, the Cys catalysis site, and the conserved glycosylation motif are indicated. That these sequences have these conserved domains suggests that variants of the above described sequences would have the same functions if they also include these conserved domains.

All the documents cited herein are incorporated into the invention as reference, as if each of them is individually incorporated. Further, it would be appreciated that, in the above teaching of the invention, the skilled in the art could make certain changes or modifications to the invention, and these equivalents would still be within the scope of the invention defined by the appended claims of the present application.

What is claimed is:

1. A method for regulating grain filling in a crop plant, comprising introducing a crop grain filling gene into the crop plant, wherein the crop grain filling gene encodes a protein selected from the group consisting of:
   (a) a polypeptide having the amino acid sequence of SEQ ID NO: 7 or 10; or
   (b) a polypeptide derived from the polypeptide of (a) by substitution, deletion or addition of 1-20 amino acid residues in the amino acid sequence of SEQ ID NO: 7 or 10 and having an activity of promoting crop grain filling.

2. The method of claim 1, wherein the grain filling gene encodes the polypeptide having the amino acid sequence of SEQ ID NO: 7 or 10.

3. The method of claim 1, wherein the grain filling gene has a sequence selected from the group consisting of:
   (1) the nucleotide sequence of SEQ ID NO: 6 or 9;
   (2) the nucleotide sequence of SEQ ID NO: 8 or 11; or
   (3) a nucleotide sequence complementary to the full length of the nucleotide sequence of (1) or (2).

4. The method of claim 3, wherein the grain filing gene has the nucleotide sequence of SEQ ID NO: 8 or 11.

5. A genetically engineered crop plant produced by the method of claim 1, wherein the crop plant comprises the gene encoding:
   (a) the polypeptide having the amino acid sequence of SEQ ID NO: 7 or 10; or
   (b) the polypeptide derived from the polypeptide of (a) by substitution, deletion or addition of 1-20 amino acid residues in the amino acid sequence of SEQ ID NO: 7 or 10 and having the activity of promoting crop grain filling.

* * * * *